US009644196B2

(12) United States Patent
Zwaal

(10) Patent No.: US 9,644,196 B2
(45) Date of Patent: May 9, 2017

(54) PLASMINOGEN AND PLASMIN VARIANTS

(75) Inventor: Richard Reinier Zwaal, Heverlee (BE)

(73) Assignee: ThromboGenics NV, Heverlee (BE)

( * ) Notice: Subject to any disclaimer, the term of this patent is extended or adjusted under 35 U.S.C. 154(b) by 262 days.

(21) Appl. No.: 14/238,249

(22) PCT Filed: Aug. 13, 2012

(86) PCT No.: PCT/EP2012/065832
§ 371 (c)(1),
(2), (4) Date: Mar. 3, 2014

(87) PCT Pub. No.: WO2013/024074
PCT Pub. Date: Feb. 21, 2013

(65) Prior Publication Data
US 2014/0205588 A1 Jul. 24, 2014

Related U.S. Application Data

(60) Provisional application No. 61/522,817, filed on Aug. 12, 2011.

(30) Foreign Application Priority Data

Mar. 26, 2012 (EP) .................................. 12161185

(51) Int. Cl.
| | | |
|---|---|---|
| C12N 9/68 | (2006.01) |
| A61K 38/17 | (2006.01) |
| A61K 38/48 | (2006.01) |
| C12Q 1/37 | (2006.01) |
| C07K 14/47 | (2006.01) |
| A61K 45/06 | (2006.01) |
| A61K 38/00 | (2006.01) |

(52) U.S. Cl.
CPC ........ *C12N 9/6435* (2013.01); *A61K 38/1709* (2013.01); *A61K 38/484* (2013.01); *A61K 45/06* (2013.01); *C07K 14/47* (2013.01); *C12Q 1/37* (2013.01); *C12Y 304/21007* (2013.01); *A61K 38/00* (2013.01)

(58) Field of Classification Search
CPC .................................................. C12N 9/6435
See application file for complete search history.

(56) References Cited

U.S. PATENT DOCUMENTS

| | | | |
|---|---|---|---|
| 3,208,908 A | 9/1965 | Maxwell et al. |
| 4,122,158 A | 10/1978 | Schmitt |
| 4,462,980 A | 7/1984 | Diedrichsen et al. |
| 4,774,087 A | 9/1988 | Wu et al. |
| 5,087,572 A | 2/1992 | Castellino et al. |
| 5,288,489 A | 2/1994 | Reich et al. |
| 5,304,118 A | 4/1994 | Trese et al. |
| 5,304,383 A | 4/1994 | Eibl et al. |
| 5,407,673 A | 4/1995 | Reich et al. |
| 5,520,912 A | 5/1996 | Eibl et al. |
| 5,597,800 A | 1/1997 | Eibl et al. |
| 5,776,452 A | 7/1998 | Eibl et al. |
| 5,879,923 A | 3/1999 | Yago et al. |
| 6,057,122 A | 5/2000 | Davidson |
| 6,355,243 B1 | 3/2002 | Novokhatny et al. |
| 6,585,972 B2 | 7/2003 | Peyman |
| 6,733,750 B1 | 5/2004 | Peyman |
| 6,787,135 B2 | 9/2004 | Trese et al. |
| 6,899,877 B2 | 5/2005 | Peyman |
| 6,946,438 B1 | 9/2005 | Nagai et al. |
| 6,964,764 B2 | 11/2005 | Zimmerman et al. |
| 6,969,515 B2 | 11/2005 | Jesmok et al. |
| 7,445,775 B2 | 11/2008 | Collen et al. |
| 7,544,500 B2 | 6/2009 | Bradley et al. |
| 7,547,435 B2 | 6/2009 | Pakola et al. |
| 7,776,026 B2 | 8/2010 | Trese et al. |
| 7,803,368 B2 | 9/2010 | Pakola et al. |
| 7,867,489 B2 | 1/2011 | Pakola et al. |
| 7,871,608 B2 | 1/2011 | Zimmerman et al. |
| 7,914,783 B2 | 3/2011 | Pakola et al. |
| 8,034,913 B2 | 10/2011 | Hunt et al. |
| 8,101,394 B2 | 1/2012 | Novokhatny |
| 8,182,808 B2 | 5/2012 | Novokhatny |
| 8,231,869 B2 | 7/2012 | Scuderi, Jr. et al. |
| 8,268,782 B2 | 9/2012 | Rebbeor et al. |
| 8,383,105 B2 | 2/2013 | Pakola et al. |
| 8,420,079 B2 | 4/2013 | Hunt et al. |
| 8,460,655 B2 | 6/2013 | Pakola et al. |
| 8,512,980 B2 | 8/2013 | Novokhatny |
| 9,121,014 B2 | 9/2015 | Zwaal |
| 9,226,953 B2 | 1/2016 | Zwaal |

(Continued)

FOREIGN PATENT DOCUMENTS

| | | |
|---|---|---|
| CN | 1560239 | 1/2005 |
| CN | 1592634 | 3/2005 |

(Continued)

OTHER PUBLICATIONS

Astrup et al., "The fibrin plate method for estimating fibrinolytic activity," *Arch Biochem. Biophys.*, 346-351 (1952).
Bergmann et al., "Clot-selective coronary thrombolysis with tissue-type plasminogen activator," *Science*, 220:1181-1183 (1983).
Castellino et al., "Rabbit plasminogen and plasmin isozymes," *Methods Enzymol.*, 45:273-286 (1976).
Christensen et al., "Enzymic properties of the neo-plasmin-Val-422 (miniplasmin)," *Biochim. Biophys. Acta*, 567:472-481 (1979).
Christensen et al., "Stopped-flow fluorescence kinetics of bovine alpha 2-antiplasmin inhibition of bovine midiplasmin," *Biochem J.*, 305:97-102 (1995).
Collen et al., "Thrombolysis with human extrinsic (tissue-type) plasminogen activator in rabbits with experimental jugular vein thrombosis. Effect of molecular form and dose of activator, age of the thrombus, and route of administration," *J Clin. Invest.*, 71:368-376 (1983).
Collen et al., Isolation and characterisation of natural and recombinant staphylokinase, *Fibrinolysis*, 6, 203-213 (1992).
Dawson et al., "Substitution of arginine 719 for glutamic acid in human plasminogen substantially reduces its affinity for streptokinase," *Biochemistry*, 33(40):12042-12047 (1994).

(Continued)

*Primary Examiner* — Nashaat Nashed
*Assistant Examiner* — William W Moore
(74) *Attorney, Agent, or Firm* — Fish & Richardson P.C.

(57) ABSTRACT

The invention relates to variants of plasminogen and plasmin comprising one or more point mutations in the catalytic domain which reduce or prevent autocatalytic destruction of the protease activity of plasmin. Compositions, uses and methods of using said variants of plasminogen and plasmin are also disclosed.

45 Claims, 14 Drawing Sheets

(56) References Cited

U.S. PATENT DOCUMENTS

Figure 3:
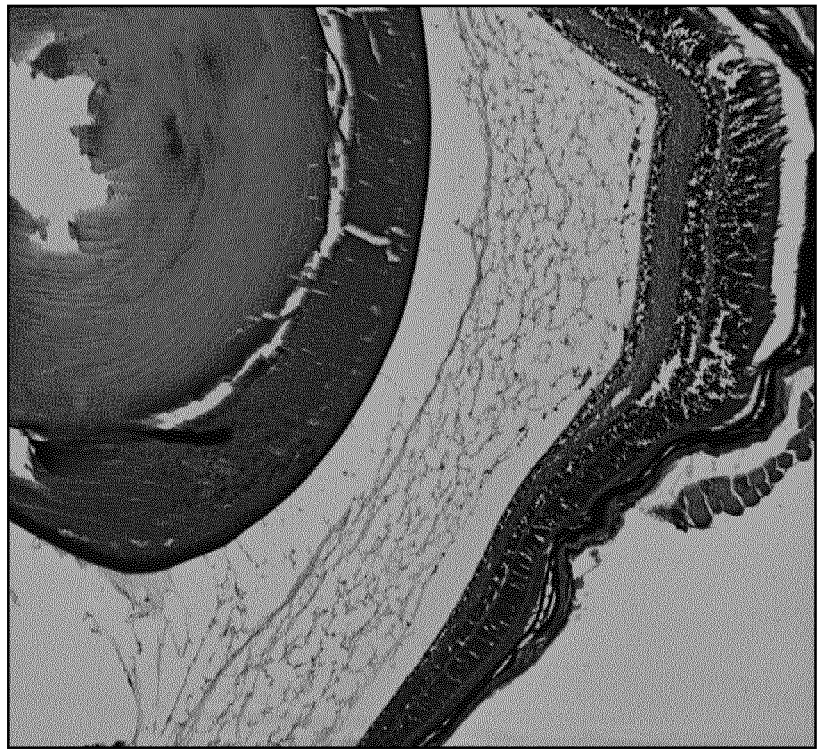

| | | | |
|---|---|---|---|
| 2003/0147877 A1 | 8/2003 | Trese et al. |
| 2004/0081643 A1 | 4/2004 | Peyman |
| 2006/0024349 A1 | 2/2006 | Trese et al. |
| 2007/0212358 A1 | 9/2007 | Bartels |
| 2007/0231352 A1 | 10/2007 | Tsai |
| 2011/0300123 A1 | 12/2011 | Pakola et al. |
| 2012/0114630 A1 | 5/2012 | Zwaal |
| 2013/0164273 A1 | 6/2013 | Zimmerman et al. |
| 2013/0164815 A1 | 6/2013 | Dadd et al. |
| 2013/0195887 A1 | 8/2013 | Pakola et al. |
| 2013/0202613 A1 | 8/2013 | Pakola et al. |
| 2013/0273028 A1 | 10/2013 | Zwaal |
| 2013/0302304 A1 | 11/2013 | Pakola et al. |

FOREIGN PATENT DOCUMENTS

| | | |
|---|---|---|
| CN | 101209347 | 7/2008 |
| EP | 0 009 879 | 4/1980 |
| EP | 0 480 906 | 4/1992 |
| EP | 0 631 786 | 6/1998 |
| EP | 1 117 437 | 7/2001 |
| EP | 1 232 251 | 8/2002 |
| EP | 1 232 252 | 8/2002 |
| EP | 1 232 254 | 8/2002 |
| EP | 1 343 903 | 9/2003 |
| EP | 1 581 254 | 10/2005 |
| EP | 1 740 698 | 1/2007 |
| EP | 2 327 415 | 6/2011 |
| EP | 2 327 416 | 6/2011 |
| GB | 2 393 121 | 3/2004 |
| JP | H05-502375 | 4/1993 |
| WO | WO 89/01336 | 2/1989 |
| WO | WO 90/13640 | 11/1990 |
| WO | WO 91/08297 | 6/1991 |
| WO | WO 91/09118 | 6/1991 |
| WO | WO 93/07893 | 4/1993 |
| WO | WO 93/15189 | 8/1993 |
| WO | WO 97/01631 | 1/1997 |
| WO | WO 00/18436 | 4/2000 |
| WO | WO 01/04269 | 1/2001 |
| WO | WO 01/24817 | 4/2001 |
| WO | WO 01/36608 | 5/2001 |
| WO | WO 01/36609 | 5/2001 |
| WO | WO 01/36611 | 5/2001 |
| WO | WO 01/58921 | 8/2001 |
| WO | WO 02/50290 | 6/2002 |
| WO | WO 02/078564 | 10/2002 |
| WO | WO 03/033019 | 4/2003 |
| WO | WO 03/066842 | 8/2003 |
| WO | WO 2004/045558 | 6/2004 |
| WO | WO 2004/052228 | 6/2004 |
| WO | WO 2005/016455 | 2/2005 |
| WO | WO 2005/078109 | 8/2005 |
| WO | WO 2005/105990 | 11/2005 |
| WO | WO 2006/122249 | 11/2006 |
| WO | WO 2007/047874 | 4/2007 |
| WO | WO 2007/070390 | 6/2007 |
| WO | WO 2007/078761 | 7/2007 |
| WO | WO 2007/101005 | 9/2007 |
| WO | WO 2008/026999 | 3/2008 |
| WO | WO 2008/054592 | 5/2008 |
| WO | WO 2009/073457 | 6/2009 |
| WO | WO 2009/073471 | 6/2009 |
| WO | WO 2011/004011 | 1/2011 |
| WO | WO 2012/093132 | 7/2012 |
| WO | WO 2013/024074 | 2/2013 |

OTHER PUBLICATIONS

Deacon et al., "Technetium 99m-plasmin: a new test for the detection of deep vein thrombosis," *Br. J. Radiol.*, 53:673-677 (1980).
Deutsch et al., "Plasminogen: purification from human plasma by affinity chromatography," *Science*, 170:1095-1096 (1970).
GenBank Accession No. AAA36451, plasminogen [*Homo sapiens*] (Apr. 27, 1993), 3 pages.
Grella et al., "Activation of human plasminogen by staphylokinase. Direct evidence that preformed plasmin is necessary for activation to occur," *Blood*, 89:1585-1589 (1997).
Hendrickson et al., "Incorporation of nonnatural amino acids into proteins," *Annu. Rev. Biochem.*, 73:147-176 (2004).
Hotchkiss et al., "A new pan species model for the measurement of in vivo thrombolysis," *Thromb. Haemost.*, 58:107—Abstract 377 (1987).
Hunt et al., "Simplified recombinant plasmin: production and functional comparison of a novel thrombolytic molecule with plasma-derived plasmin," *Thromb. Haemost.*, 100(3):413-419 (2008).
Jespers et al., "Arginine 719 in human plasminogen mediates formation of the staphylokinase:plasmin activator complex," *Biochemisty*, 37(18):6380-6386 (1998).
Jespersen et al., "The autodigestion of human plasmin follows a bimolecular mode of reaction subject to product inhibition," 41:395-404 (1986).
Linde et al., "Elimination of the Cys558-Cys566 bond in Lys78-plasminogen—effect on activation and fibrin interaction," *Eur. J Biochem.*, 251:472-479 (1998).
Mhashilkar et al., "Breaching the conformational integrity of the catalytic triad of the serine protease plasmin: localized disruption of a side chain of His-603 strongly inhibits the amidolytic activity of human plasmin," *Proc. Natl. Acad. Sci. USA*, 90:5374-5377 (1993).
Nguyen et al., "Protein composition of plasmin preparation "homolysin"," *Prep. Biochem.*, 11:159-172 (1981).
Ohyama et al., "Nonlysine-analog plasminogen modulators promote autoproteolytic generation of plasmin(ogen) fragments with angiostatin-like activity," *Eur. J Biochem.*, 271:809-820 (2004).
Papadopoulos et al., "COBALT: constraint-based alignment tool for multiple protein sequences," *Bioinformatics*, 23:1073-79 (2007).
Parry et al., "Molecular mechanisms of plasminogen activation: bacterial cofactors provide clues," *Trends Biochem Sci.*, 25(2):53-59 (2000).
Peisach et al., "Crystal structure of the proenzyme domain of plasminogen," *Biochemistry*, 38:11180-11188 (1999).
Powell et al., "Activation of human neo-plasminogen-Val$_{442}$ by urokinase and streptokinase and a kinetic characterization of neoplasmin-Val$_{442}$," *J Biol. Chem.*, 255:5329-5335 (1980).
Robbins et al., "Human plasminogen and plasmin," *Methods Enzymol.*, 19:184-199 (1970).
Ruyssen et al., Chapter IX—Plasmin, In "Pharmaceutical Enzymes," Story-Scientia, Gent, Belgium, 123-131 (1978).
Salonen et al., "Rapid appearance of plasmin in tear fluid after ocular allergen exposure," *Clin. Exp. Immunol.*, 73(1):146-148 (1988).
Shi et al., "Differential autolysis of human plasmin at various pH levels," *Thromb. Res.*, 51:355-364 (1988).
Takeda-Shitaka et al., "Structural studies of the interactions of normal and abnormal human plasmins with bovine basic pancreatic trypsin inhibitor," *Chem. Pharm. Bull*, 47:322-328 (1999).
Terzyan et al., "Characterization of Lys-698-to-Met substitution in human plasminogen catalytic domain," *Proteins*, 56(2):277-284 (2004).
Ueshima et al., "Stabilization of plasmin by lysine derivatives," *Clin. Chim. Acta*, 245:7-18 (1996).
Verstraete, "Clinical application of inhibitors of fibrinolysis," *Drugs*, 29:236-261 (1985).
Wang et al., "Structure and function of microplasminogen: I. Methionine shuffling, chemical proteolysis, and proenzyme activation," *Protein Sci.*, 4:1758-1767 (1995).
Wang et al., "Structure and function of microplasminogen: II. Determinants of activation by urokinase and by the bacterial activator streptokinase," *Protein Sci.*, 4:1768-1779 (1995).
Wang et al., "Zymogen activation in the streptokinase-plasminogen complex. Ile1 is required for the formation of a functional active site," *Eur. J. Biochem.*, 267:3994-4001 (2000).
Wang et al., "Human plasminogen catalytic domain undergoes an unusual conformational change upon activation," *J. Mol. Biol.*, 295(4):903-914 (2000).
Weinstein et al., "Differential specificities of the thrombin, plasmin and trypsin with regard to synthetic and natural substrates and inhibitors," *Biochim. Biophys. Acta*, 258:577-590 (1972).

(56) References Cited

OTHER PUBLICATIONS

Welsh et al., "Effect of lactacidosis on pyridine nucleotide stability during ischemia in mouse brain," *J. Neurochem.*, 49:846-851 (1987).
International Search Report for App. Ser. No. PCT/EP2010/059902, mailed Aug. 25, 2010, 9 pages.
International Preliminary Report on Patentability for App. Ser. No. PCT/EP2010/059902, dated Jan. 10, 2012, 6 pages.
International Search Report for App. Ser. No. PCT/EP2012/065832, dated Nov. 19, 2012, 6 pages.
Wang et al., "Deletion of Ile1 changes the mechanism of streptokinase: evidence for the molecular sexuality hypothesis," *Biochemistry*, 38:5232-5240 (1999).
U.S. Appl. No. 14/940,245, filed Nov. 13, 2015, Zwaal.
Ponting et al., "Plasminogen: a structural review," *Blood Coagulation and Fibrinolysis*, 3:605-614 (Aug. 1992).
Xiaoqiang Wang et al., "Crystal Structure of the Catalytic Domain of Human Plasmin Complexed with Streptokinase," *Science*, 281:1662-1665 (Sep. 11, 1998).

```
1          11         21         31         41         51
|          |          |          |          |          |
EPLDDYVNTQ GASLFSVTKK QLGAGSIEEC AAKCEEDEEF TCRAFQYHSK EQQCVIMAEN
61         71         81         91         101        111
|          |          |          |          |          |
RKSSIIIRMR DVVLFEKKVY LSECKTGNGK NYRGTMSKTK NGITCQKWSS TSPHRPRFSP
121        131        141        151        161        171
|          |          |          |          |          |
ATHPSEGLEE NYCRNPDNDP QGPWCYTTDP EKRYDYCDIL ECEEECMHCS GENYDGKISK
181        191        201        211        221        231
|          |          |          |          |          |
TMSGLECQAW DSQSPHAHGY IPSKFPNKNL KKNYCRNPDR ELRPWCFTTD PNKRWELCDI
241        251        261        271        281        291
|          |          |          |          |          |
PRCTTPPPSS GFTYQCLKGT GENYRGNVAV TVSGHTCQHW SAQTPHTHNR TPENFPCKNL
301        311        321        331        341        351
|          |          |          |          |          |
DENYCRNPDG KRAPWCHTTN SQVRWEYCKI PSCDSSPVST EQLAPTAPPE LTPVVQDCYH
361        371        381        391        401        411
|          |          |          |          |          |
GDGQSYRGTS STTTTGKKCQ SWSSMTPHRH QKTPENYPNA GLTMNYCRNP DADKGPWCFT
421        431        441        451        461        471
|          |          |          |          |          |
TDPSVRWEYC NLKKCSGTEA SVVAPPPVVL LPDVETPSEE DCMFGNGKGY RGKRATTVTG
481        491        501        511        521        531
|          |          |          |          |          |
TPCQDWAAQE PHRHSIFTPE TNPRAGLEKN YCRNPDGDVG GPWCYTTNPR KLYDYCDVPQ
541        551        561        571        581        591
|          |          |1         9|         19|        29|       39
|          |          |/         |          |          |          |
CAAPSFDCGK PQVEPKKCPG RVVGGCVAHP HSWPWQVSLR TRFGMHFCGG TLISPEWVLT
601        611        621        631        641        651
|       49 |       59 |       69 |       79 |       89 |       99
|          |          /          |          |          |          |
AAHCLEKSPR PSSYKVILGA HQEVNLEPHV QEIEVSRLFL EPTRKDIALL KLSSPAVITD
661        671        681        691        701        711
|       109|       119|       129|       139|       149|       159
|          |          /          |          |          |          |
KVIPACLPSP NYVVADRTEC FITGWGETQG TFGAGLLKEA QLPVIENKVC NRYEFLNGRV
721        731        741        751        761        771
|       169|       179|       189|       199|       209|       219
|          |          /          |          |          |          |
QSTELCAGHL AGGTDSCQGD SGGPLVCFEK DKYILQGVTS WGLGCARPNK PGVYVRVSRF
781        791
|       229|
|          |
VTWIEGVMRN N (SEQ ID NO:1)
```

FIGURE 1

COBALT (Constraint-based Multiple Alignment Tool) alignment of plasminogen amino acid sequences
Line # in sequence alignment
1: Homo sapiens /Genbank AAA36451/ human (SEQ ID NO:1)
2: Canis familiaris /Genbank XP_533468/ dog (SEQ ID NO:2)
3: Pan troglodytes /Genbank XP_001152889/ chimpanzee/ isoform 3 (SEQ ID NO:3)
4: Pan troglodytes /Genbank XP_001152830/ chimpanzee/ isoform 2 (SEQ ID NO:4)
5: Pan troglodytes /Genbank XP_518844/ chimpanzee/ isoform 4 (SEQ ID NO:5)
6: Macaca mulatta /Genbank NP_001036540/ Rhesus monkey (SEQ ID NO:6)
7: Pongo abelii /Genbank NP_001126035/ Sumatran orangutan (SEQ ID NO:7)
8: Sus scrofa /Genbank NP_001038055/ pig (SEQ ID NO:8)
9: Bos Taurus /Genbank DAA25966/ cattle (SEQ ID NO:9)
10: Equus Caballus /Genbank XP_001500552/ horse (SEQ ID NO:10)
11: Mus musculus /Genbank EDL02061/ house mouse (SEQ ID NO:11)
12: Rattus norvegicus /Genbank NP_445943/ Norway rat (SEQ ID NO:12)
13: Erinaceus europaeus /Genbank AAC48717/ western European hedgehog (SEQ ID NO:13)
14: Oryctolagus cuniculus /Genbank XP_002715012/ rabbit (SEQ ID NO:14)
15: Pan troglodytes/ Genbank XP_001152435/ chimpanzee/ isoform 1 (SEQ ID NO:15)
16: Ailuropoda melanoleuca/ Genbank EFB19688/panda (SEQ ID NO:16)
17: Papio hamadryas/ Genbank AAB97887/baboon (SEQ ID NO:17)
18: Ovis aries/ Genbank P81286/sheep (SEQ ID NO:18)

FIGURE 2/1

```
                  1           11          21          31          41
                  ▶
1  ----------------MEHKEVLLLLFLKSGQG EPLDDYVNTQGASLFSVTKKQLGAGSIEECAAKCEEDEEFTCR----
2  ----------------MEHKEVLLLLFLKSGHG SLLDDYVNTQGASVFSLTKKQLSVGSIEECAAKCEEETGFICR----
3  ----------------MEHKEVLLLLFLKSGQG EPLDDYVNTQGASLFSVTKKQLGAGSIEECAAKCEEDKEFTCR----
4  ----------------MEHKEVLLLLFLKSGQG EPLDDYVNTQGASLFSVTKKQLGAGSIEECAAKCEEDKEFTCR----
5  -----------------------MLMDYEGQG  EPLDDYVNTKGASLFSITKKQLGAGSIEECAAKCEEDKEFTCR----
6  ----------------MEHKEVLLLLFLKSGQG EPLDDYVNTQGASLFSVTKKQLGAGSIEECAAKCEEEEFTCR-----
7  ----------------MEHKEVLLLLFLKSGQG EPLDDYVNTQGASLFSVTKKQLRAGSIEECAAKCEEKEFTCR-----
8  ----------------MDHKEVLLLLFLKSGLG DSLDDYVNTQGAFLFSLSRKQVAARSVEECAAKCEAETNFICR----
9  MLPASPKMEHKAVVFLILFLKSGLG         DLLDDYVNTQGASLLSLSRKNLAGRSVEDCAAKCEEETDFVCR----
10 ----------------MEHQEVVFLLLFLKSGHG DILDDYVTTQGASLFTFTRKPLSASSIEECEAKCTEETAFICR----
11 ----------------MDHKEVILLFLLLLKPGQG DSLDGYISTQGASLFSLTKKQLAAGGVADCLAKCEGETDFVCR---
12 ----------------MDHKEIILLFLLFLKPGQG DSLDGYVSTQGASLHSLTKKQLAAGSIADCLAKCEGETDFICR---
13 ----------------MQRKELVLFLFLLFLQPGHG IPLDVVTTQGASLSSSTKKQLSVGSTEECAVKCEKETSFICR---
14 ----------------MQRAVVLLLLLLKPGQA  EPLDDYVNTQGASLFSFTKKQLGAASIAECAARCEAETEFTCR---
15 ----------------MEHKEVLLLLFLKSGQG  EPLDDYVNTQGASLFSVTKKQLGAGSIEECAAKCEEDKEFTCRYFHCRCTYPEI---
16 ----------------------------------                                        -FVRR
```

FIGURE 2/2

```
 1  63 ------AFQYHSKEQQCVIMAENRKSSIIIRMRDVVLFEKKVYLSECKTGNGKNYRGTMSKTKNGITCQKWSSTSPHRPR
 2  63 ------SFQYHSKEQQCVIMPENSKSSIVFRMRDVFLFEKRIYLSECKTGNGKTYRGTMAKTKNDVACQKWSDNSPHKPN
 3  63 ------AFQYHSKEQQCVIMAENRKSSIIIRMRDVVLFEKKVYLSECKTGNGKNYRGTMSKTKNGITCQKWSSTSPHRPR
 4  63 ------AFQYHSKEQQCVIMAENRKSSIIIRMRDVVLFEKKVYLSECKTGNGKNYRGTMSKTKNGITCQKWSSTSPHRPR
 5  53 ------AFQYHSKEQQCVIMAENRKSSIVFRMRDVVLFEKKVYLSECKTGNGKNYRGTMSKTKNGITCQKWSSTSPHRPR
 6  63 ------SFQYHSKEQQCVIMAENRKSSIIIRMRDVVLFEKKVYLSECKTGNGKNYRGTMSKTRTGITCQKWSSTSPHRPT
 7  63 ------AFQYHSKEQQCVIMAENRKSSIIIRMRDVVLFEKKVYLSECKTGNGKNYRGTMSKIKNGITCQKWSSTSPHRPR
 8  63 ------AFQYHSKDQQCVVMAENSKTSPIARMRDVVLFEKRIYLSECKTGNGQTYRGTTAETKSGVTCQKWSATSPHVPK
 9  70 ------AFQYHSKEQQCVVMAENSKNTPVFRMRDVILYEKRIYLLECKTGNGQTYRGTTAETKSGVTCQKWSATSPHVPK
10  63 ------AFQYHSKEPRCVLLAENRKSSPVMRMRDVILFEKRIYLSECKTGTGRSYRGTTSKTKNGVSCQKWSDTSPHIPK
11  63 ------SFQYHSKEQQCVIMAENSKTSSIIRMRDVILFEKRVYLSECKTGIGNSYRGTMSRTKSGVACQKWGATFPHVPN
12  63 ------SFQYHSKEQQCVIMAENSKTSSIIRMRDVILFEKKMYLSECKVGNGKYYRGTVSKITKGKYRGTMSKTKTGVTCQKWSDTSPHVPK
13  63 ------SFQYHSKEQQCVIMAENSKSSAIIRRRDVVLFEKRMYLSECKIGNGRSYRGTIKSKTKGFTCQKWSAETPHKPR
14  63 ------SFQYHSKEQQCVIMAENSKSSAIIRRRDVVLFEKRMYLSECKIGNGRSYRGTIKSKTKGFTCQKWSSSYPHKPN
15  74 CNSDGKAFQYHSKEQQCVIMAENRKSSIIIRMRDVVLFEKKVYLSECKTGNGKNYRGTMSKTKNGITCQKWSSTSPHRPR
16   5 ------SFEYHSKEQQCAIMAENSKSSAVFRMRDVILFQKRIYLSECKTGNGKTYRGTMSKTKNGVACQKWSDTFPHKPN
```

FIGURE 2/3

```
         121          131          141          151          161          171          181          191
           |            |            |            |            |            |            |            |
 1  137  FSPATHPSEGLEENYCRNPDNDPQGPWCYTTDPEKRYDYCDILECEEECMHCSGENYDGKISKTMSGLECQAWDSQSPHA
 2  137  YTPEKHPLEGLEENYCRNPDNDENGPWCYTTNPDVRFDYCNIPECEEECMHCSGENYEGKISKTKSGLECQAWNSQTPHA
 3  137  FSPATHPSEGLEENYCRNPDNDPQGPWCYTTDPEKRYDYCDILECEEECMHCSGENYDGKISKTMSGLECQAWDSQSPHA
 4  137  FSPATHPSEGLEENYCRNPDNDPQGPWCYTTDPEKRYDYCDILECEEECMHCSGENYDGKISKTMSGLECQAWDSQSPHA
 5  127  FSPATHPSEGLEENYCRNPDNDGQGPWCYTTDPEKRYDYCDILECEEECMHCSGENYDGKISKTMSGLECQAWDSQSPHA
 6  137  FSPATHPSEGLEENYCRNPDNDAQGPWCYTTDPEERFDYCDIPECEDECMHCSGENYDGKISKTMSGLECQAWDSQSPHA
 7  137  FSPATHPSEGLEENYCRNPDNDAQGPWCYTTDPEHRYDYCDIPECEEACMHCSGENYDGKISKTMSGLECQAWDSQSPHA
 8  144  YSPEKFPLAGLEENYCRNPDNDEKGPWCYTTDPETRFDYCDIPETRFDYCDIPDKRYDYCDIPECEDKCMHCSGENYEGKIAKTMSGRDCQAWDSQSPHA
 9  137  FSPEKFPLAGLEENYCRNPDNDENGPWCYTTDPGTRFDYCDIPECEDECMHCSGENYEGKISKTISGLECQPWASQSPHA
10  137  YSPDKNPSEGLEENYCRNPDNDEKGPWCYTTDPDKRYDYCNIPECEEECMYCSGEKYEGKISKTMSGLDCQAWDSQSPHA
11  137  YSPSTHPNEGLEENYCRNPDNDEQGPWCYTTDPDQRYEYCNIPECEEECMYCSGEKYEGKISKTMSGLDCQSWDSQSPHA
12  137  YSPSTHPSEGLEENYCRNPDNDEQGPWCYTTDPKGPWCYTMDPEVRYEYCEIIQCEDECMHCSGQNYVGKISRTMSGLECQPWDSQIPHP
13  137  FSPDENPSEGLDQNYCRNPDNDEQGPWCYTTDPKGPWCYTMDPEVRYEYCEIIQCEDECMHCSGQNYVGKISRTMSGLECQPWDSQIPHP
14  137  FTPKKYPAEGLEENYCRNPDNDEQGPWCYTTNPDERFDYCDIPECEDECMHCSGENYEGKISKTMSGLECQAWDSQSPHA
15  154  FSPATHPSEGLEENYCRNPDNDPQGPWCYTTDPEKRYDYCDILECEEECMHCSGENYDGKISKTMSGLECQAWDSQSPHA
16   79  YTPEKHPLEGLEENYCRNPDNDEKGPWCYTTDPNQRFDYCSIPQCEDECMHCSGENYEGKVSKTKSGLECQAWNSQTPHA
```

FIGURE 2/4

```
            201        211        221        231        241        251        261        271
            |          |          |          |          |          |          |          |
1   217     HGYIPSKFPNKNLKKNYCRNPDRELRPWCFTTDPNKRWELCDIPRCTTPPPSSGPTYQCLKGTGENYRGNVAVTVSGHTC
2   217     HGYIPSKFPSKNLKMNYCRNPDGELRPWCFTMDPNKRWEFCDIPRCTTPPPSGPTYQCLKGRGESYRGKVSVTVSGHTC
3   217     HGYIPSKFPNKNLKKNYCRNPDGELRPWCFTTDPNKRWELCDIPRCTTPPPSSGPTYQCLKGTGENYRGNVAVTVSGHTC
4   217     HGYIPSKFPNKNLKKNYCRNPDGELRPWCFTTDPNKRWELCDIPRCTTPPPSSGPTYQCLKGTGENYRGNVAVTVSGHTC
5   207     HGYIPSKFPNKNLKKNYCRNPDGELRPWCFTTDPNKRWELCDIPRCTTPPPSSGPTYQCLKGTGENYRGNVAVTVSGHTC
6   217     HGYIPSKFPNKNLKKNYCRNPDGEPRPWCFTTDPNKRWELCDIPRCTTPPPSSGPTYQCLKGTGENYRGDVAVTVSGHTC
7   217     HGYIPSKFPNKNLKKNYCRNPDGEPRPWCFTTDPNKRWELCDIPRCTTPPPSSGPTYQCLKGTGENYRGNVAVTVSGHTC
8   217     HGYIPSKFPNKNLKMNYCRNPDGEPRPWCFTTDPNKRWEFCDIPRCTTPPPSGPTYQCLKGRGENYRGNVAVTVSGHTC
9   224     HGYLPSKFPNKNLKMNYCRNPDGEPRPWCFTTDPQKRWEFCDIPRCTTPPTSGPTYQCLKGTGKNYRGTVSVTAVTESGHTC
10  217     HGYIPSKFPSKNLKMNYCRNPDGEPRPWCFTTDPNKRWEFCDIPRCSTPPPSSGPKYQCLKGRGENYRGRVSVTQSGLTC
11  217     HGYIPSKFPSKNLKMNYCRNPDGEPRPWCFTTDPTKRWEYCDIPRCTTPPPPPGPTYQCLKGRGENYRGTVSVTVSGKTC
12  217     HGYIPAKFPSKNLKMNYCRNPDGEPRPWCFTTDPNKRWEYCDIPRCTTPPPPGPTYQCLKGRGENYRGTVSVTASGKTC
13  217     HGFIPSKFPSKNLKMNYCRNPDGEPRPWCFTMDRNKRWEYCDIPRCTTPPPSGPTYQCLMGNEHYQGNVAVTVSGLTC
14  217     HGYIPSKFPNKNLKKNYCRNPDGEPRPWCFTMDPKKRWELCDIPRCTTPPPSGPTHQCLKGRGESYRGKVARTKSGLTC
15  234     HGYIPSKFPNKNLKKNYCRNPDGELRPWCFTTDPNKRWELCDIPRCTTPPPSSGPTYQCLKGTGENYRGNVAVTVSGHTC
16  159     HGYIPSKFPNKNLKMNYCRNPDGEPRPWCFTMDPNKRWEFCDIPRCTTPPPPSGPTYQCLKGKGENYRGKVSVTASGHTC
```

FIGURE 2/5

```
          281        291        301        311        321        331        341        351
          |          |          |          |          |          |          |          |
 1  297   QHWSAQTPHTHNRTPENFPCKNLDENYCRNPDGKRAPWCHTTNSQVRWEYCKIPSCDSSPVSTEQLAPTA--PPE-LTPV
 2  297   QHWSEQTPHKHNRTPENFPCKNLDENYCRNPDGETAPWCYTTNSEVRWEHCQIPSCESSPITTEYLDAPASVPPE-QTPV
 3  297   QHWSAQTPHTHNRTPENFPCKNLDENYCRNPDGKRAPWCHTTNSQVRWEYCKIPSCDSSLVSTEQLAPTA--PPE-LTPV
 4  297   QHWSAQTPHTHNRTPENFPCKNLDENYCRNPDGKRAPWCHTTNSQVRWEYCKIPSCDSSLVSTEQLAPTA--PPE-LTPV
 5  287   QHWSAQTPHTHNRTPENFPCKNLDENYCRNPDGKRAPWCHTTNSQVRWEYCKIPSCDSSLVSTEQLAPTA--PPE-LTPV
 6  297   HGWSAQTPHTHNRTPENFPCKNLDENYCRNPDGEKAPWCYTTNSQVRWEYCKIPSCESSPVSTEPLDPTA--PPE-LTPV
 7  297   QRWSAQTPQTHNRTPENFPCKNLDENYCRNPDGEKAPWCYTTNSQVRWEYCKIPSCGSSPVSTEQLDPTA--PPE-LTPV
 8  297   QRWSAQSPHKHNRTPENFPCKNLEENYCRNPDGETAPWCYTTDSEVRWDYCKIPSCGSSTTSTEYLDAPV--PPE-QTPV
 9  304   QRWSEQTPHKHNRTPDNFPCKNLEENYCRNPNGEKAPWCYTTNSKVRWEYCTIPSCESSPLSTERMDVPV--PPE-QTPV
10  297   QRWSEQTPHKHNRTPENFPCKNLDENYCRNPDGETAPWCYTTSSETRWEYCNIPSCTSSSVPTEITDASE--PPE-QTPV
11  297   QRWSEQTPHRHNRTPENFPCKNLEENYCRNPDGETAPWCYTTDSQLRWEYCEIPSCESSASPDQ---SDSSVPPEEQTPV
12  297   QRWSEQTPHRHNRTPENFPCKNLEENYCRNPDGETAPWCYTTDSQLRWEYCEIPSCGSSVSPDQ---SDSSVLPE-QTPV
13  297   QRWGEQSPHRHDRTPENYPCKNLDENYCRNPDGEPAPWCFTTNSSVRWEFCKIPDCVSSASETEHSDAPVIVPPE-QTPV
14  297   QRWSEQTPHLHNRTPENFPCKNLDENYCRNPDGESAPWCYTTDSKVRWEHCDIPSCASSPTSVEPLDAPA--PPE-ETPV
15  314   QHWSAQTPHTHNRTPENFPCKNLDENYCRNPDGKRAPWCYTTNSQVRWEYCKIPSCDSSLVSTEQLAPTA--PPE-LTPV
16  239   QRWSEQTPHKHNRTPENFPCKNLDENYCRNPDGESAPWCYTTDSEVRWEHCSIPSCESSPLTLDSLDTPASIPPE-QTPV
```

FIGURE 2/6

```
              361        371        381        391        401        411        421        431
               |          |          |          |          |          |          |          |
 1   374  VQDCYHGDGQSYRGTSSTTTTGKKCQSWSSMTPHRHQKTPENYPNAGLTMNYCRNPDAD-KGPWCFTTDPSVRWEYCNLK
 2   376  VQECYHGNGQSYRGTSSTTITGRKCQSWSSMTPHRHEKTPEHFPEAGLTMNYCRNPDAD-KSPWCYTTDPSVRWEFCNLR
 3   374  VQDCYHGDGQSYRGTSSTTTTGKKCQSWSSMTPHRHQKTPENYPNAGLTMNYCRNPDAD-KGPWCFTTDPSVRWEYCNLK
 4   374  VQDCYHGDGQSYRGTSSTTTTGKKCQSWSSMTPHRHQKTPENYPNAGLTMNYCRNPDAD-KGPWCFTTDPSVRWEYCNLK
 5   364  VQECYHGDGQSYRGTSSTTTTGKKCQSWSSMTPHRHQKTPENYPNAGLTMNYCRNPDAD-KGPWCFTTDPSVRWEYCNLK
 6   374  VQECYHGDGQSYRGTSSTTTTGKKCQSWSSMTPHWHEKTPENFPNAGLTMNYCRNPDAD-KGPWCFTTDPSVRWEYCNLK
 7   374  VQDCYHGDGQSYRGTSSTTTTGKKCQSWSSMTPHWHQKTPENYPDAGLTMNYCRNPDAD-KGPWCFTTDPSVRWEYCNLK
 8   374  AQDCYRGNGESYRGTSSTTITGRKCQSWVSMTPHRHEKTPGNFPENYPNAGLTMNYCRNPDAD-KSPWCYTTDPRVRWEYCNLK
 9   381  PQDCYHGNGQSYRGTSSTTITGKKCQSWSSMTPHWHQKTPEKYPNADLTMNYCRNPDGD-KGPWCYTTDPSVRWEFCNLR
10   374  VQDCYQDKGESYRGTSSITVTGKKCQSWSSMTPHWHQKTPEHFPHRHSKTPENEFPDAGLEMNYCRNPDGD-KGPWCYTTDPSVRWEYCNLK
11   374  VQECYQSDGQSYRGTSSTTITGKKCQSWAAMFPHRHSKTPANFPDAGLEMNYCRNPDNDQRGPWCFTTDPSVRWEYCNLK
12   373  VQECYQGNGKSYRGTSSTTNTGKKCQSWVSMTPHSHSKTPANFPDAGLEMNYCRNPDND-KGPWCFTTDPSVRWEFCNLR
13   376  VQECYQGNGQSYRGTSSTTITGKKCQPWTSMRPHRHSKTPENYPDADLTMNYCRNPDGD-KGPWCYTTDPSVRWEFCNLR
14   374  VQECYQGNGQSYRGTSSTTITGRKCQSWLSMTPHRHQRTPQNYPNADLTMNYCRNPDDD-IRPWCYTTDPSVRWEYCNLR
15   391  VQDCYHGDGQSYRGTSSTTTTGKKCQSWSSMTPHRHQKTPENYPNAGLTMNYCRNPDAD-KGPWCFTTDPSVRWEYCNLK
16   318  VQECYQGNGQTYRGTSSTTITGKKCQPWSSMSPHRHEKTPERFPNAGLTMNYCRNPDGD-KSPWCYTTDPSVRWEFCNLR
```

FIGURE 2/7

```
            441        451        461        471        481        491        501        511
            |          |          |          |          |          |          |          |
1    453   KCSGTEASVVA-PPPVLLPDVETPSEEDCMFGNGKGYRGKRATTVTGTPCQDWAAQEPHRHSIFTPETNPRA-GLEKNY
2    455   KCLDPEASATN-SPAVPQVPSGQEPSASDCMFGNGKGYRGKRATTVMGIPCQEWAAQEPHRHSIFTPETNPQA-GLEKNY
3    453   KCSGTEASVVA-PPPVVQLPNVETPSEEDCMFGNGKGYRGKRATTVTGTPCQDWAAQEPHRHSIFTPETNPRA-GLEKNY
4    453   KCSGTEASVVA-PPPVVQLPNVETPSEEDCMFGNGKGYRGKRATTVTGTPCQDWAAQEPHRHSIFTPETNPRA-GLEKNY
5    443   KCSGTEGSVAA-PPPVVQLPNVETPSEEDCMFGNGKGYRGKRATTVTGTPCQEWAAQEPHSHRIFTPETNPRA-GLEKNY
6    453   KCSGTEGSVVA-PPPVAQLPDAETPSEEDCMFGNGKGYRGKRATTVTGTPCQEWAAQEPHRHSIFTPETNPRA-GLEKNY
7    453   KCSGTEGSVVA-PPPVVQLPNVETPSEEDCMFGNGKRYRGKRATTVAGVPCQEWAAQEPHRHSIFTPETNPRA-GLEKNY
8    453   KCSETEQQVTN-FPAIAQVPSVEDLSE-DCMFGNGKRYRGKRATTVAGVPCQEWAAQEPHHHSIFTPETNPQS-GLERNY
9    460   KCSETPEQV----PAAPQAPGVENPPEADCMIGMGKSYRGKRATTVTGTRCQAWAAQEPHRHSIFTPEANPWA-NLEKNY
10   453   RCSETQQSFSNSSPTDTQVPSVQEPSEPDCMLGIGKGYQGKKATTVTGTPCQGWAAQEPHRHSIFTPQTNPRA-GLEKNY
11   453   RCSETGGSVVE-LPTVSQEPSGPSDSETDCMYGNGKDYRGKRATTVTAAGTPCQEKEYRGKTAVTAAGTPCQEKEYRGKTAVTAAGTPCQEKEYRGKTAVTAAGTPCQEYRGKTAVTAAGTPCQEWAAQEPHRHSIFTPQTNPRA-GLEKNY
12   453   RCSETGGVAE-SAIVPQVPSAPGTSETDCMYGNGKEYRGKTAVTAAGTPCQEWAAQEPHSHRIFTPQTNPRA-GLEKNY
13   455   KCSGTEMSATN-SSPV-QVSSASESSEQDCIIDNGKGYRGTKATTGAGTPCQAWAAQEPHRHSIFTPETNPRA-DLQENY
14   453   RCSEPAASPAA-TVPTAQLPRPEATFEPDCMFGNGKGYRGKRATTADGTPCQGWAAQEPHRHNIFTPETNPRA-GLERNY
15   470   KCSGTEASVVA-PPPVVQLPNVETPSEEDCMFGNGKGYRGKRATTVTGTPCQDWAAQEPHRHSIFTPETNPRA-GLEKNY
16   397   KCLDTEESGTS-SPTVPQVPSGEEPSETDCMFGNGKRYRGKKATTVLGIPCQEWTAQEPHKHSIFTPETNPRAEHLLCPT
17     1   ----------------IRLDCMFGNGKRYRGKKATTVTGTPCQEWAAKEPHSHLIFTPETYPRA-GLEKNY
18     1   -----------APQAPSVENPPEADCMLGIGKGYRGKKATTVAGVPCQEWAAQEPHRHGIFTPETNPRA-GLEKNY
```

FIGURE 2/8

```
                   521        531        541        551        561        571
                    |          |          |          |          |          |
 1  531  CRNPDG--------------DVGGPWCYTTNPRKLYDYCDVPQCAA-PSFDCGKPQVEPKKCPGRVVGGCVAHPHSWPWQ
 2  533  CRNPDG--------------DVNGPWCYTMNQRKLFDYCDVPQCVS-TSFDCGKPQVEPKKCPGRVVGGCVANPHSWPWQ
 3  531  CRNPDG--------------DVGGPWCYTTNPRKLYDYCDVPQCAS-PSFDCGKPQVEPKKCPGRVVGGCVAHPHSWPWQ
 4  531  CRNPDG--------------DVGGPWCYTTNPRKLYDYCDVPQCAS-PSFDCGKPQVEPKKCPGRVVGGCVAHPHSWPWQ
 5  521  CRNPDG--------------DVGGPWCYTTNPRKLFDYCDVPQCAS-PSFDCGKPQVEPKKCPGRVVGGCVAHPHSWPWQ
 6  531  CRNPDG--------------DVGGPWCYTTNPRKHYDYCDVPQCAA-SSFDCGKPQVEPKKCPGRVVGGCVAYPHSWPWQ
 7  531  CRNPDG--------------DEGGPWCYTTNPRKHYDYCDVPQCAS-SSFDCGKPQVEPKKCPGRVVGGCVANAHSWPWQ
 8  530  CRNPDG--------------DDNGPWCYTTNPQKLFDYCDVPQCVT-SSFDCGKPKVEPKKCPARVVGGCVSIPHSWPWQ
 9  535  CRNPDG--------------DVNGPWCYTMNPRKLFDYCDVPQC-E-SSFDCGKPKVEPKKCSGRIVGGCVSKPHSWPWQ
10  532  CRNPDG--------------DVGNPWCYTMNPQKLFDYCDVPQCES-SPFDCGKPKVEPKKCPGRIVGGCVAIAHSWPWQ
11  531  CRNPDG--------------DVNGPWCYTTNPRKLFDYCDIPLCASASSFECCKPQVEPKKCPGRVVGGCVANPHSWPWQ
12  531  CRNPDG--------------DVNGPWCYTMNPRKLFDYCNIPLCASLSSFECGKPKVEPKKCPGRVVGGCVANPHSWPWQ
13  532  CRNPDG--------------DANGPWCYTTNPRKLFDYCDIPHCVSPSSADCGKPKVEPKKCPGRVVGGCVANPHSWPWQ
14  531  CRNPDG--------------DTNGPWCYTMNPRKLYDYCDVPQCASSSYDCGKPQVEPKKCPGRVVGGCVANPHSWPWQ
15  548  CRNPDG--------------DVGGPWCYTTNPRKLYDYCDVPQCAS-PSFDCGKPQVEPKKCPGRVVGGCVAHPHSWPWQ
16  476  CLVPSVPTVFFFFFFLFLDVNGPWCYTTNPRKLFDYCDIPQCAS-GSFDCGKPQVEPKKCPGRVVGGCVANPHSWPWQ
17   55  CRNPDG--------------DVGGPWCYTTNPRKLYDYCDVPQCAS-SSFDCGKPQVEPKKCPGRVVGGCVAHAHSWPWQ
18   65  CRNPDG--------------DVNGPWCYTTNPRKLFDYCDIPQC-E-SSFDCGKPKVEPKKCPARVVGGCVATPHSWPWQ
```

FIGURE 2/9

```
            581             591             601             611             621             631             641
             |               |               |               |               |               |               |
1   596  VSLRTRF-GM------HFCGGTLISPEWVLTAAHCLEKSPRPSSYKVILGAHQEVNLEPHVQEIEVSRLFLEPTRKDIALL
2   598  ISLRTRY-GK------HFCGGTLISPEWVLTAAHCLERSSRPASYKVILGAHKEVNLESDVQEIEVYKLFLEPTRADIALL
3   596  VSLRTRL-GM------HFCGGTLISPEWVLTAAHCLEKSPRPSSYKVILGAHQEVKLEPHVQEIEVSRLFLEPTRTDIALL
4   596  VSLRTSS-NIAGKYWHFCGGTLISPEWVLTAAHCLEKSPRPSSYKVILGAHQEVKLEPHVQEIEVSRLFLEPTRTDIALL
5   586  VSLRTRL-GM------HFCGGTLISPEWVLTAAHCLEKSPRPSSYKVILGAHQEVKLEPHVQEIEVSKMFSEPARADIALL
6   596  ISLRTRL-GM------HFCGGTLISPEWVLTAAHCLEKSSRPSFYKVILGAHREVHLEPHVQEIEVSRLFLEPTRTDIALL
7   596  VSLRTRF-GT------HFCGGTLISPEWVLTAAHCLEKSPRPSSYKVILGAHQEVNLEPHVQEIEVSRLFLEPTRADIALL
8   595  ISLRHRY-GG------HFCGGTLISPEWVLTAKHCLEKSSPSSYKVILGAHEEYHLGEGVQEIDVSKLFKEPSEADIALL
9   599  VSLR-RS-SR------HFCGGTLISPKWVLTAAHCLDNILALSFYKVILGAHNEKVREQSVQEIPVSRLFREPSQADIALL
10  597  ISLRTRF-GR------HFCGGTLISPEWVLTAAHCLERSSRPSTYKVVLGTHHELRLAAGAQQIDVSKLFLEPSRADIALL
11  597  ISLRTRFTGQ------HFCGGTLIAPEWVLTAAHCLEKSSRPEFYKVILGAHEEYIRGSDVQEISVAKLILEPNNRDIALL
12  597  ISLRTRFSGQ------HFCGGTLISPEWVLTAAHCLEKSSRPEFYKVILGAHEERILGSDVQQIAVTKLVLEPNDADIALL
13  598  VSLR-RF-GQ------HFCGGTLIAPEWVLTAAHCLEKFSNPAIYKVVLGAHQETRLERDVQIKGVTKMFLEPYRADIALL
14  597  ISLRTRT-GQ------HFCGGTLISPEWVVTAAHCLEKYPRPSAYRVILGAHKEVNLEDVQDIDVAKLFLEPSRADIALM
15  613  VSLRTRL-GM------HFCGGTLISPEWVLTAAHCLEKSPRPSSYKVILGAHQEVKLEPHVQEIEVSRLFLEPTRTDIALL
16  555  ISLRTRF-GQ------HFCGGTLISPEWVLTAAHCLERSPRPAAYKVILGAHREFNLESDVQEVRLEPHVQEIEVSKLFLEPTHADIALI
17  120  VSLRTRF-GM------HFCGGTLISPEWVLTAAHCLEKSPRPSFYKVILGAHQEVRLEPHVQEIEVSKMFSEPAGADIALL
18  129  VSLRRRS-RE------HFCGGTLISPEWVLTAAHCLDSILGPSFYTVILGAHYEMAREASVQEIPVSRLFLEPSRADIALL
```

FIGURE 2/10

```
              651         661         671         681         691         701         711         721
               |           |           |           |           |           |           |           |
1   670   KLSSPAVITDKVIPACLPSPNYVVADRTECFITGWGETQGTFGAGLLKEAQLPVIENKVCNRYEFLNGRVQSTEL
2   672   KLSSPAVITSKVIPACLPPPNYVVADRTLCYITGWGETQGTYGAGLLKEAQLPVIENKVCNRYEYLNGRVKSTEL
3   670   KLSSPAITTDKVIPACLPSPNYVVADRTECFITGWGETQGTFGAGILKEAQIPVIENKVCNRNEFLNGRVKSTEL
4   675   KLSSPAVITDKVIPACLPSPNYVVADRTECFITGWGETQGTFGAGLLKEAQLPVIENKVCNRNEFLNGRVKSTEL
5   660   KLSSPAIITDKVIPACLPSPNYVVADRTECFITGWGETQGTFGAGLLKEARLPVIENKVCNRYEFLNGTVKTTEL
6   670   KLSSPAIITDKVIPACLPSPNYVVADRTECFITGWGETQGTYGAGLLKEARLPVIENKVCNRYEFLNGRVKSTEL
7   670   KLSSPAVITDKVIPACLPSPNYVVAGRTECFITGWGETQGTFGAGLLKEAQLPVIENKVCNRYEFLNGRVKSTEL
8   669   KLSSPAIITDKVIPACLPTPNYVVADRTACYIIGWGETKGTYGAGLLKEAQLPVIENKVCNRYEFLNGGKVSPNEL
9   672   KLSRPAIITKEVIPACLPPPNYMVAARTECYITGWGETQGTFGEGLLKEAHLPVIENKVCNRNEYLDGRVKPTEL
10  671   KLSRPAIITQNVIPACLPPADYVVANWAECFVTGWGETQDSSNAGVLKEAQLPVIENKVCNRVEYLNNRVKSTEL
11  672   KLSRPAITDKVIPACLPSPNYVMADRTICYITGWGETQGTFGAGRLKEAQLPVIENKVCNRAEYLNNRVKSTEL
12  672   KLSRPAITDNVIPACLPSPNYVVADRTLCYITGWGETKGTPGAGRLKEAQLPVIENKVCNRQELLNGRVRSTEL
13  671   KLSSPAIITDKIIPACLPNSNYMVADRSLCYITGWGETKGTYGAGLLKEAQLPVIENKVCNRFEYLNGRVKSTEL
14  671   KLSSL------------------------EWAWTYGAGLLKEAQLPVIENKVCNREFLNGRVKSTEL
15  687   KLSSPAIITDKVIPACLPSPNYVVADRTECFITGWGETQGTFGAGLLKEAQLPVIENKVCNRNEFLNGKVKSTEL
16  629   KLQSPAVLTSKVIPACLPSPNYVVADRTLCYITGWGETQGTFGVGLLKEAQLPVIENKVCNRYEYLNGKVKSTEL
17  194   KLSSPAIITDKVIPACLPSPNYVVADRTECFITGWGETQGTYGAGLLKEARLPVIENKVCNRYEFLNGRVKSTEL
18  203   KLSSPAVITDEVIPACLPSPNYVVADKTVCYITGWGETQGTFGVGRLKEARLPVIENKVCNRYEYLNGRVKSTEL
```

FIGURE 2/11

```
     731        741        751        761        771        781        791
      |          |          |          |          |          |          |
 1  745 CAGHLAGGTDSCQGDSGGPLVCFEKDKYILQGVTSWGLGCARPNKPGVYVRVSRFVTWIEGVMRNN 810
 2  747 CAGNLAGGTDSCQGDSGGPLVCFEKDKYILQGVTSWGLGCARPNKPGVYVRVSRFVTWIEGIMRNN 812
 3  745 CAGHLAGGTDSCQGDSGGPLVCFEKDKYILQGVTSWGLGCARPNKPGVYVRVSRFVTWIEGVMRNN 810
 4  750 CAGHLAGGTDSCQGDSGGPLVCFEKDKYILQGVTSWGLGCARPNKPGVYVRVSRFVTWIEGVMRNN 815
 5  735 CAGHLAGGTDSCQGDSGGPLVCFEKDKYILQGVTSWGLGCARPNKPGVYVRVSRFVTWIEGVMRNN 800
 6  745 CAGHLAGGTDSCQGDSGGPLVCFEKDKYILQGVTSWGLGCARPNKPGVYVRVSRFVTWIEGVMRNN 810
 7  745 CAGHLAGGTDSCQGDSGGPLVCFEKDKYILQGVTSWGLGCARPNKPGVYVRVSRFVTWIEGVMRNN 810
 8  744 CAGHLAGGTDSCQGDSGGPLVCFEKDKYILQGVTSWGLGCALPNKPGVYVRVSRFVTWIEEIMRRN 809
 9  747 CAGHLIGGTDSCQGDSGGPLVCFEKDKYILQGVTSWGLGCARPNKPGVYVRVSPYVPWIEETMRRN 812
10  746 CAGHLVGGVDSCQGDSGGPLVCFEKDKYILQGVTSWGLGCARPNKPGVYVRVSSFINWIERIMQSN 811
11  747 CAGQLAGGVDSCQGDSGGPLVCFEKDKYILQGVTSWGLGCARPNKPGVYVRVSRFVDWIEREMRNN 812
12  747 CAGHLAGGIDSCQGDSGGPLVCFEKDRYILQGVTSWGLGCARPNKPGVYVRVSRYVNWIEREMRND 812
13  746 CAGHLAGGVDSCQGDSGGPLVCFEKDKYILQGVTSWGLGCARPNKPGVYVRVSRYVSWLQDVMRNN 811
14  715 CAGHLAGGTDSCQGDSGGPLVCFEKDKYILQGVTSWGLGCARPNKPGVYVRVSRFVDWIERTMRNN 780
15  762 CAGNLAGGTDSCQGDSGGPLVCFEKDKYILQGVTSWGLGCARPNKPGVYVRVSRFVTWIEGVMRNN 827
16  704 CAGHLAGGTDSCQGDSGGPLVCFEKDKYILQGVTSWGLGCARPNKPGVYVRVSRFVTWIEEIMRNN 769
17  269 CAGHLAGGTDSCQGDSGGPLVCFEKDKYILQGVTSWGLGCARPNKPGVYVRVSRFVTWIEGVMRNN 334
18  278 CAGDLAGGTDSCQGDSGGPLVCFEKDKYILQGVTSWGLGCARPNKPGVYVRVSTYVPWIEETMRRY 343
```

FIGURE 2/12

PLASMINOGEN AND PLASMIN VARIANTS

CROSS-REFERENCE TO RELATED APPLICATIONS

This application is a 371 of PCT/EP2012/065832 filed Aug. 13, 2012, which claims priority of European Patent Application No. 12161185.9, filed Mar. 26, 2012, and U.S. Provisional Appl. No. 61/522,817, filed Aug. 12, 2011, the contents of all which are incorporated by reference herein in their entireties.

FIELD OF THE INVENTION

The invention relates to variants of plasminogen and plasmin comprising one or more point mutations in the catalytic domain which reduce or prevent autocatalytic destruction of the protease activity of plasmin. Compositions, uses and methods of using said variants of plasminogen and plasmin are also disclosed.

BACKGROUND TO THE INVENTION

Activation of the zymogen plasminogen results in the formation of the fibrinolytically/thrombolytically active serine proteinase plasmin. Activation of endogenous plasminogen can be triggered or enhanced by the administration of a plasminogen activator such as urokinase, streptokinase, staphylokinase or tPA, or any variant thereof. Upon activation, the plasminogen protein is proteolytically cleaved into a heavy chain comprising the 5 kringle domains and a light chain comprising the catalytic domain. Both chains are held together via 2 disulfide bonds. After activation, an autolytic cleavage removes an N-terminal segment from the heavy chain (78 amino acids of human plasmin; 77 amino acids of bovine plasmin) and the bovine plasmin heavy chain can be further autocatalytically cleaved between kringles 3 and 4, hence giving rise to bovine midiplasmin (Christensen et al. 1995, Biochem J 305, 97-102). Activation of plasminogen to plasmin, triggered by the cleavage of the R561-V562 peptide bond in human plasminogen, induces a large conformational change in the light chain, said change resulting in the priming, or activation, of the catalytic triad within said light chain. Bacterial plasminogen activators such as streptokinase and staphylokinase form a complex with plasminogen and, without cleavage of the R561-V562 peptide bond of plasminogen, the catalytic site of plasminogen is activated due to conformational changes upon activator-plasminogen complex formation (plasminogen activation mechanisms are summarized in, e.g., the Introduction section of Terzyan et al. 2004; Proteins 56: 277-284).

Whereas plasminogen activators act as indirect thrombolytic agents, it has alternatively been suggested to use plasmin itself as a direct fibrinolytic/thrombolytic agent. Such direct use is, however, hampered by the fact that plasmin is, like many proteases, subject to autocatalytic proteolytic degradation which follows second order kinetics subject to product inhibition (Jespersen et al. 1986, Thrombosis Research 41, 395-404).

In the early 1960's it was established that plasmin can be stabilized at acidic pH, or alternatively at neutral pH provided an amino acid such as lysine is present. Nevertheless, autolytic cleavage after Lys104, Arg189 and Lys622 (numbering relative to Lys-plasmin) were reported even when plasmin is stored at pH 3.8 (WO01/36608). When plasmin is stored at the even lower pH of 2.2, non-autolytic acid cleavage occurs between Asp-Pro (D-P) at positions Asp62, Asp154 and Asp346 (WO01/36608). This illustrates that pH can be lowered to a point where no apparent autocatylic degradation occurs anymore but at which acid hydrolysis is becoming a factor of destabilization. No information is present in WO01/36608 as to which peptide bonds in plasmin are vulnerable to (autocatalytic) hydrolysis at neutral pH. Known stabilizers of plasmin include glycerol, sufficiently high ionic strength, fibrinogen and ε-aminocaproic acid (EACA), as disclosed by Jespersen et al. (1986, Thromb Res 41, 395-404). Lysine and lysine-derivatives (such as EACA and tranexamic acid) and p-aminomethyl-benzoic acid (PAMBA) are some further known stabilizers (Uehsima et al. 1996, Clin Chim Acta 245, 7-18; Verstraete 1985, Drugs 29, 236-261). U.S. Pat. No. 4,462,980 reported on the formation of plasmin aggregates contributing to plasmin degradation despite storage at acidic conditions. A solution to this problem was provided in U.S. Pat. No. 4,462,980 by means of adding a polyhydroxy compound. Other ways of stabilizing plasmin include the addition of oligopeptidic compounds (e.g. U.S. Pat. No. 5,879,923). Alternatively, the catalytic site of plasmin can be reversibly blocked by means of derivatization, e.g. acylation (EP 0009879). Pegylation of plasmin has also been suggested as a means to stabilize the enzyme (WO 93/15189).

A number of plasmin variants other than truncated forms of plasmin have been described and include a chimeric microplasmin (WO 2004/045558) and variants with a point mutation at the two-chain cleavage site (U.S. Pat. No. 5,087,572) or at a catalytic triad amino acid (Mhashilkar et al. 1993, Proc Natl Acad Sci USA 90, 5374-5377; Wang et al., 2001, J Mol Biol 295, 903-914). Wang et al. (1995, Protein Science 4, 1758-1767 and 1768-1779) reported an extensive series of microplasminogen mutants at amino acid positions 545, 548, 550, 555, 556, 558, 560-564, 585, 740 and 788. A double mutant wherein cysteines at amino acid positions 558 and 566 were substituted for serines was reported by Linde et al. (1998, Eur J Biochem 251, 472-479). Takeda-shitaka et al. (1999, Chem Pharm Bull 47, 322-328) refer to a plasmin variant with reduced activity, the variation involving the substitution of alanine at amino acid position 601 to threonine. All amino acid positions referred to above are relative to Glu-plasminogen starting with Glu at amino acid position 1. A non-cleavable plasminogen variant (cleavage between heavy and light chain impaired) is described in WO 91/08297. Dawson et al. (1994, Biochemistry 33, 12042-12047) describe the reduced affinity for streptokinase of a Glu-plasminogen variant with a Glu instead of Arg at position 719 (R719E). Jespers et al. (1998, Biochemistry 37, 6380-6386) produced in an Ala-scan the series of phage-displayed microplasminogen single-site mutants H569A, R610A, K615A, D660A, Y672A, R712A, R719A, T782A, R789A, and found that arginine at position 719 is key for interaction with staphylokinase; the D660A mutant was not further characterized due to very low expression; only the R719A mutant was additionally produced in soluble form. None of the mutants showed a gross change in proteolytic activity (substrate S-2403). Jespers et al. (1998) also included an active site mutant S741A in their analysis; the crystal structure of this mutant is disclosed in Wang et al. (2000, J Mol Biol 295, 903-914). In further attempts to unravel the streptokinase/plasminogen interaction sites, Terzyan et al. (2004, Proteins 56, 277-284) reported a number of microplasminogen mutants (K698M, D740N, S741A) in an already mutated background (R561A), the latter prohibiting proteolytic activation of plasminogen and thus prohibiting formation of active microplasmin (which would complicate the study of the contact-activation mechanism of the streptokinase-microplasminogen complex). Terzyan et al. (2004) further mention an "inadvertent" triple mutant R561A/H569Y/K698M apparently functionally indifferent from the double mutant R561A/K698M. Wang et al. (2000, Eur J Biochem 267, 3994-4001), in studying streptokinase/plasmin(ogen) interaction, produced a set of microplasminogen (amino acids 530-791 of Glu-plasminogen) mutants in a Cys536Ala and Cys541 Ser background. These mutants include the R561A mutation as described above (Terzyan et al. (2004)) as well as R561A/K698G, R561A/K698A and R561A/K698Q double mutants. In the same C536A/C541S background, single K698G and K698A mutations were introduced also, of which the K698G was not characterized further due to difficulties with purification. The above studies aimed at obtaining a better understanding of the characteristics of the plasminogen/plasmin molecule and did not report any clinical usefulness or benefit or putative clinical advantages of the plasminogen/plasmin mutants. Peisach et al. (1999, Biochemistry 38, 11180-11188) succeeded in determining the crystal structure of microplasminogen containing the M585Q, V673M and M788L mutations.

Nguyen & Chrambach (1981, Preparative Biochem 11, 159-172) reported the presence of "a minor and unidentified protein component" of 10.0 kDa based on reducing SDS-PAGE of a crude commercial preparation of urokinase-activated plasmin (Homolysin). The differences in autolysis of human plasmin depending on pH have been described in detail by Shi &Wu (1988, Thrombosis Research 51, 355-364). Ohyama et al. (2004, Eur J Biochem 271, 809-820) proposed the use of non-lysine analog plasminogen modulators in treatment of cancer due to the enhancement of plasmin autoproteolysis by such compounds which results in the enhanced formation of angiostatins (in the presence of the plasminogen activator urokinase). Table 3 of Ohyama et al. (2004) lists as many as 15 cleavage sites within plasmin subjected to autoproteolyis-enhancing compounds. In discussing their observations in view of prior investigations, it would seem that the autoproteolyis-enhancing compounds are more or less selectively enhancing proteolysis of the B/light-chain whereas minimum degradation of both A/heavy- and B/light-chain was found in the absence of the autoproteolyis-enhancing compounds.

It is clear that none of the above methods/variants solves the problem of providing a plasmin stabilized at the molecular level. The provision of a plasmin variant (or of a corresponding plasminogen variant from which plasmin can be derived) with a catalytic domain intrinsically resistant to autocatalytic degradation would be a significant step forward towards efficient and safe long-term storage as well as towards efficient and safe therapeutic use of plasmin such as in thrombolytic therapy or in the induction of posterior vitreous detachment or vitreous liquefaction in the eye.

SUMMARY OF THE INVENTION

The invention relates to isolated plasminogen variants or plasmin variants obtainable therefrom, or to isolated plasmin variants, or proteolytically active or reversibly inactive derivatives of any of said plasmin variants, wherein said variants are comprising an activation site and a catalytic domain, characterized in that said catalytic domain contains a mutation of one or more amino acids at positions 1 to 4 of the human plasmin catalytic domain or at positions corresponding thereto in a non-human plasmin catalytic domain, wherein said human plasmin catalytic domain is starting with the amino acid valine at position 1 which is the same valine amino acid occurring at position 562 of human Glu-plasminogen. More in particular, if said catalytic domain is mutated at position 1, (i) the amino acid at position −1 relative to the plasmin catalytic domain is an arginine, lysine or other amino acid that maintains functionality of the activation site, (ii) the amino acid at position 24 of the human plasmin catalytic domain, or at the corresponding position of a non-human plasmin catalytic domain, is a methionine, and (iii) the amino acid at position 1 is mutated into an amino acid different from glycine or proline. Alternatively, if said catalytic domain is mutated at positions 1 and 2, the amino acid at position 24 of the human plasmin catalytic domain, or at the corresponding position of a non-human plasmin catalytic domain, is a methionine.

The mutation or mutations in the plasminogen variants, plasmin variants, or plasmin derivatives according to the invention reduce the extent of autoproteolytic degradation of said plasmin variant compared to the extent of autoproteolytic degradation of wild-type plasmin, such as determined with a chromogenic or biological substrate activity assay.

The plasminogen variants, plasmin variants, or plasmin derivatives according to the invention may be Glu-plasminogen or Glu-plasmin, Lys-plasminogen or Lys-plasmin, midiplasminogen or midiplasmin, miniplasminogen or miniplasmin, microplasminogen or microplasmin, deltaplasminogen or deltaplasmin.

The plasminogen variants, plasmin variants, or plasmin derivatives according to the invention are of particular interest for use as a medicament and can optionally by comprised and/or combined in a composition further comprising at least one of a pharmaceutically acceptable diluent, carrier or adjuvant. Such compositions may further comprise one or more of an anticoagulant, a thrombolytic agent, an anti-inflammatory agent, an antiviral agent, an antibacterial agent, an antifungal agent, an anti-angiogenic agent, an anti-mitotic agent, an antihistamine or an anaesthetic.

The invention further relates to methods for screening for autoproteolytically stable plasmin variants, said methods comprising:
(i) providing a plasmin variant according to the invention, and providing wild-type plasmin,
(ii) comparing the autoproteolytic stability of the variant plasmin and wild-type plasmin provided in (i), and
(iii) selecting from (ii) a variant which retains proteolytic activity, and of which autoproteolytic stability is increased relative to the autoproteolyticy stability of wild-type plasmin.

The invention further relates to methods for producing a plasminogen variant according to the invention, said method including the steps of:
(i) introducing a nucleic acid encoding a plasminogen according to the invention in a suitable host cell capable of expressing said plasminogen;
(ii) growing the host cell obtained in (i) under conditions and during a time sufficient for expression of said plasminogen in said host cell; and
(iii) harvesting the plasminogen expressed in (ii).

The invention further relates to methods for producing a plasmin variant according to the invention, said method including the steps of:
(i) introducing a nucleic acid encoding a plasminogen according to the invention in a suitable host cell capable of expressing said plasminogen;
(ii) growing the host cell obtained in (i) under conditions and during a time sufficient for expression of said plasminogen in said host cell;

(iii) harvesting the plasminogen expressed in (ii);

(iv) activating the plasminogen of (iii) to plasmin.

The invention also relates to isolated nucleic acid sequences encoding a plasminogen variant or plasmin variant according to the invention, as well as to recombinant vector comprising such nucleic acid. Host cells transformed with the above nucleic acid or vector likewise are part of the invention.

FIGURE LEGENDS

FIG. 1. Amino acid sequence with double numbering of the amino acid positions of wild-type human Glu-plasminogen (1 to 791) and of the plasmin catalytic domain (1 to 230, amino acid sequence and numbering in bold). Microplasminogen as used for demonstrating the invention starts at amino acid position 543 (numbering relative to Glu-plasminogen). Kringle domains (as derived from the information included in GenBank accession number AAA36451) are boxed and their amino acid sequences typed alternating in normal and italic letters. The catalytic triad amino acids are circled.

FIG. 2. Amino acid sequence alignment of mammalian plasminogen proteins retrieved from GenBank. The sequence alignment was run with the COBALT software (Constraint-based Multiple Alignment Tool; Papadopoulos & Agarwala, Bioinformatics 23:1073-79, 2007) available through the National Center for Biotechnology Information (NCBI) website with default settings. ▼: indication of start of Glu-plasminogen. The amino acid numbering is relative to human plasminogen.

FIG. 3. Picture (×10) of posterior vitreous detachment induced after 5 days post-injection by 30 ng of the microplasmin Val1Ile variant.

DETAILED DESCRIPTION OF THE INVENTION

The current invention is based on the results of studying the effect of point mutations in the plasmin molecule, and more specifically in the catalytic domain of the plasmin molecule, on autoproteolysis. Peptide bonds susceptible to cleavage by plasmin are located at the C-terminus of lysine or arginine (Weinstein & Doolittle, 1972, Biochim Biophys Acta 258, 577-590). Nearly 10% (22 out of 230) of the amino acids of the plasmin catalytic domain (starting at amino acid position 562, a valine, in human Glu-plasminogen) are lysines or arginines. Theoretically all peptide bonds C-terminal of these lysines and arginines, independent of the structure of the amino acid C-terminal of said lysine or arginine, in one plasmin molecule can be proteolytically cleaved by another plasmin molecule. Further theoretically, the mutation of any one or more of these lysines or arginines into a non-lysine non-arginine amino acid would render a plasmin molecule more resistant to autoproteolytic degradation. This theory was proven to be correct, as described in International Patent Publication No. WO2011/004011. Basis for the current invention is the unexpected observation that mutation of a wild-type amino acid located at the N-terminus of the catalytic domain, i.e. of an amino acid at positions 1 to 4 of the catalytic domain, into a non wild-type amino acid, greatly increases the resistance of the resulting mutant plasmin to autoproteolytic degradation, in conjunction with retaining proteolytic capacity by the mutant plasmin.

The invention relates to isolated plasminogen variants or plasmin variants obtainable therefrom, or to isolated plasmin variants, or proteolytically active or reversibly inactive derivatives of any of said plasmin variants, wherein said variants are comprising an activation site and a catalytic domain, characterized in that said catalytic domain contains a mutation of one or more amino acids at positions 1 to 4 of the human plasmin catalytic domain or at positions corresponding thereto in a non-human plasmin catalytic domain, wherein said human plasmin catalytic domain is starting with the amino acid valine at position 1 which is the same valine amino acid occurring at position 562 of human Glu-plasminogen. More in particular, if said catalytic domain is mutated at position 1, (i) the amino acid at position −1 relative to the plasmin catalytic domain is an arginine, lysine or other amino acid that maintains functionality of the activation site, (ii) the amino acid at position 24 of the human plasmin catalytic domain, or at the corresponding position of a non-human plasmin catalytic domain, is a methionine, and (iii) the amino acid at position 1 is mutated into an amino acid different from glycine or proline. Alternatively, if said catalytic domain is mutated at positions 1 and 2, the amino acid at position 24 of the human plasmin catalytic domain, or at the corresponding position of a non-human plasmin catalytic domain, is a methionine. In particular, the above plasminogen variant, plasmin variant, or plasmin derivative comprises the mutation of the amino acid valine at position 1 of the catalytic domain into isoleucine.

The mutation or mutations in the plasminogen variants, plasmin variants, or plasmin derivatives according to the invention reduce the extent of autoproteolytic degradation of said plasmin variant compared to the extent of autoproteolytic degradation of wild-type plasmin, such as determined with a chromogenic or biological substrate activity assay.

Mutations other than the one or those describe above may also be present in the plasmin catalytic domain, as is illustrated in the Examples section.

The plasminogen variants, plasmin variants, or plasmin derivatives according to the invention may be Glu-plasminogen or Glu-plasmin, Lys-plasminogen or Lys-plasmin, midiplasminogen or midiplasmin, miniplasminogen or miniplasmin, microplasminogen or microplasmin, deltaplasminogen or deltaplasmin.

A mutation of an amino acid at a given position into a "non wild-type amino acid", or into an "amino acid different from the natural amino acid", is considered to be a change of the amino acid at said given position of a wild-type plasminogen or plasmin into any amino acid different from the wild-type or natural amino acid at that said given position of that said wild-type plasminogen or plasmin. Some considerations concerning the choice of the mutations follow further.

A person skilled in the art will be able to decide easily into which other amino acid a wild-type amino acid can be mutated. Such decision may, but must not necessarily imply, criteria such as amino acid size, amino acid charge, amino acid polarity, and/or amino acid hydropathy index (see Table 1). Moreover, the availability of the crystal structure of plasminogen and microplasmin (MMDB ID: 12717; PDB ID: 1DDJ; Wang et al., 2001, J Mol Biol 295, 903-914) is of great value in helping identifying the mutant amino acids such that the resulting mutant plasmin or plasminogen molecule retains proteolytic activity. Furthermore, it can be expected that mutation of a wild-type amino acid at a given position [P+/−n], and optionally additionally at one or more of a given position P, P', P", etc., into either one of the amino acids of a given group will yield similar results. Based on Table 1, said given groups can be defined as follows:

hydrophobic aliphatic amino acids: Met, Ile, Leu and Val
hydrophobic aromatic amino acids: Phe
hydrophilic acidic amino acids: Asp, Glu, Asn and Gln
hydrophilic basic amino acids: Arg, Lys and H is
moderately hydrophobic aliphatic amino acids: Gly, Ala, Ser, Thr, Cys, Pro
moderately hydrophobic aromatic amino acids: Tyr and Trp.

Of these, and for the purpose of mutation, Cys and Pro may be less favorable substitute amino acids of wild-type plasmin or plasminogen amino acids due to the creation of possible free thiol-group by a Cys, or due to more extensive disturbance of the protein structure by a Pro. Other amino acid substitutions include the mutation of a wild-type amino acid at a position [P+/−n], and optionally additionally at one or more of a position P, P', P", etc., of a plasmin(ogen) catalytic domain into a non-natural or noncanonical amino acid, or into amino acid analogs, such as norleucine, norvaline, ornithine or citrulline (for more extensive list see, e.g., Hendrickson et al. 2004, Annu Rev Biochem 73, 147-176).

TABLE 1

Characteristics of amino acids.

| Amino Acid | | | Side chain polarity | Side chain charge (at pH 7) | Hydropathy index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Pro line | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

The identification of an amino acid in a non-human plasmin(ogen) sequence which "corresponds to" (i.e. the identification of a "corresponding" amino acid) an amino acid in the human plasmin(ogen) first implies the alignment of both amino acid sequences. Such alignment may require some optimization, such as introduction of minor gaps in one or both of the aligned sequences, to result in the highest identity and homology. Secondly, the amino acid in the non-human plasmin(ogen) aligning with the amino acid in the human plasmin(ogen) is identified and is herein referred to as the "corresponding" amino acid. FIG. 2 herein depicts such an alignment of publicly available mammalian plasminogen protein sequences, and highlights the amino acids of particular interest to the current invention in the human plasminogen sequence (line 1) together with the corresponding amino acids in the non-human plasminogen sequences (lines 2-18). The amino acids P, P', etc., of particular interest are Lys at position 698 (position 137 in the catalytic domain, see FIG. 1), Lys at position 708 (position 147 in the catalytic domain, see FIG. 1) and Arg at position 719 (position 158 in the catalytic domain, see FIG. 1).

"Plasmin", also known as fibrinolysin or lysofibrin, is a serine-type protease which results from the activation of the zymogen plasminogen. Activation is the result of a proteolytic cleavage between amino acids 561 and 562 (numbering relative to human Glu-plasminogen). Plasmin carries a heavy chain comprising 5 kringle domains and a light chain comprising the catalytic domain. Plasminogen can be enriched from blood plasma, e.g., via lysine affinity-chromatography (Deutsch & Mertz, 1970, Science 170, 1095-1096). Truncation of the plasmin molecule (outside and/or inside the plasmin catalytic domain) is possible as long as the catalytic domain remains functional, such truncation thus results in the formation of a "proteolytically active derivative" of plasmin. As such, one or more of the 5 kringle domains can be deleted wholly or partially. Truncated plasmins lacking one or more kringle domains and/or lacking parts of one or more kringle domains therefore are envisaged by the current invention as examples of proteolytically active derivatives of plasmin. Examples of truncated variants of plasmin include, but are not limited to, "midiplasmin", "miniplasmin", "microplasmin", and "delta-plasmin". Midiplasmin is basically lacking kringle domains 1 to 3 (e.g. Christensen et al., 1995, Biochem J 305, 97-102). Miniplasmin was originally obtained by limited digestion of plasmin with elastase and is basically lacking kringle domains 1 to 4 (e.g. Christensen et al., 1979, Biochim Biophys Acta 567, 472-481; Powell & Castellino, 1980, J Biol Chem 255, 5329). Miniplasmin has subsequently been produced recombinantly (WO 2002/050290). Microplasmin was originally obtained by incubation of plasmin at elevated pH and is basically lacking all kringle domains (e.g. WO 89/01336). Whereas the microplasmin obtained from incubation of plasmin at elevated pH is containing the 30-31 carboxy-terminal amino acids of the heavy chain, a recombinantly produced microplasmin variant is containing the 19 carboxy-terminal amino acids of the heavy chain (WO 2002/050290). This illustrates the allowed molecular variability within a given plasmin genus such as the microplasmin genus (e.g. multiple species form the microplasmin genus). Delta-plasmin is a recombinant version of plasmin in which kringle domain 1 is linked directly with the catalytic domain (WO 2005/105990). The above described truncated variants of plasmin are obtained by activation of "midiplasminogen", "miniplasminogen", "microplasminogen" and "delta-plasminogen", respectively. In order to be activatable, a truncated plasminogen needs to comprise a minimum number of amino acids of the linker between the kringle domain (such as kringle 5 domain in miniplasmin) and the catalytic domain, or C-terminal of the catalytic domain in case of a kringle-less truncated plasmin (see, e.g., Wang et al., 1995, Protein Science 4, 1758-1767). In the context of the present invention it may be desired that the plasminogen comprises an "intact activation site", which implies that at least amino acids 561 and 562 (relative to human Glu-plasminogen; or the corresponding amino acids in non-human plasminogen) are such that activation/conversion of plasminogen to plasmin can occur, albeit possibly with different kinetics, as it occurs in wild-type plasmin. As alternative to plasmin or an active truncated variant thereof, an activatable plasminogen or a truncated variant thereof can be used in the context of the current invention (see, e.g. EP 0480906; U.S. Pat. No. 5,304,383; EP 0631786; U.S. Pat. No. 5,520,912; U.S. Pat. No. 5,597,800; U.S. Pat. No. 5,776,452). "Plasminogen" refers to any form of plasminogen e.g. Glu-plasminogen or Lys-plasminogen (starting with Arg at position 68 or Lys at positions 77 or 78). When using activatable plasminogen or an activatable truncated variant thereof, the activation to plasmin may be delayed and will typically occur after contacting it with an organ, tissue or body fluid, i.e. after administration to a subject. In yet another alternative, the plasmin or an active truncated variant thereof can be substituted in the context of the current invention for an activatable plasminogen or an activatable truncated variant thereof in conjunction with a plasminogen activator (such as tissue plasminogen activator (tPA), urokinase, streptokinase or staphylokinase, or any variant thereof; see, e.g. U.S. Pat. No. 6,733,750; U.S. Pat. No. 6,585,972; U.S. Pat. No. 6,899,877; WO 03/33019). In yet a further alternative, a mixture of any of (i) plasmin or derivative thereof, (ii) activatable plasminogen or an activatable derivative thereof, and, optionally (iii) a plasminogen activator can be used in the context of the current invention (see, e.g. US 2004/0081643). In order to ensure stability of the plasmin (or plasminogen), it will generally be stored at lowered temperatures (e.g. +4 degrees Celsius or −20 degrees Celsius). The storage composition may be a stabilizing composition such as a low pH composition (pH 4 or lower; obtained by e.g. 1 mM to 250 mM of an acid such as citric acid, see, e.g. Castellino & Sodetz, 1976, Methods Enzymol 45, 273-286; WO 01/36608; WO 01/36609; WO 01/36611) or a high glycerol content composition (30-50% v/v, e.g., Castellino & Sodetz, 1976, Methods Enzymol 45, 273-286), alternatively in or in conjunction with one or more further stabilizer compositions comprising e.g. an amino acid (e.g. lysine or an analogue thereof such as EACA or tranexamic acid), a sugar (e.g. mannitol) or any stabilizer as known in the art (e.g. dipeptides, WO 97/01631). Further included in the genus "plasmin" is any active derivative thereof (or of an active truncated plasmin variant), or similar derivative of activatable plasminogen (or of activatable truncated variant thereof). Such derivates include e.g. labeled plasmin or plasminogen (or truncated variants thereof) such as $Tc^{99}$-labeled plasmin (Deacon et al., 1980, Br J Radiol 53, 673-677) or pegylated or acylated plasmin or plasminogen (or truncated variants thereof; EP 9879, WO 93/15189). Any other label (radioactive, fluorescent, etc.) may also be used to produce a plasmin or plasminogen derivative. Said derivatives further include hybrid or chimeric plasmin or plasminogen molecules comprising e.g. a truncated plasmin or plasminogen according to the invention fused with e.g. a fibrin-binding molecule (such as kringle 2 of tPA, an apolipoprotein kringle, the finger domain of tPA or fibronectin or the Fab domain of a fibrin-binding antibody).

Comparison of the autoproteolytic resistance (i.e. stability) of wild-type plasmin and of plasmin variants or plasmin derivatives according to the invention can be performed in a similar way as as for comparing proteolytic activity, e.g., in a chromogenic activity assay or a biological substrate assay based on e.g. fibrin, fibrinogen, fibronectin, gelatin, laminin or collagen.

In order to determine autoproteolytic resistance, the autolysis rate constant can be determined. It is envisaged that the plasmin variants according to the invention, including the plasmins obtained from the plasminogen variants according to the invention, or any of the plasmin derivatives according to the invention may be characterized by an autolysis rate constant that is at least 5%, or at least 10%, 15%, 20%, 25%, 30%, 35%, 40%, 45%, 50%, 60%, 70%, 75%, 80%, 90%, 95%, 99% or 99.5% lower than the autolysis rate constant of wild-type plasmin, or, alternatively, by an autolysis rate constant that is at most 95%, or at most 0.5%, 1%, 5%, 10%, 15%, 20%, 25%, 30%, 35%, 40%, 45%, 50%, 60%, 70%, 75%, 80%, or 90% of the autolysis rate constant of wild-type plasmin. In order to determine the indicated percentage, the calculation can be done based on the absolute autolysis rate constant numbers. For example, an autolysis rate constant of 123 $M^{-1}s^{-1}$ was determined for wild-type microplasmin, whereas for the microplasmin variant V1I an autolysis rate constant of 33 $M^{-1}s^{-1}$ was determined (see Examples). The autolysis rate constant of the V1I variant therefore is 26.8% of the autolysis rate constant of wild-type microplasmin.

Further, any of the plasmin variants according to the invention, including the plasmins obtained from the plasminogen variants according to the invention, or derivatives of any of said plasmins may retain proteolytic activity different (higher or lower) from the proteolytic activity of wild-type plasmin, such as determined with e.g. a chromogenic activity assay or a biological substrate assay based on e.g. fibrin, fibrinogen, fibronectin, gelatin, laminin or collagen.

The proteolytic activities of the plasmin variants according to the invention, including the plasmins obtained from the plasminogen variants according to the invention, or any of the plasmin derivatives according to the invention may be compared to the proteolytic activity of wild-type plasmin by means of the catalytic constant $k_{cat}$ which is a measure of the number of substrate molecule each enzyme site converts to product per unit time. Thus, any of the plasmin variants according to the invention, including the plasmins obtained from the plasminogen variants according to the invention, or any of the plasmin derivatives according to the invention may be characterized by a $k_{cat}$ value which is in the range of +100% to −90%, or +50% to −50% of the $k_{cat}$ value of wild-type plasmin, i.e., characterized by a $k_{cat}$ value in the range of 10% to 200%, or 50% to 150% of the $k_{cat}$ value of wild-type plasmin. In order to determine the indicated percentage, the calculation is done on the absolute $k_{cat}$ numbers. For example, wild-type microplasmin has a $k_{cat}$ of 46 $s^{-1}$, whereas the microplasmin variant K137M has a $k_{cat}$ of 36 $s^{-1}$ (see Example 4/Table 3 of WO 2011/004011). The $k_{cat}$ of the K137M variant therefore is 78.3% of the $k_{cat}$ of wild-type microplasmin.

Another way of comparing proteolytic activity of the plasmin variants according to the invention, including the plasmins obtained from the plasminogen variants according to the invention, or any of the plasmin derivatives according to the invention to proteolytic activity of wild-type plasmin includes comparing $k_{cat}/K_m$. Although higher, comparable or slightly lower $k_{cat}/K_m$ values may be preferred, an up to 1000-times or up to 500-times lower $k_{cat}/K_m$ of a plasmin variants according to the invention, including the plasmins obtained from the plasminogen variants according to the invention, or any of the plasmin derivatives according to the invention compared to the $k_{cat}/K_m$ of wild-type plasmin can still be acceptable (see further). By way of example, the $k_{cat}/K_m$ of the V1I microplasmin variant was determined to be $1 \times 10^6$ whereas the $k_{cat}/K_m$ of wild-type plasmin was determined to be $6.9 \times 10^5$ (see Examples), i.e. the $k_{cat}/K_m$ value of V1I microplasmin is 1.45 times higher than the $k_{cat}/K_m$ value of wild-type microplasmin.

Alternatively, any of the plasmin variants according to the invention, including the plasmins obtained from the plasminogen variants according to the invention, or any of the plasmin derivatives according to the invention may be compared to wild-type plasmin by combining autolytic rate constant data and $k_{cat}/K_m$ data. For example, a plasmin variant with a 20-times lower autolytic rate constant compared to wild-type plasmin, and with a 10-times lower $k_{cat}/K_m$ compared to wild-type plasmin will be 2-times better than the wild-type plasmin. Obviously depending on the ultimate use, a very stable plasmin (i.e. no or nearly no autoproteolytic degradation) with low proteolytic activity may be highly desired, e.g., in cases where low but prolonged plasmin activity is desired or even required to achieve the intended clinical effect. Such highly stable plasmin variants with low proteolytic activity would as such virtually equal slow-release formulations without the real need to actually use a slow-release carrier or adjuvant.

Yet another alternative to compare any of the plasmin variants according to the invention, including the plasmins obtained from the plasminogen variants according to the invention, or any of the plasmin derivatives according to the invention may be compared to wild-type plasmin by combining autolytic rate constant data and $k_{cat}$ data.

Further, any of the plasmin variants according to the invention, including the plasmins obtained from the plasminogen variants according to the invention, or any of the plasmin derivatives according to the invention may be characterized by any combination of the above-defined autolysis rate constant, catalytic constant $k_{cat}$ and/or $k_{cat}/K_m$.

Obviously, for any comparative measurements such as described above it is desirable to compare plasmin variants with their closest wild-type plasmin, e.g., to compare a microplasmin variant with wild-type microplasmin, or a miniplasmin variant with wild-type miniplasmin. Furthermore obvious, for any activity measurement, a reversibly inactivated derivative of a plasmin variant according to the invention should first be activated by removing the cause of reversible inactivation (e.g. acylation or non-optimal pH).

Any of the plasminogen variants according to the invention or plasmins obtained therefrom, of the plasmin variants according to the invention may be Glu-plasminogen of Glu-plasmin, Lys-plasminogen or Lys-plasmin, midiplasminogen or midiplasmin, miniplasminogen or miniplasmin, microplasminogen or microplasmin, deltaplasminogen or deltaplasmin.

Many assays exist to determine whether or not a plasmin species is proteolytically active. Easy and straightforward assays are based on the digestion of a chromogenic substrate by plasmin present in a sample; chromogenic substrates include S-2403 (Glu-Phe-Lys-pNA) and S-2251 (Val-Leu-Lys-pNA) which release p-nitroaniline (pNA) upon proteolytic cleavage. The amount of pNA formed can be measured by light absorbance at 405 nm. An alternative assay for determining plasmin activity is a potentiometric assay. Colorimetric (using a chromogenic substrate) and potentiometric assays are described in e.g., Castellino & Sodetz (1976, Methods Enzymol 45, 273-286). A further alternative assay for determining plasmin activity is a caseinolytic assay (e.g., Robbins & Summaria, 1970, Methods Enzymol 19, 184-199; Ruyssen & Lauwers, 1978, Chapter IX—Plasmin, In "Pharmaceutical Enzymes", Story-Scientia, Gent, Belgium, pp. 123-131). Yet another alternative assay for determining plasmin activity is a fibrinolytic assay (e.g., Astrup & Mullertz, 1952, Arch Biochem Biophys 40, 346-351). Further activity assays could be easily designed using other protein substrates. Clearly, such assays may also be used to follow disappearance of plasmin proteolytic activity over time due to autoproteolytic degradation of the enzyme. As an alternative for assessing stability of a plasmin variant or any active truncated variant or derivative thereof of the current invention, said plasmin variant may be incubated in the presence of wild-type plasmin and the resistance of the plasmin variant to digestion by wild-type plasmin can be monitored.

The use of plasmin in the removal of necrotic elements or debris from lesions, wounds, ulcerating wounds (such as ulcerating stitched wounds) etc. has been described in e.g. U.S. Pat. No. 3,208,908. Similarly, topical application of plasmin-comprising therapeutic preparations for the treatment of burns was disclosed in e.g. U.S. Pat. No. 4,122,158. Debridement refers to the removal of dead, damaged and/or infected tissue in order to improve or increase the healing of remaining healthy tissue. Such removal may be obtained by surgical, mechanical or chemical means, or by means of certain species of live maggots that selectively eat necrotic tissue (maggot therapy). Debridement may also be performed using enzymes or may be assisted by enzymes, a process referred to as enzymatic debridement. Debridement is an important aspect in the healing process of burns and other serious wounds and it is used as well in the treatment of some types of snake bites. The application of plasmin (or of any variant or derivative thereof or alternative therefore as described above) in enzymatic debridement (alone or in combination with other types of debridement) is particularly useful in promoting or facilitating wound healing and as an adjunct in surgical procedures such as skin grafting.

A more commonly known use of plasmin (or of any variant or derivative thereof or alternative therefore as described above) relates in general terms to the treatment of (a) pathological deposit(s) of fibrin. Fibrin deposits can result from a wide variety of pathological situations in the body. For example, fibrin-containing blood clots can form in vessels in tissue resulting in deep vein, coronary artery, cerebral artery or retinal vein occlusion or thrombosis. Small accumulations of fibrin precede, and may provide, warning of impending catastrophic thrombosis. Examples include unstable angina pectoris, which is considered a warning of impending coronary thrombosis and transient ischemic attacks, which may precede strokes. Fibrin is furthermore frequently deposited in tissue in association with inflammation associated with many disease processes including infection, autoimmune disease and cancer. Another situation where fibrin is deposited is around abscesses caused by infection with microorganisms. Fibrin deposits are furthermore frequently found associated with certain solid tumors. Fibrin deposition may also occur during the healing of any type of wound, including those resulting from surgical intervention, including e.g. trabeculectomy. Yet another situation of fibrin deposition is the accumulation of fibrin in a retinal vein, which can lead to retinal degeneration, disturbed vision or even loss of vision. The term pathological fibrin deposit further encompasses such deposits as formed or as present in or at the tip of a catheter, catheter device or other implant such as prosthetic vessels and grafts of synthetic, human or animal origin and effectively blocked by an occlusion comprising fibrin. The term "catheter device" refers to any catheter or tube-like device that may enter the body, including arterial catheters, cardiac catheters, central venous catheters, intravenous catheters, peripherally inserted central catheters, pulmonary artery catheters, tunneled central venous catheters and arterio-venous shunts.

Among the various factors encouraging the process of thrombosis, i.e. the formation of a thrombus or hemostatic plug, are: (1) damage to the endothelial cell lining of the affected blood vessel, (2) an increase in the clotting properties of the blood, and (3) stagnation of blood in the affected blood vessel. Thrombosis can start as a very small lump attached to the damaged part of the blood vessel lining. Its presence encourages further thrombosis to occur, and has the effect of causing a slow-down of blood flow by reducing the inner diameter of the vessel. Further growth of the initially small thrombus often leads to total or almost total blockage of the affected blood vessel. If thrombosis takes place in one of the arteries, the tissues supplied by that artery may be deprived of oxygen and nutrition, causing damage or death of the tissue (gangrene). The severity of the damage depends upon the position and size of the thrombosis, the speed at which it grows and whether the affected area has only one artery or is supplied by collateral blood vessels. If the vessel to a vital organ is affected, e.g. the heart or the brain, the person may be severely crippled or die. Sometimes a thrombus may contain infective organisms such as bacteria, and septic thrombosis may occur, with the formation of pus and infection of the surrounding tissues.

Further uses of plasmin (or of any variant or derivative thereof or alternative therefore as described above) include the reduction of the level of circulating fibrinogen (e.g. WO 93/07893) and its use as an α2-antiplasmin inhibitor (reported to reduce the size of cerebral infarct after ischemic stroke; WO 00/18436).

Yet another use of plasmin (or of any variant or derivative thereof or alternative therefore as described above) is related to the induction of posterior vitreous detachment (PVD) and/or vitreous liquefaction in the eye as an alternative for or as adjunct to mechanical vitrectomy (WO 2004/052228; U.S. Pat. No. 6,733,750; U.S. Pat. No. 6,585,972; U.S. Pat. No. 6,899,877; WO 03/33019; WO 2006/122249; WO 2007/047874; U.S. Pat. No. 5,304,118; US 2006/0024349; US 2003/0147877). Vitrectomy and/or vitreous liquefaction is of benefit for a number of eye conditions such as vitreous floaters (motile debris/deposits of vitreous within the normally transparent vitreous humour which can impair vision), retinal detachment (a blinding condition which may be caused by vitreal traction), macular pucker (scar tissue on macula; macula is required for sharp, central vision; macular pucker is also known as epi- or preretinal membrane, cellophane maculopathy, retina wrinkle, surface wrinkling retinopathy, premacular fibrosis, or internal limiting membrane disease), diabetic retinopathy (proliferative or non-proliferative) which may result in vitreal hemorrhage and/or formation of fibrous scar tissue on the retina (which may cause retinal detachment), macular holes (hole in macula causing a blind spot and caused by vitreal traction, injury or a traumatic event), vitreous hemorrhage (caused by diabetic retinopathy, injuries, retinal detachment or retinal tears, subarachnoidal bleedings (Terson syndrome), or blocked vessels), subhyaloid hemorrhage (bleeding under the hyaloid membrane enveloping the vitreous), macular edema (deposition of fluid and protein on or under the macula of the eye) and macular degeneration (starting with the formation of drusen; occurs in dry and wet form; if correlated with age coined age-related macular degeneration). Other eye-applications of plasmin include the maintenance or rescue of a filtering bleb after trabeculectomy surgery (performed to reduce intra-ocular pressure), see e.g. WO 2009/073457.

Another further use of plasmin (or of any variant or derivative thereof or alternative therefore as described above) resides in diagnosis, more particularly appropriately labeled (e.g. Tc$^{99}$-labeled, see above) plasmin (or any variant or derivative thereof or alternative therefore as described above) may be applied for detecting pathological fibrin deposits. When applying a truncated plasmin or plasminogen variant according to the current invention in such diagnosis, care should be taken that said variant still comprises a fibrin-binding site (whether or not from plasmin itself or added to e.g. the plasmin catalytic domain by creating a hybrid molecule).

The plasmin or any variant or derivative thereof or alternative therefore according to the invention may be stored in a pharmaceutically acceptable carrier, diluent or adjuvant. Such carrier, diluent or adjuvant may consist of or comprise an acidic low buffer such as 1-100 mM acetate or citrate. When acidic, the pharmaceutically acceptable carrier, diluent or adjuvant may have a pH of 2.5 to 5.0, such as at pH of 2.5 to 4.0, or such as at a pH of 3.0 to 3.5, or such as a pH of 3.1. Useful acidic compounds include acetic acid, citric acid, hydrochloric acid, lactic acid, malic acid, tartaric acid or benzoic acid. Formic acid may be used but care should be taken that this compound is not inducing proteolytic cleavage at the C-terminus of Asp-residues. The pharmaceutically acceptable carrier, diluent or adjuvant, when either acidic, neutral or basic, may comprise one or more amino acids such as serine, threonine, methionine, glutamine, glycine, isoleucine, valine, alanine, aspartic acid, lysine, histidine or any derivatives or analogues thereof. The pharmaceutically acceptable carrier, diluent or adjuvant may comprise a carbohydrate such as a monosaccharide, disaccharide, polysaccharide or polyhydric alcohol. Examples include sugars such as sucrose, glucose, fructose, lactose, trehalose, maltose and mannose, sugar alcohols such as sorbitol and mannitol and polysaccharides such as dextrins, dextrans, glycogen, starches and celluloses. The pharmaceutically acceptable carrier, diluent or adjuvant may comprise compounds such as glycerol, niacinamide, glucosamine, thiamine, citrulline, inorganic salts (such as sodium chloride, potassium chloride, magnesium chloride, calcium chloride), benzyl alcohol or benzoic acid. The pharmaceutically acceptable carrier, diluents or adjuvant may comprise compounds such as ε-aminocaproic acid (EACA) and/or tranexamic acid (see also above & Background section). Some of these compounds may be used as stabilizer of a plasmin or any variant or derivative thereof or alternative therefore as described above.

In view of the above, another aspect of the invention relates to the isolated plasminogen, plasmin, or any variant or derivative thereof or alternative therefore according to the invention, or a combination of any thereof for use as a medicament.

A further aspect of the invention relates to compositions comprising the isolated plasminogen, plasmin, or any variant or derivative thereof or alternative therefore according to the invention, or a combination of any thereof, and at least one of a pharmaceutically acceptable diluent, carrier or adjuvant. In a further embodiment, said composition may additionally comprise at least one of an anticoagulant, a further thrombolytic agent, an anti-inflammatory agent, an antiviral agent, an antibacterial agent, an antifungal agent, an anti-angiogenic agent, an anti-mitotic agent, an antihistamine or an anaesthetic.

In an embodiment to the above-described two aspects of the invention, the isolated plasminogen, plasmin, or any variant or derivative thereof or alternative therefore according to the invention, or of a combination of any thereof, or the composition according to the invention may be used in any clinically relevant setting such as for treating a pathological fibrin deposit, for inducing posterior vitreous detachment in the eye, for inducing liquefaction of the vitreous in the eye, as adjunct to and facilitating vitrectomy in the eye, for inducing posterior vitreous detachment, for resolving vitreomacular adhesion, for closing macular holes, for enzymatic debridement, for reducing circulating fibrinogen, for reducing α2-antiplasmin levels, or in conjunction with trabeculectomy.

In another embodiment to the above-described two aspects of the invention, the isolated plasminogen, plasmin, or any variant or derivative thereof or alternative therefore according to the invention, or of a combination of any thereof, or the composition according to the invention may be used for prophylactic purposes or in methods for prophylactic treatment. Prophylactic uses include reducing the risk of development of a pathological fibrin deposit in a mammal having an increased risk of developing it (such as an obese mammal, a mammal not doing sufficient physical exercise or a mammal scheduled to undergo a major surgical event or operation). Other prophylactic uses include the induction of posterior vitreous detachment and/or vitreous liquefaction in an apparent healthy eye of a mammal of which the companion eye is/was diagnosed to require induction of posterior vitreous detachment and/or vitreous liquefaction.

Alternatively, the invention relates to methods for treating, dissolving, loosening, macerating, lysing, inducing or promoting lysis of a pathological fibrin deposit in a subject, said methods comprising contacting said fibrin deposit with an effective amount of the isolated plasminogen, plasmin, or any variant or derivative thereof or alternative therefore according to the invention, or of a combination of any thereof, said contacting resulting in the treatment, dissolution, loosening, maceration, lysis, or induction or promotion of lysis of said pathological fibrin deposit.

The invention further relates to methods for inducing posterior vitreous detachment in the eye and/or for inducing liquefaction of the vitreous in the eye, or for facilitating surgical vitrectomy in the eye in a subject, said methods comprising contacting an eye of said subject in need of such treatment with an effective amount of the isolated plasminogen, plasmin, or any variant or derivative thereof or alternative therefore according to the invention or of a combination of any thereof, said contacting resulting in the induction of said posterior vitreous detachment and/or of said liquefaction of the vitreous, or in the facilitation of said surgical vitrectomy.

The invention also relates to methods for enzymatic debridement of injured tissue of a subject, said method comprising contacting said injured tissue with an effective amount of the isolated plasminogen, plasmin, or any variant or derivative thereof or alternative therefore according to the invention, or of a combination of any thereof, said contacting resulting in said enzymatic debridement of said injured tissue.

Other methods of the invention are treating or preventing any other clinically relevant indication, including methods for reducing circulating fibrinogen, or for reducing α2-antiplasmin levels in a subject, said methods comprising contacting a subject in need of such treatment with an effective amount of the isolated plasminogen, plasmin, or any variant or derivative thereof or alternative therefore according to the invention, or of a combination of any thereof, said contacting resulting in said reduction of circulating fibrinogen or of said α2-antiplasmin levels.

In general, the medicament or composition of the invention comprising a plasmin (or any variant or derivative thereof or alternative therefore) according to the invention may, depending on its ultimate use and mode of administration, comprise one or more further active ingredients such as an anticoagulant, a further thrombolytic agent, an anti-inflammatory agent, an antiviral agent, an antibacterial agent, an antifungal agent, an anti-angiogenic agent, an anti-mitotic agent, an antihistamine or anesthetic.

"Anticoagulants" include hirudins, heparins, coumarins, low-molecular weight heparin, thrombin inhibitors, platelet inhibitors, platelet aggregation inhibitors, coagulation factor inhibitors, anti-fibrin antibodies and factor VIII-inhibitors (such as those described in WO 01/04269 and WO 2005/016455).

"Thrombolytic agents" include wild-type plasmin, wild-type plasminogen, urokinase, streptokinase, tissue-type plasminogen activator (tPA or alteplase), urokinase-type plasminogen activator (uPA) and staphylokinase or any variant or derivative of any thereof such as APSAC (anisoylated plasminogen streptokinase activator complex), reteplase, tenecteplase, scuPA (single chain uPA), or a combination of any thereof.

"Anti-inflammatory agents" include steroids (e.g. prednisolone, methylprednisolone, cortisone, hydrocortisone, prednisone, triamcinolone, dexamethasone) and non-steroidal anti-inflammatory agents (NSAIDs; e.g. acetaminophren, ibuprofen, aspirin).

"Antiviral agents" include trifluridine, vidarabine, acyclovir, valacyclovir, famciclovir, and doxuridine.

"Antibacterial agents" or antibiotics include ampicillin, penicillin, tetracycline, oxytetracycline, framycetin, gatifloxacin, gentamicin, tobramycin, bacitracin, neomycin and polymyxin.

"Anti-mycotic/fungistatic/antifungal agents" include fluconazole, amphotericin, clotrimazole, econazole, itraconazole, miconazole, 5-fluorocytosine, ketoconazole and natamycin.

"Anti-angiogenic agents" include antibodies (or fragments thereof) such as anti-VEGF (vascular endothelial growth factor) or anti-PlGF (placental growth factor) antibodies and agents such as macugen (pegaptanib sodium), trypthophanyl-tRNA synthetase (TrpRS), anecortave acetate, combrestatin A4 prodrug, AdPEDF (adenovector capable of expressing pigment epithelium-derived factor), VEGF-trap, inhibitor of VEGF receptor-2, inhibitors of VEGF, PlGF or TGF-13, Sirolimus (rapamycin) and endostatin.

"Anti-mitotic agents" include mitomycin C and 5-fluorouracyl.

"Antihistamine" includes ketitofen fumarate and pheniramine maleate.

"Anesthetics" include benzocaine, butamben, dibucaine, lidocaine, oxybuprocaine, pramoxine, proparacaine, proxymetacaine, tetracaine and amethocaine.

"Contacting", when used herein, means any mode of administration that results in interaction between a composition such as a medicament and the tissue, body fluid, organ, organism, etc. with which said composition is contacted. The interaction between the composition and the tissue, body fluid, organ, organism, etc can occur starting immediately or nearly immediately with the administration of the composition, can occur over an extended time period (starting immediately or nearly immediately with the administration of the composition), or can be delayed relative to the time of administration of the composition.

Any method of contacting a pathological fibrin deposit that provides (either immediately, delayed or over an extended time period) an effective amount of a plasmin (or any variant or derivative thereof or alternative therefore) to such fibrin deposit can be utilized. If such fibrin deposit is associated with a blood clot, the plasmin (or any variant or derivative thereof or alternative therefore) can be delivered intra-arterially, intravenously, or locally (within short distance of the clot or even in the clot) by means of injection and/or infusion and/or a catheter.

When using plasmin (or any variant or derivative thereof or alternative therefore) in enzymatic debridement, it may be included in a gel-like composition capable of being applied topically, or may be applied in liquid form.

Any method of contacting the eye vitreous and/or aqueous humor that provides (either immediately, delayed or over an extended time period) an effective amount of a plasmin (or any variant or derivative thereof or alternative therefore) to the vitreous and/or aqueous humor can be utilized. One method of contacting the vitreous and/or aqueous humor is by one or more intraocular injections directly into the vitreous and/or aqueous humor. Alternatively, said contacting may involve subconjunctival, intramuscular or intravenous injections. A further alternative contacting method involves placing an intra-vitreal implantable device such as OCUSERT® (Alza Corp., Palo Alto, Calif.) or VITRA-SERT® (Bausch & Lomb Inc., Rochester, N.Y.). Contacting the vitreous and/or aqueous humor with an effective amount of a plasmin (or any variant or derivative thereof or alternative therefore) may be in a continuous fashion using a depot, sustained release formulation or any implantable device suitable thereto.

The term "effective amount" refers to the dosing regimen of the medicament according to the invention, in particular of the active ingredient of the medicament according to the invention, i.e., plasmin or an active truncated variant thereof (or any alternative therefore as described above). The effective amount will generally depend on and will need adjustment to the mode of contacting or administration and the condition to be treated. The effective amount of the medicament, more particular its active ingredient, is the amount required to obtain the desired clinical outcome or therapeutic or prophylactic effect without causing significant or unnecessary toxic effects. To obtain or maintain the effective amount, the medicament may be administered as a single dose or in multiple doses. The effective amount may further vary depending on the severity of the condition that needs to be treated or the expected severity of the condition that needs to be prevented; this may depend on the overall health and physical condition of the patient and usually the treating doctor's or physician's assessment will be required to establish what is the effective amount. The effective amount may further be obtained by a combination of different types of administration. The medicament may be administered as a solution (liquid or semi-liquid, e.g., gel-like or in dispersion or suspension, colloidal, in emulsion, nanoparticle suspension) or as a solid (e.g. tablet, minitablet, hard- or soft-shelled capsules).

For purposes of thrombolysis, plasmin dosage and duration of plasmin therapy will typically depend on the size and location of the blood clot as well as on the size, weight and age of the patient. If a clot is venous, treatment with plasmin may continue for days whereas only hours of plasmin therapy may be required if the clot is arterial. A myocardial infarction may be treated with a short single dose treatment whereas conditions such as thrombophlebitis and pulmonary embolism may require longer multiple dose treatment. Prolonged continuous and/or intermittent thrombolytic plasmin therapy may be applied to treat a coronary occlusion or in case of prophylactic therapy in order to reduce the risk of clot formation in subjects known to have an increased risk to develop clot formation. A further factor influencing plasmin dosage includes the circulating levels plasmin inhibitors such as α2-antiplasmin and/or α2-macroglobulin, the initial level of which being patient-dependent. It may be advisable to adjust the plasmin dosage such that no more than 15% of the total circulating α2-antiplasmin is remaining in order to achieve efficient thrombolytic therapy. For the purpose of inducing thrombolysis, a contacting method delivering a plasmin or any variant or derivative thereof or alternative therefore at a short distance proximal to a thrombus may be advantageous as the exposure to serum inhibitors is reduced.

Such contacting method typically involves delivery via a catheter device. For use in thrombolyis, typical plasmin dosages range from 500 microgram/body weight to 10 milligram/kg body weight given as a single bolus or divided over 1 initial bolus injection followed by 1 or more repeat bolus injections. Plasmin may alternatively be administered over an extended time period, e.g. by infusion or by drug delivery micropump. Plasmin dosages for continued administration may range from 1 to 10 mg/kg/hour.

A typical plasmin dosage for inducing posterior vitreous detachment, vitreous liquefaction, clearance of vitreal blood or hemorrhages, or clearance of toxic materials or foreign substances from the vitreous cavity may be in the range of about 0.1 microgram to about 250 microgram per eye per dose, which can be delivered in a diluent or carrier volume of about 50 microliter to about 300 microliter per eye per dose. The diluent or carrier may e.g. be a sterile Balanced Salt Solution (BSS or BSS Plus), a physiologic saline solution or a solution containing 1-10 mM citric acid. In one embodiment plasmin is delivered to the eye in a dose of 125 microgram contained in 0.1 mL diluent or carrier. In the case of planned surgical vitrectomy, said plasmin may be delivered to the eye 15 to 300 minutes, or 15 to 120 minutes prior to the vitrectomy. Alternatively, the purpose of administering plasmin in the eye is to avoid surgical vitrectomy, or to facilitate subsequent surgical vitrectomy in case plasmin treatment itself would not be able to achieve full posterior vitreous detachment. When using plasminogen as an alternative source for plasmin (see "plasmin" definition), up to 250 microgram of plasminogen can be introduced per eye and said plasminogen may be accompanied by up to 2000 IU of urokinase or streptokinase as plasminogen activator or by up to 25 microgram of tPA. When used in the eye, plasmin or plasminogen administration may further be accompanied by administration of a gaseous adjuvant such as air, an expanding gas or liquefiable gas, or mixtures thereof, as long as it is non-toxic to the eye. Other suitable gaseous materials include SF6 (sulfur hexafluoride) and perfluorocarbons, such as C2F6 (hexafluoroethane), C3Fs (octafluoropropane), C4Fs (octafluorocyclobutane), oxygen, nitrogen, carbon dioxide, argon, and other inert gases. The volume of the gaseous material that is introduced into the eye can vary depending on the gaseous material, the patient, and the desired result. For example, the volume of air that is injected into the posterior chamber can range from about 0.5 mL to about 0.9 mL. Other gaseous materials, such as SF6 and perfluorocarbon gases can range from about 0.3 mL to 0.5 mL. Preferably, the gaseous material is introduced into the posterior chamber of the eye in an amount sufficient to compress the vitreous against the posterior hyaloid and form a cavity in the vitreous without damaging the eye. In preferred embodiments, the gaseous adjuvant is introduced into the vitreous to form a cavity that fills about 40% to about 60% of the internal volume of the intraocular cavity.

The above recited dosages are indicative values not meant to be limiting in any way. Said dosages furthermore refer to wild-type plasmin or plasminogen or any active or activatable truncated variant thereof. When using a plasmin with increased stability according to the invention (or any variant or derivative thereof or alternative therefore), and depending on the ultimate stability and residual activity of a plasmin according to the invention, dosages may be similar, higher or lower to obtain the same or better overall clinical effect as obtained with wild-type plasmin. Dosage of a plasmin according to the invention may also depend on the rate of inhibition by endogenous inhibitors such as α2-antiplasmin.

The invention further relates to methods for screening for autoproteolytically stable plasmin variants, said methods comprising:
(i) providing a plasmin variant according to the invention, and providing wild-type plasmin,
(ii) comparing the autoproteolytic stability of the variant plasmin and wild-type plasmin provided in (i), and
(iii) selecting from (ii) a variant which retains proteolytic activity, and of which autoproteolytic stability is increased relative to the autoproteolyticy stability of wild-type plasmin.

The above screening methods may further comprise a step wherein the proteolytic activity of the autoproteolytically stable plasmin variant is determined.

Many products including medicines (here to be understood specifically as user-ready active ingredient, i.e. in the final formulation for administration to a patient) and bulk-stored active ingredients of medicines are usually stored for a considerable amount of time prior to use. It is of interest to extend the shelf-life of products as long as possible. With the shelf-life is meant the time during which the product can be used safely and during which the product retains it potent utility, i.e. its activity in the case of a medicine and/or its active ingredient. Typically, the shelf-life is indicated on a product or its package. Once the shelf-life has expired, the safe and potent utility of a product is no longer guaranteed. A further important aspect in storing products is the storage temperature at which the desired shelf-life can be achieved. For example, the shelf-life of a product stored at +4° C. or average refrigerator temperature may amount to 12 months whereas the shelf-life of the same product stored at −20° C. or average freezer temperature may amount to 36 months. Logistically, however, maintaining a cold chain at freezing temperatures, e.g. −20° C., is much more complex, difficult and expensive than maintaining a cold chain at +4° C. Thus, it may still be attractive to have a shorter, but sufficiently long shelf-life combined with the possibility to store a product at +4° C. The present invention offers a solution for extending, enhancing or increasing the shelf-life or long-term storage stability of plasmin or any active fragment or derivative thereof or of a composition comprising plasmin or any active derivative thereof. The solution resides in making available plasmin variants as herein described, said variants having an enhanced stability, which, intrinsically, increases, enhances or extends their shelf-life.

The invention likewise relates to methods for enhancing long-term storage stability of a plasmin-comprising composition, said methods comprising the step of identifying an autoproteolytically stable plasmin variant capable of being stored over a long time without significant loss of proteolytic activity. For determining long-term stability, a plasmin preparation according to the invention is aliquoted and activity measurements are performed repeatedly during the envisaged storage term. If the envisaged storage term is, e.g., 24 months, activity measurements can be performed, e.g. every month. The allowable loss of proteolytic activity at the end of the envisaged storage term will largely depend on the envisaged clinical application but typically may be no more than e.g. 10% to 15%.

The invention further relates to methods for producing a plasminogen variant according to the invention, said method including the steps of:
(i) introducing a nucleic acid encoding a plasminogen according to the invention in a suitable host cell capable of expressing said plasminogen;
(ii) growing the host cell obtained in (i) under conditions and during a time sufficient for expression of said plasminogen in said host cell; and
(iii) harvesting the plasminogen expressed in (ii).

The invention further relates to methods for producing a plasmin variant according to the invention, said method including the steps of:
(i) introducing a nucleic acid encoding a plasminogen according to the invention in a suitable host cell capable of expressing said plasminogen;
(ii) growing the host cell obtained in (i) under conditions and during a time sufficient for expression of said plasminogen in said host cell;
(iii) harvesting the plasminogen expressed in (ii);
(iv) activating the plasminogen of (iii) to plasmin.

Suitable host cells and methods for expression and production are disclosed in e.g. WO 90/13640 (insect cells), WO 2002/050290 and WO 03/066842 (yeast cells), WO 2008/054592 (bacterial cells/refolding process) and WO 2005/078109 (duckweed transgenic plants or transgenic plant cells).

The invention also relates to (an) isolated nucleic acid sequence(s) encoding a plasminogen variant or plasmin variant according to the invention. The invention also relates to (a) recombinant vector(s) comprising such nucleic acid. The invention also relates to (a) host cell(s) transformed with such nucleic acid or with such recombinant vector.

EXAMPLES

Example 1

Construction and Expression of Plasminogen Variants, and Activation to Plasmin

Expression Vector

The pPICZαA secretion vector purchased from Invitrogen Corporation (Carlsbad, Calif.) was used to direct expression and secretion of recombinant human microplasminogen in *Pichia pastoris*.

This vector contains the secretion signal of the *Saccharomyces cerevisiae* α-factor prepropeptide. A XhoI recognition sequence is present at the COOH-terminus of the α-factor secretion signal, immediately upstream of the Lys-Arg site that is cleaved by Kex2 to remove the secretion signal from the mature protein. This XhoI restriction site may be used to clone the gene of interest flush with the Kex2 cleavage site by synthesizing the gene with the XhoI and Kex2 recognition sites at its the 5' end. The recombinant gene of interest will then be expressed with the native NH$_2$-terminus Engineered immediately downstream from the α-factor secretion signal in the pPICZαA vector is a multiple cloning site with recognition sites for the restriction enzymes EcoRI, SfiI, KpnI, SacII and XbaI to facilitate the cloning of heterologous genes.

Gene Synthesis

To improve expression of human microplasminogen in *Pichia pastoris*, genes encoding the human microplasminogen and variants thereof were synthesized de novo taking into account the preferred codon usage by *Pichia pastoris*.

To design the codon-optimized gene sequence, the human microplasminogen amino acid sequence (SEQ ID NO:19) was imported in the program Gene Designer which is developed by DNA2.0 (Menlo Park, Calif.) and is freely available on the internet. This sequence was backtranslated into DNA sequence using the *Pichia pastoris* codon usage table provided with the program. The nucleotide sequence was then checked manually and adjusted to better fit *Escherichia coli* codon usage (SEQ ID NO:20). In addition, 6-base pair palindromic sequences and nucleotide repetitions were removed when possible. At the 5' end, an XhoI restriction site and the Kex2 cleavage site were added and at the 3' end, an XbaI restriction site was added.

Mutations were introduced by site-directed mutagenesis using the QuikChange II Site Directed Mutagenesis Kit from Agilent (La Jolla, Calif.) in the wild-type microplasminogen sequence or in variant microplasminogen sequences in which specific other amino acid(s) were already changed. The *E. coli* strain TOP10 (Invitrogen) was transformed with the site-directed mutagenesis mixture and ampicillin resistant clones were selected. Sequence determination of the resulting plasmid clones confirmed the precise mutagenesis of the targeted microplasminogen coding region, as well as the absence of unwanted mutations in the coding region.

The following primers were used for site-directed mutagenesis:

```
Val Ile mutation
                         (sense; SEQ ID NO: 21)
GAAGTGTCCAGGTCGTATTGTCGGTGGCTGTGTGGCTC
and
                         (antisense; SEQ ID NO: 22)
GAGCCACACAGCCACCGACAATACGACCTGGACACTTC
```

In a first variant, the valine at position 1 is substituted by an isoleucine. Val1 is encoded by the codon GTT at positions 58-60. The nucleotides GTT (positions 58-60) were changed into ATT, changing Val1 into Ile in the microplasminogen protein (nucleotide sequence is in SEQ ID NO:23 and the deduced amino acid sequence in SEQ ID NO:24).

Expression of Microplasminogen Variants and Activation to Plasmin

The microplasminogen variants and activated microplasmin variants are obtained by following essentially the procedure as outlined in Example 2 of WO 02/50290.

Prior to activation, the microplasminogen mutants were purified by immuno-affinity directly from the *Pichia pastoris* supernatants. A murine anti-human microplasmin antibody (raised in Balb/c mice using microplasmin as antigen; produced by hybridoma cell line 5D10A4, available at ThromboGenics N.V.) was coupled on sepharose beads according to the protocol n° 71500015AD from GE Healthcare. Following this protocol, 7.5 mL of immuno-affinity resin were prepared from 45 mg of antibody and packed in a XK 16/20 column. Crude supernatant 200-400 mL (0.2μ filtered from *Pichia* culture/pH 6.0) was directly loaded on the 5D10A4 affinity column. After a wash step (100 mM KH2PO4, 0.5M NaCl, pH 6.2, 10 column volumes), the microplasminogen variant was eluted with a 0.2M Glycine-HCl, pH 3.0 buffer.

The eluate (fractions 4-6) was neutralized and dialyzed against 25 mM Sodium Phosphate buffer, pH 7.2).

Amino acid sequences and nucleotide sequences of the above described wild-type and variant microplasminogen species are listed hereafter.

```
Wild-type Human microplasminogen
amino acid sequence
                                         SEQ ID NO: 19
APSFDCGKPQVEPKKCPGRVVGGCVAHPHSWPWQVSLRTRFGMHFCGGTL
ISPEWVLTAAHCLEKSPRPSSYKVILGAHQEVNLEPHVQEIEVSRLFLEP
TRKDIALLKLSSPAVITDKVIPACLPSPNYVVADRTECFITGWGETQGTF
GAGLLKEAQLPVIENKVCNRYEFLNGRVQSTELCAGHLAGGTDSCQGDSG
GPLVCFEKDKYILQGVTSWGLGCARPNKPGVYVRVSRFVTWIEGVMRNN Artificial nucleic acid sequence with optimized
codon usage for expression in Pichia. The nucleic
acid sequence encodes the wild-type human
microplasminogen amino acid
sequence of SEQ ID NO: 19
                                         SEQ ID NO: 20
GCACCTTCATTCGACTGTGGTAAGCCTCAGGTCGAACCTAAGAAGTGTCC
AGGTCGTGTTGTCGGTGGCTGTGTGGCTCATCCTCATTCTTGGCCTTGGC
AAGTGTCTCTTAGAACTAGATTTGGTATGCACTTCTGTGGTGGCACCTTG
ATCTCACCTGAATGGGTCTTAACCGCAGCTCATTGTCTGGAGAAGTCACC
ACGTCCATCTTCATACAAGGTCATCCTTGGCGCACATCAGGAAGTCAATC
TTGAGCCTCATGTTCAGGAGATCGAAGTCTCTCGTTTGTTCTTGGAACCA
ACTCGTAAAGACATTGCTCTTCTGAAGCTGTCATCTCCTGCCGTGATTAC
CGACAAGGTAATTCCTGCCTGCTTGCCTAGTCCTAATTACGTCGTTGCCG
ACCGTACCGAATGCTTCATTACTGGTTGGGGTGAGACTCAAGGTACGTTC
GGTGCTGGTCTGTTGAAAGAAGCACAATTACCTGTGATTGAGAACAAGGT
TTGTAACAGATACGAGTTCCTGAATGGTCGTGTTCAGTCCACTGAGTTGT
GTGCAGGTCACCTTGCAGGTGGTACTGATAGTTGTCAAGGTGATTCTGGT
GGACCACTGGTGTGCTTCGAGAAGGATAAGTACATCTTACAAGGTGTTAC
GTCTTGGGGTCTTGGATGTGCTCGTCCTAACAAGCCAGGTGTCTACGTCA
GAGTCTCCAGATTCGTAACTTGGATCGAAGGTGTCATGCGTAACAACTAA Microplasminogen variant with the
ValIle substitution
(mutated codon in bold italics underlined)
                                         SEQ ID NO: 23
GCACCTTCATTCGACTGTGGTAAGCCTCAGGTCGAACCTAAGAAGTGTCC
AGGTCGTATTGTCGGTGGCTGTGTGGCTCATCCTCATTCTTGGCCTTGGC
AAGTGTCTCTTAGAACTAGATTTGGTATGCACTTCTGTGGTGGCACCTTG
ATCTCACCTGAATGGGTCTTAACCGCAGCTCATTGTCTGGAGAAGTCACC
ACGTCCATCTTCATACAAGGTCATCCTTGGCGCACATCAGGAAGTCAATC
TTGAGCCTCATGTTCAGGAGATCGAAGTCTCTCGTTTGTTCTTGGAACCA
ACTCGTAAAGACATTGCTCTTCTGAAGCTGTCATCTCCTGCCGTGATTAC
CGACAAGGTAATTCCTGCCTGCTTGCCTAGTCCTAATTACGTCGTTGCCG
ACCGTACCGAATGCTTCATTACTGGTTGGGGTGAGACTCAAGGTACGTTC
GGTGCTGGTCTGTTGAAAGAAGCACAATTACCTGTGATTGAGAACAAGGT
TTGTAACAGATACGAGTTCCTGAATGGTCGTGTTCAGTCCACTGAGTTGT
GTGCAGGTCACCTTGCAGGTGGTACTGATAGTTGTCAAGGTGATTCTGGT
GGACCACTGGTGTGCTTCGAGAAGGATAAGTACATCTTACAAGGTGTTAC
GTCTTGGGGTCTTGGATGTGCTCGTCCTAACAAGCCAGGTGTCTACGTCA
GAGTCTCCAGATTCGTAACTTGGATCGAAGGTGTCATGCGTAACAACTAA Deduced amino acid sequence of SEQ ID NO: 23
(the introduced amino acid mutation is indicated
in bold/italic and is underlined)
                                         SEQ ID NO: 24
APSFDCGKPQVEPKKCPGRIVGGCVAHPHSWPWQVSLRTRFGMHFCGGTL
ISPEWVLTAAHCLEKSPRPSSYKVILGAHQEVNLEPHVQEIEVSRLFLEP
TRKDIALLKLSSPAVITDKVIPACLPSPNYVVADRTECFITGWGETQGTF
GAGLLKEAQLPVIENKVCNRYEFLNGRVQSTELCAGHLAGGTDSCQGDSG
GPLVCFEKDKYILQGVTSWGLGCARPNKPGVYVRVSRFVTWIEGVMRNN
```

Results:

The $k_{cat}$ and Km values obtained for various microplasmin mutants are listed in Table 1 below.

TABLE 1

| Variant | Kinetic parameters $K_{cat}$/Km (M$^{-1}$s$^{-1}$) | Autolysis rate constant k (M$^{-1}$s$^{-1}$) |
|---|---|---|
| Wild-type | 6.9 × 10$^5$ | 123 |
| V1I | 1.0 × 10$^6$ | 33 |
| V1IK147E | 6.7 × 10$^5$ | 7 |

Example 2

Therapeutic Efficacy of Plasmin Variants in In Vitro or In Vivo Models 2.1 Effect of Plasmin Variants on Cerebral Infarct Size The efficacy of the plasmin variants of the invention in reducing cerebral infarct size can be performed in a murine cerebral infarct model such as described in Example 2 of WO 00/18436, or according to Welsh et al. (1987, J Neurochem 49, 846-851). The beneficial effect of wild-type plasmin on cerebral infarct size was demonstrated in Example 5 of WO 00/18436. A similar experiment is performed with any of the plasmin variants of the invention and the beneficial effect of these plasmin variants is measured and compared to the beneficial effect of wild-type plasmin.

2.2 In Vivo Thrombolytic Activity of Plasmin Variants

The rabbit extracorporeal loop thrombolysis model (Example 6 of WO 02/50290; Hotchkiss et al., 1987, Thromb Haemost 58, 107-Abstract 377), the dog circumflex coronary artery copper coil-induced thrombosis model (Example 8 of WO 02/50290; Bergmann et al., 1983, Science 220, 1181-1183) or the rabbit jugular vein thrombosis model (Collen et al., 1983, J Clin Invest 71, 368-376) can be used to demonstrate in vivo thrombolytic activity of the plasmin variants of the invention. The beneficial effect of wild-type plasmin on thrombolysis was demonstrated with these models as described in Examples 7 and 9 of WO 00/18436 and by Collen et al. (1983). Similar experiments are performed with any of the plasmin variants of the invention and the beneficial effect of these plasmin variants is measured and compared to the beneficial effect of wild-type plasmin.

2.3 In Vitro Thrombolytic Activity of Plasmin Variants

An in vitro model of peripheral arterial occlusion (P AO) is described in Example 6 of WO 01/36609 and the thrombolytic efficacy of wild-type plasmin was demonstrated in this model. A similar experiment is performed with any of the plasmin variants of the invention and the beneficial effect of these plasmin variants on thrombolysis of peripheral arterial occlusions is measured and compared to the beneficial effect of wild-type plasmin.

2.4 Liquefaction of Eye Vitreous and Posterior Vitreous Detachment Induced by Plasmin Variants Example 5 of WO 2004/052228 discloses an assay for determining the efficacy, as well as the efficacy of microplasmin in liquefying the vitreous in post-mortem pig eyes. Example 6 of WO 2004/052228 discloses an assay for determining the efficacy, as well as the efficacy of microplasmin in inducing posterior vitreous detachment (PVD) in human post-mortem eyes. Induction of vitreous liquefaction and PVD by the plasmin variants of the invention is demonstrated in similar post-mortem models.

2.5 In Vivo PVD Induced by Plasmin Variants

Example 7 of WO 2004/052228 discloses an assay for determining the efficacy, as well as the efficacy of microplasmin in inducing PVD in an in vivo feline model. Induction of PVD by the plasmin variants of the invention is demonstrated in a similar in vivo model.

Intravitreal injection of the plasmin variant Val1Ile (V1I)

The effect of V1I microplasmin variant on posterior vitreal detachment (PVD) was examined after intravitreal injection. Briefly, adult C57BL/6 mice were anesthetized with Nembutal (0.6 mg/kg body weight). Intravitreal injections were done using an intraocular injection kit, a 10 µl syringe with 35G beveled needle, and a micro-pump injection apparatus. Each injection of one µl of vehicle containing either wild-type microplasmin or the V1I microplasmin variant at various concentrations was performed under a dissection microscope upon depression of a foot switch. The needle tip was passed through the sclera posterior to the limbus and was positioned to avoid touching the lens. Depression of the foot switch caused the jet of injected product into the midvitreous cavity.

Five days post injection the mice were killed and their eyes were fixed in 1% paraformaldehyde. The eyes were paraffin wax embedded followed by sectioning, and sections were stained with the period acid-Schiff (PAS) reagent. To assess induction of PVD, morphological analysis was performed on the entire eye's sections using light microscopy.

Effect of Intravitreal Injection of Microplasmin and V1I

Representative light microscopy image of V1I injected eyes at 5 days post injections is shown in FIG. 3. PAS stained eye globes sections displayed detachment of the vitreous from the retinal surface following injection of V1I. Microplasmin injected animals demonstrated a _20% induction of PVD as compared to _50% induction of PVD after V1I injection (Table 2). This apparent 2 to 3 times increase in PVD induction was observed at all the concentrations tested.

TABLE 2

PVD induction by V1I and wild-type microplasmin in mouse eyes.

| concentration | incubation time | wild-type microplasmin | | V1I mutant microplasmin | |
|---|---|---|---|---|---|
| | | % PVD | # | % PVD | # |
| 60 ng | 5 days | 0% | (0/4) | 50% | (5/10) |
| | 10 days | 20% | (1/5) | 50% | (5/10) |
| | 30 days | 33% | (1/3) | 50% | (5/10) |
| 30 ng | 5 days | 20% | (1/5) | 78% | (7/9) |
| | 10 days | 0% | (0/5) | 62% | (5/8) |
| | 30 days | 0% | (0/4) | 14% | (1/7) |
| 15 ng | 5 days | 20% | (1/5) | 44% | (4/9) |
| | 10 days | 25% | (1/4) | 60% | (6/10) |
| | 30 days | 0% | (0/4) | 40% | (4/10) |

The invention claimed is:

1. A proteolytically active or reversibly inactivated plasmin variant comprising a plasmin heavy chain and a plasmin light chain, wherein the carboxyl terminus of the plasmin heavy chain amino acid sequence comprises the tripeptide sequence Pro-Gly-Arg of amino acids 559-561 of SEQ ID NO:1 and wherein the plasmin light chain comprises the amino acids 562-791 of SEQ ID NO:1, with the exception that the light chain has:

(a) an amino acid other than valine at position 562 of SEQ ID NO:1;

(b) an amino acid other than valine at position 563 of SEQ ID NO:1;

(c) an amino acid other than glycine at position 564 of SEQ ID NO:1;

(d) an amino acid other than glycine at position 565 of SEQ ID NO:1;

(e) two or more of (i) an amino acid other than valine at position 562 of SEQ ID NO:1; (ii) an amino acid other than valine at position 563 of SEQ ID NO:1; (iii) an amino acid other than glycine at position 564 of SEQ ID NO:1; and (iv) an amino acid other than glycine at position 565 of SEQ ID NO:1; or (f) an amino acid other than valine at position 562 of SEQ ID NO:1 and an amino acid other than lysine at position 708 of SEQ ID NO:1.

2. The plasmin variant of claim 1, wherein the heavy chain comprises:

(a) kringle domain 1;
(b) kringle domain 5; or
(c) kringle domains 4 and 5.

3. The plasmin variant of claim 1, wherein the heavy chain does not comprise kringle domains 1 to 5.

4. The plasmin variant of claim 1, having an autolysis constant that is at most 95% of a wild-type human plasmin autolysis constant.

5. The plasmin variant of claim 1, having an autolysis constant that is at most 80% of a wild-type human plasmin autolysis constant.

6. The plasmin variant of claim 1, having an autolysis constant that is at most 50% of a wild-type human plasmin autolysis constant.

7. The plasmin variant of claim 1, having an autolysis constant that is at most 25% of a wild-type human plasmin autolysis constant.

8. The plasmin variant of claim 1, having a catalytic constant $k_{cat}$ in the range of 10% to 200% of the $k_{cat}$ of wildtype plasmin.

9. The plasmin variant of claim 1, having an autolysis constant that is at most 95% of a wild-type human plasmin autolysis constant and a catalytic constant $k_{cat}$ in the range of 10% to 200% of the $k_{cat}$ of wildtype plasmin.

10. The plasmin variant of claim 1, wherein the plasmin heavy chain comprises amino acids 543-561 of SEQ ID NO:1.

11. The plasmin variant of claim 10, wherein the plasmin light chain has an amino acid other than valine at position 562 of SEQ ID NO:1.

12. The plasmin variant of claim 11, wherein the amino acid at position 562 is an amino acid other than glycine or proline.

13. The plasmin variant of claim 11, wherein the amino acid at position 562 is isoleucine.

14. The plasmin variant of claim 10, wherein the plasmin variant is a Glu-plasmin variant, a Lys-plasmin variant, a midiplasmin variant, a miniplasmin variant, a microplasmin variant, or a delta-plasmin variant.

15. A pharmaceutical composition comprising the plasmin variant of claim 10, and a pharmaceutically acceptable diluent, carrier, or adjuvant.

16. The pharmaceutical composition of claim 15, further comprising at least one of an anticoagulant, a thrombolytic agent, an anti-inflammatory agent, an antiviral agent, an antibacterial agent, an antifungal agent, an anti-angiogenic agent, an anti-mitotic agent, an antihistamine, or an anesthetic.

17. A method of reducing cerebral infarct size in a human subject in need thereof, the method comprising administering to the human subject a therapeutically effective amount of the pharmaceutical composition of claim 15.

18. A method of effecting thrombolysis of peripheral arterial occlusions in a human subject in need thereof, the method comprising administering to the human subject a therapeutically effective amount of the pharmaceutical composition of claim 15.

19. A method of removing necrotic tissue or debris from lesions or wounds in a human subject in need thereof, the method comprising administering to the human subject a therapeutically effective amount of the pharmaceutical composition of claim 15.

20. A method of treatment of pathological deposits of fibrin in a human subject in need thereof, the method comprising administering to the human subject a therapeutically effective amount of the pharmaceutical composition of claim 15.

21. A method of reducing the level of circulating fibrinogen in a human subject in need thereof, the method comprising administering to the human subject a therapeutically effective amount of the pharmaceutical composition of claim 15.

22. A method of inhibiting α2-antiplasmin in a human subject in need thereof, the method comprising administering to the human subject a therapeutically effective amount of the pharmaceutical composition of claim 15.

23. A method of inducing posterior vitreous detachment in a human subject in need thereof, the method comprising administering to the human subject a therapeutically effective amount of the pharmaceutical composition of claim 15.

24. A method of inducing vitreous liquefaction in the eye of a human subject in need thereof, the method comprising administering to the human subject a therapeutically effective amount of the pharmaceutical composition of claim 15.

25. A method of maintaining a filtering bleb after trabeculectomy surgery in a human subject in need thereof, the method comprising administering to the human subject a therapeutically effective amount of the pharmaceutical composition of claim 15.

26. A method of detecting pathological deposits of fibrin in a human subject, the method comprising administering to the human subject a labeled plasmin variant of claim 10 and detecting the labeled plasmin variant in the human subject.

27. An activatable plasminogen variant comprising an amino acid sequence comprising the amino acids at positions 559-791 of SEQ ID NO:1, with the exception that the amino acid sequence has:

(a) an amino acid other than valine at position 562 of SEQ ID NO:1;
(b) an amino acid other than valine at position 563 of SEQ ID NO:1;
(c) an amino acid other than glycine at position 564 of SEQ ID NO:1;
(d) an amino acid other than glycine at position 565 of SEQ ID NO:1;
(e) two or more of (i) an amino acid other than valine at position 562 of SEQ ID NO:1; (ii) an amino acid other than valine at position 563 of SEQ ID NO:1; (iii) an amino acid other than glycine at position 564 of SEQ ID NO:1; and (iv) an amino acid other than glycine at position 565 of SEQ ID NO:1; or
(f) an amino acid other than valine at position 562 of SEQ ID NO:1 and an amino acid other than lysine at position 708 of SEQ ID NO:1.

28. The plasminogen variant of claim 27, wherein the plasminogen variant comprises the amino acids at positions 543-791 of SEQ ID NO:1, with the exception of (a)-(f).

29. The plasminogen variant of claim 28 having an amino acid other than valine at position 562 of SEQ ID NO:1.

30. The plasminogen variant of claim 29, wherein the amino acid at position 562 is an amino acid other than glycine or proline.

31. The plasminogen variant of claim 29, wherein the amino acid at position 562 is isoleucine.

32. The plasminogen variant of claim 28, wherein the plasminogen variant is a Glu-plasminogen variant, a Lys-plasminogen variant, a midiplasminogen variant, a miniplasminogen variant, a microplasminogen variant, or a delta-plasminogen variant.

33. A pharmaceutical composition comprising the plasminogen variant of claim 28, and a pharmaceutically acceptable diluent, carrier, or adjuvant.

34. A proteolytically active or reversibly inactivated plasmin variant comprising a mammalian plasmin heavy chain amino acid sequence and a mammalian plasmin light chain amino acid sequence, wherein the mammalian plasmin heavy chain amino acid sequence carboxyl terminus corresponding to the positions 559-561 of SEQ ID NO:1 is either the tripeptide sequence Pro-Gly-Arg or Pro-Ala-Arg and wherein the mammalian plasmin light chain amino acid sequence has:
   (a) an amino acid other than valine at the position corresponding to 562 of SEQ ID NO:1;
   (b) an amino acid other than valine at the position corresponding to position 563 of SEQ ID NO:1;
   (c) an amino acid other than glycine at the position corresponding to 564 of SEQ ID NO:1;
   (d) an amino acid other than glycine at the position corresponding to 565 of SEQ ID NO:1;
   (e) two or more of (i) an amino acid other than valine at the position corresponding to 562 of SEQ ID NO:1; (ii) an amino acid other than valine at the position corresponding to 563 of SEQ ID NO:1; (iii) an amino acid other than glycine at the position corresponding to 564 of SEQ ID NO:1; and (iv) an amino acid other than glycine at the position corresponding to 565 of SEQ ID NO:1; or
   (f) an amino acid other than valine at position 562 of SEQ ID NO:1 and an amino acid other than lysine at position 708 of SEQ ID NO:1.

35. The plasmin variant of claim 34, wherein the mammalian plasmin light chain has an amino acid other than valine at the position corresponding to position 562 of SEQ ID NO:1.

36. The plasmin variant of claim 35, wherein the amino acid at the position corresponding to position 562 is an amino acid other than glycine or proline.

37. The plasmin variant of claim 35, wherein the amino acid at the position corresponding to position 562 is isoleucine.

38. The plasmin variant of claim 34, wherein the plasmin variant is a Glu-plasmin variant, a Lys-plasmin variant, a midiplasmin variant, a miniplasmin variant, a microplasmin variant, or a delta-plasmin variant.

39. A pharmaceutical composition comprising the plasmin variant of claim 34, and a pharmaceutically acceptable diluent, carrier, or adjuvant.

40. An activatable plasminogen variant comprising a mammalian plasminogen amino acid sequence wherein the mammalian plasminogen comprises as a single chain a plasmin heavy chain and a plasmin light chain, wherein the heavy chain carboxyl terminus corresponding to the positions 559-561 of SEQ ID NO:1 is either the tripeptide sequence Pro-Gly-Arg or the tripeptide sequence Pro-Ala-Arg and wherein the mammalian plasmin light chain amino acid sequence has:
   (a) an amino acid other than valine at the position corresponding to position 562 of SEQ ID NO:1;
   (b) an amino acid other than valine at the position corresponding to position 563 of SEQ ID NO:1;
   (c) an amino acid other than glycine at the position corresponding to position 564 of SEQ ID NO:1;
   (d) an amino acid other than glycine at the position corresponding to position 565 of SEQ ID NO:1;
   (e) two or more of (i) an amino acid other than valine at the position corresponding to position of SEQ ID NO:1; (ii) an amino acid other than valine at the position corresponding to position 563 of SEQ ID NO:1; (iii) an amino acid other than glycine at the position corresponding to position 564 of SEQ ID NO:1; and (iv) an amino acid other than glycine at the position corresponding to position 565 of SEQ ID NO:1; or
   (f) an amino acid other than valine at the position corresponding to 562 of SEQ ID NO:1 and an amino acid other than lysine at the position corresponding to 708 of SEQ ID NO:1.

41. The plasminogen variant of claim 40, wherein the mammalian plasmin light chain has an amino acid other than valine at the position corresponding to position 562 of SEQ ID NO:1.

42. The plasminogen variant of claim 41, wherein the amino acid at the position corresponding to position 562 is an amino acid other than glycine or proline.

43. The plasminogen variant of claim 41, wherein the amino acid at the position corresponding to position 562 is isoleucine.

44. The plasminogen variant of claim 40, wherein the plasminogen variant is a Glu-plasminogen variant, a Lys-plasminogen variant, a midiplasminogen variant, a miniplasminogen variant, a microplasminogen variant, or a delta-plasminogen variant.

45. A pharmaceutical composition comprising the activatable plasminogen variant of claim 40, and a pharmaceutically acceptable diluent, carrier, or adjuvant.

* * * * *

UNITED STATES PATENT AND TRADEMARK OFFICE
CERTIFICATE OF CORRECTION

PATENT NO. : 9,644,196 B2
APPLICATION NO. : 14/238249
DATED : May 9, 2017
INVENTOR(S) : Richard Reinier Zwaal Page 1 of 2

It is certified that error appears in the above-identified patent and that said Letters Patent is hereby corrected as shown below:

In the Claims

Column 101, Line 17 (Claim 34): Between the words "to" and "562" insert -- position --.

Column 101, Line 21 (Claim 34): Between the words "to" and "564" insert -- position --.

Column 101, Line 23 (Claim 34): Between the words "to" and "565" insert -- position --.

Column 101, Line 25 (Claim 34): Between the words "to" and "562" insert -- position --.

Column 101, Line 27 (Claim 34): Between the words "to" and "563" insert -- position --.

Column 101, Line 28 (Claim 34): Between the words "to" and "564" insert -- position --.

Column 101, Line 30 (Claim 34): Between the words "to" and "565" insert -- position --.

Column 101, Line 32 (Claim 34): Between the words "at" and "position" insert -- the position corresponding to --.

Column 101, Line 33 (Claim 34): Between the words "at" and "position" insert -- the position corresponding to --.

Column 102, Line 20 (Claim 40): Between the words "position" and "of" insert -- 562 --.

Column 102, Line 26 (Claim 40): Between the words "to" and "565" insert -- position --.

Signed and Sealed this
Eleventh Day of July, 2017

Joseph Matal
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,644,196 B2

Column 102, Line 28 (Claim 40): Between the words "to" and "562" insert -- position --.

Column 102, Line 29 (Claim 40): Between the words "to" and "708" insert -- position --.

SEQUENCE LISTING

```
<160> NUMBER OF SEQ ID NOS: 24

<210> SEQ ID NO 1
<211> LENGTH: 791
<212> TYPE: PRT
<213> ORGANISM: Homo sapiens

<400> SEQUENCE: 1

Glu Pro Leu Asp Asp Tyr Val Asn Thr Gln Gly Ala Ser Leu Phe Ser
```

```
  1               5                  10                 15
Val Thr Lys Lys Gln Leu Gly Ala Gly Ser Ile Glu Glu Cys Ala Ala
             20                 25                 30
Lys Cys Glu Glu Asp Glu Phe Thr Cys Arg Ala Phe Gln Tyr His
             35                 40                 45
Ser Lys Glu Gln Gln Cys Val Ile Met Ala Glu Asn Arg Lys Ser Ser
 50                 55                 60
Ile Ile Ile Arg Met Arg Asp Val Val Leu Phe Glu Lys Lys Val Tyr
 65                 70                 75                 80
Leu Ser Glu Cys Lys Thr Gly Asn Gly Lys Asn Tyr Arg Gly Thr Met
             85                 90                 95
Ser Lys Thr Lys Asn Gly Ile Thr Cys Gln Lys Trp Ser Ser Thr Ser
            100                105                110
Pro His Arg Pro Arg Phe Ser Pro Ala Thr His Pro Ser Glu Gly Leu
            115                120                125
Glu Glu Asn Tyr Cys Arg Asn Pro Asp Asn Asp Pro Gln Gly Pro Trp
            130                135                140
Cys Tyr Thr Thr Asp Pro Glu Lys Arg Tyr Asp Tyr Cys Asp Ile Leu
145                150                155                160
Glu Cys Glu Glu Glu Cys Met His Cys Ser Gly Glu Asn Tyr Asp Gly
                 165                170                175
Lys Ile Ser Lys Thr Met Ser Gly Leu Glu Cys Gln Ala Trp Asp Ser
             180                185                190
Gln Ser Pro His Ala His Gly Tyr Ile Pro Ser Lys Phe Pro Asn Lys
             195                200                205
Asn Leu Lys Lys Asn Tyr Cys Arg Asn Pro Asp Arg Glu Leu Arg Pro
210                215                220
Trp Cys Phe Thr Thr Asp Pro Asn Lys Arg Trp Glu Leu Cys Asp Ile
225                230                235                240
Pro Arg Cys Thr Thr Pro Pro Ser Ser Gly Pro Thr Tyr Gln Cys
                245                250                255
Leu Lys Gly Thr Gly Glu Asn Tyr Arg Gly Asn Val Ala Val Thr Val
             260                265                270
Ser Gly His Thr Cys Gln His Trp Ser Ala Gln Thr Pro His Thr His
             275                280                285
Asn Arg Thr Pro Glu Asn Phe Pro Cys Lys Asn Leu Asp Glu Asn Tyr
290                295                300
Cys Arg Asn Pro Asp Gly Lys Arg Ala Pro Trp Cys His Thr Thr Asn
305                310                315                320
Ser Gln Val Arg Trp Glu Tyr Cys Lys Ile Pro Ser Cys Asp Ser Ser
             325                330                335
Pro Val Ser Thr Glu Gln Leu Ala Pro Thr Ala Pro Pro Glu Leu Thr
             340                345                350
Pro Val Val Gln Asp Cys Tyr His Gly Asp Gly Gln Ser Tyr Arg Gly
             355                360                365
Thr Ser Ser Thr Thr Thr Thr Gly Lys Lys Cys Gln Ser Trp Ser Ser
370                375                380
Met Thr Pro His Arg His Gln Lys Thr Pro Glu Asn Tyr Pro Asn Ala
385                390                395                400
Gly Leu Thr Met Asn Tyr Cys Arg Asn Pro Asp Ala Asp Lys Gly Pro
                 405                410                415
Trp Cys Phe Thr Thr Asp Pro Ser Val Arg Trp Glu Tyr Cys Asn Leu
             420                425                430
```

```
Lys Lys Cys Ser Gly Thr Glu Ala Ser Val Ala Pro Pro Val
    435                 440                 445

Val Leu Leu Pro Asp Val Glu Thr Pro Ser Glu Glu Asp Cys Met Phe
    450                 455                 460

Gly Asn Gly Lys Gly Tyr Arg Gly Lys Arg Ala Thr Thr Val Thr Gly
465                 470                 475                 480

Thr Pro Cys Gln Asp Trp Ala Ala Gln Glu Pro His Arg His Ser Ile
                485                 490                 495

Phe Thr Pro Glu Thr Asn Pro Arg Ala Gly Leu Glu Lys Asn Tyr Cys
                500                 505                 510

Arg Asn Pro Asp Gly Asp Val Gly Gly Pro Trp Cys Tyr Thr Thr Asn
                515                 520                 525

Pro Arg Lys Leu Tyr Asp Tyr Cys Asp Val Pro Gln Cys Ala Ala Pro
                530                 535                 540

Ser Phe Asp Cys Gly Lys Pro Gln Val Glu Pro Lys Lys Cys Pro Gly
545                 550                 555                 560

Arg Val Val Gly Gly Cys Val Ala His Pro His Ser Trp Pro Trp Gln
                565                 570                 575

Val Ser Leu Arg Thr Arg Phe Gly Met His Phe Cys Gly Gly Thr Leu
                580                 585                 590

Ile Ser Pro Glu Trp Val Leu Thr Ala Ala His Cys Leu Glu Lys Ser
                595                 600                 605

Pro Arg Pro Ser Ser Tyr Lys Val Ile Leu Gly Ala His Gln Glu Val
                610                 615                 620

Asn Leu Glu Pro His Val Gln Glu Ile Glu Val Ser Arg Leu Phe Leu
625                 630                 635                 640

Glu Pro Thr Arg Lys Asp Ile Ala Leu Leu Lys Leu Ser Ser Pro Ala
                645                 650                 655

Val Ile Thr Asp Lys Val Ile Pro Ala Cys Leu Pro Ser Pro Asn Tyr
                660                 665                 670

Val Val Ala Asp Arg Thr Glu Cys Phe Ile Thr Gly Trp Gly Glu Thr
                675                 680                 685

Gln Gly Thr Phe Gly Ala Gly Leu Leu Lys Glu Ala Gln Leu Pro Val
                690                 695                 700

Ile Glu Asn Lys Val Cys Asn Arg Tyr Glu Phe Leu Asn Gly Arg Val
705                 710                 715                 720

Gln Ser Thr Glu Leu Cys Ala Gly His Leu Ala Gly Gly Thr Asp Ser
                725                 730                 735

Cys Gln Gly Asp Ser Gly Gly Pro Leu Val Cys Phe Glu Lys Asp Lys
                740                 745                 750

Tyr Ile Leu Gln Gly Val Thr Ser Trp Gly Leu Gly Cys Ala Arg Pro
                755                 760                 765

Asn Lys Pro Gly Val Tyr Val Arg Val Ser Arg Phe Val Thr Trp Ile
                770                 775                 780

Glu Gly Val Met Arg Asn Asn
785                 790

<210> SEQ ID NO 2
<211> LENGTH: 812
<212> TYPE: PRT
<213> ORGANISM: Canis familiaris

<400> SEQUENCE: 2

Met Glu His Lys Glu Val Val Leu Leu Leu Leu Leu Phe Leu Lys Ser
```

-continued

```
1               5                   10                  15
Gly His Gly Ser Leu Leu Asp Asp Tyr Val Asn Thr Gln Gly Ala Ser
                20                  25                  30

Val Phe Ser Leu Thr Lys Lys Gln Leu Ser Val Gly Ser Ile Glu Glu
                35                  40                  45

Cys Ala Ala Lys Cys Glu Glu Glu Thr Gly Phe Ile Cys Arg Ser Phe
                50                  55                  60

Gln Tyr His Ser Lys Glu Gln Gln Cys Val Ile Met Pro Glu Asn Ser
65                  70                  75                  80

Lys Ser Ser Ile Val Phe Arg Met Arg Asp Val Phe Leu Phe Glu Lys
                85                  90                  95

Arg Ile Tyr Leu Ser Glu Cys Lys Thr Gly Asn Gly Lys Thr Tyr Arg
                100                 105                 110

Gly Thr Met Ala Lys Thr Lys Asn Asp Val Ala Cys Gln Lys Trp Ser
                115                 120                 125

Asp Asn Ser Pro His Lys Pro Asn Tyr Thr Pro Glu Lys His Pro Leu
                130                 135                 140

Glu Gly Leu Glu Glu Asn Tyr Cys Arg Asn Pro Asp Asn Asp Glu Asn
145                 150                 155                 160

Gly Pro Trp Cys Tyr Thr Thr Asn Pro Asp Val Arg Phe Asp Tyr Cys
                165                 170                 175

Asn Ile Pro Glu Cys Glu Glu Cys Met His Cys Ser Gly Glu Asn
                180                 185                 190

Tyr Glu Gly Lys Ile Ser Lys Thr Lys Ser Gly Leu Glu Cys Gln Ala
                195                 200                 205

Trp Asn Ser Gln Thr Pro His Ala His Gly Tyr Ile Pro Ser Lys Phe
                210                 215                 220

Pro Ser Lys Asn Leu Lys Met Asn Tyr Cys Arg Asn Pro Asp Gly Glu
225                 230                 235                 240

Pro Arg Pro Trp Cys Phe Thr Met Asp Pro Asn Lys Arg Trp Glu Phe
                245                 250                 255

Cys Asp Ile Pro Arg Cys Thr Thr Pro Pro Pro Ser Gly Pro Thr
                260                 265                 270

Tyr Gln Cys Leu Lys Gly Arg Gly Glu Ser Tyr Arg Gly Lys Val Ser
                275                 280                 285

Val Thr Val Ser Gly His Thr Cys Gln His Trp Ser Glu Gln Thr Pro
                290                 295                 300

His Lys His Asn Arg Thr Pro Glu Asn Phe Pro Cys Lys Asn Leu Asp
305                 310                 315                 320

Glu Asn Tyr Cys Arg Asn Pro Asp Gly Glu Thr Ala Pro Trp Cys Tyr
                325                 330                 335

Thr Thr Asn Ser Glu Val Arg Trp Glu His Cys Gln Ile Pro Ser Cys
                340                 345                 350

Glu Ser Ser Pro Ile Thr Thr Glu Tyr Leu Asp Ala Pro Ala Ser Val
                355                 360                 365

Pro Pro Glu Gln Thr Pro Val Val Gln Glu Cys Tyr His Gly Asn Gly
                370                 375                 380

Gln Ser Tyr Arg Gly Thr Ser Ser Thr Thr Ile Thr Gly Arg Lys Cys
385                 390                 395                 400

Gln Ser Trp Ser Ser Met Thr Pro His Arg His Glu Lys Thr Pro Glu
                405                 410                 415

His Phe Pro Glu Ala Gly Leu Thr Met Asn Tyr Cys Arg Asn Pro Asp
                420                 425                 430
```

Ala Asp Lys Ser Pro Trp Cys Tyr Thr Thr Asp Pro Ser Val Arg Trp
            435                 440                 445

Glu Phe Cys Asn Leu Arg Lys Cys Leu Asp Pro Glu Ala Ser Ala Thr
    450                 455                 460

Asn Ser Pro Ala Val Pro Gln Val Pro Ser Gly Gln Glu Pro Ser Ala
465                 470                 475                 480

Ser Asp Cys Met Phe Gly Asn Gly Lys Gly Tyr Arg Gly Lys Lys Ala
                485                 490                 495

Thr Thr Val Met Gly Ile Pro Cys Gln Glu Trp Ala Ala Gln Glu Pro
            500                 505                 510

His Arg His Ser Ile Phe Thr Pro Glu Thr Asn Pro Gln Ala Gly Leu
        515                 520                 525

Glu Lys Asn Tyr Cys Arg Asn Pro Asp Gly Asp Val Asn Gly Pro Trp
    530                 535                 540

Cys Tyr Thr Met Asn Gln Arg Lys Leu Phe Asp Tyr Cys Asp Val Pro
545                 550                 555                 560

Gln Cys Val Ser Thr Ser Phe Asp Cys Gly Lys Pro Gln Val Glu Pro
                565                 570                 575

Lys Lys Cys Pro Gly Arg Val Val Gly Gly Cys Val Ala Asn Pro His
            580                 585                 590

Ser Trp Pro Trp Gln Ile Ser Leu Arg Thr Arg Tyr Gly Lys His Phe
        595                 600                 605

Cys Gly Gly Thr Leu Ile Ser Pro Glu Trp Val Leu Thr Ala Ala His
    610                 615                 620

Cys Leu Glu Arg Ser Ser Arg Pro Ala Ser Tyr Lys Val Ile Leu Gly
625                 630                 635                 640

Ala His Lys Glu Val Asn Leu Glu Ser Asp Val Gln Glu Ile Glu Val
                645                 650                 655

Tyr Lys Leu Phe Leu Glu Pro Thr Arg Ala Asp Ile Ala Leu Leu Lys
            660                 665                 670

Leu Ser Ser Pro Ala Val Ile Thr Ser Lys Val Ile Pro Ala Cys Leu
        675                 680                 685

Pro Pro Pro Asn Tyr Val Val Ala Asp Arg Thr Leu Cys Tyr Ile Thr
    690                 695                 700

Gly Trp Gly Glu Thr Gln Gly Thr Tyr Gly Ala Gly Leu Leu Lys Glu
705                 710                 715                 720

Ala Gln Leu Pro Val Ile Glu Asn Lys Val Cys Asn Arg Tyr Glu Tyr
                725                 730                 735

Leu Asn Gly Arg Val Lys Ser Thr Glu Leu Cys Ala Gly Asn Leu Ala
            740                 745                 750

Gly Gly Thr Asp Ser Cys Gln Gly Asp Ser Gly Gly Pro Leu Val Cys
        755                 760                 765

Phe Glu Lys Asp Lys Tyr Ile Leu Gln Gly Val Thr Ser Trp Gly Leu
    770                 775                 780

Gly Cys Ala Arg Pro Asn Lys Pro Gly Val Tyr Val Arg Val Ser Arg
785                 790                 795                 800

Phe Val Thr Trp Ile Glu Gly Ile Met Arg Asn Asn
                805                 810

<210> SEQ ID NO 3
<211> LENGTH: 810
<212> TYPE: PRT
<213> ORGANISM: Pan troglodytes

```
<400> SEQUENCE: 3

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Lys Glu Phe Thr Cys Arg Ala Phe
    50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
        115                 120                 125

Ser Thr Ser Pro His Arg Pro Arg Phe Ser Pro Ala Thr His Pro Ser
    130                 135                 140

Glu Gly Leu Glu Glu Asn Tyr Cys Arg Asn Pro Asp Asn Asp Pro Gln
145                 150                 155                 160

Gly Pro Trp Cys Tyr Thr Thr Asp Pro Glu Lys Arg Tyr Asp Tyr Cys
                165                 170                 175

Asp Ile Leu Glu Cys Glu Glu Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Gly Glu
225                 230                 235                 240

Leu Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270

Tyr Gln Cys Leu Lys Gly Thr Gly Glu Asn Tyr Arg Gly Asn Val Ala
        275                 280                 285

Val Thr Val Ser Gly His Thr Cys Gln His Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Lys Arg Ala Pro Trp Cys His
                325                 330                 335

Thr Thr Asn Ser Gln Val Arg Trp Glu Tyr Cys Lys Ile Pro Ser Cys
            340                 345                 350

Asp Ser Ser Leu Val Ser Thr Glu Gln Leu Ala Pro Thr Ala Pro Pro
        355                 360                 365

Glu Leu Thr Pro Val Val Gln Asp Cys Tyr His Gly Asp Gly Gln Ser
    370                 375                 380

Tyr Arg Gly Thr Ser Ser Thr Thr Thr Thr Gly Lys Lys Cys Gln Ser
385                 390                 395                 400

Trp Ser Ser Met Thr Pro His Arg His Gln Lys Thr Pro Glu Asn Tyr
                405                 410                 415
```

```
Pro Asn Ala Gly Leu Thr Met Asn Tyr Cys Arg Asn Pro Asp Ala Asp
            420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
    450                 455                 460

Pro Pro Val Val Gln Leu Pro Asn Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
    530                 535                 540

Thr Thr Asn Pro Arg Lys Leu Tyr Asp Tyr Cys Asp Val Pro Gln Cys
545                 550                 555                 560

Ala Ser Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
            580                 585                 590

Pro Trp Gln Val Ser Leu Arg Thr Arg Leu Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Pro Arg Pro Ser Ser Tyr Lys Val Ile Leu Gly Ala His
625                 630                 635                 640

Gln Glu Val Lys Leu Glu Pro His Val Gln Glu Ile Glu Val Ser Arg
                645                 650                 655

Leu Phe Leu Glu Pro Thr Arg Thr Asp Ile Ala Leu Leu Lys Leu Ser
            660                 665                 670

Ser Pro Ala Ile Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Asn Glu Phe Leu Asn
                725                 730                 735

Gly Arg Val Lys Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800

Thr Trp Ile Glu Gly Val Met Arg Asn Asn
                805                 810

<210> SEQ ID NO 4
<211> LENGTH: 815
```

```
<212> TYPE: PRT
<213> ORGANISM: Pan troglodytes

<400> SEQUENCE: 4
```

| | | | | | | | | | | | | | | |
|---|---|---|---|---|---|---|---|---|---|---|---|---|---|---|
| Met | Glu | His | Lys | Glu | Val | Val | Leu | Leu | Leu | Phe | Leu | Lys | Ser |
| 1 | | | | 5 | | | | | 10 | | | | 15 |
| Gly | Gln | Gly | Glu | Pro | Leu | Asp | Asp | Tyr | Val | Asn | Thr | Gln | Gly | Ala | Ser |
| | | | 20 | | | | | 25 | | | | | 30 | | |
| Leu | Phe | Ser | Val | Thr | Lys | Lys | Gln | Leu | Gly | Ala | Gly | Ser | Ile | Glu | Glu |
| | | | 35 | | | | | 40 | | | | | 45 | | |
| Cys | Ala | Ala | Lys | Cys | Glu | Glu | Asp | Lys | Glu | Phe | Thr | Cys | Arg | Ala | Phe |
| | | | 50 | | | | | 55 | | | | | 60 | | |
| Gln | Tyr | His | Ser | Lys | Glu | Gln | Gln | Cys | Val | Ile | Met | Ala | Glu | Asn | Arg |
| 65 | | | | | 70 | | | | | 75 | | | | | 80 |
| Lys | Ser | Ser | Ile | Ile | Ile | Arg | Met | Arg | Asp | Val | Val | Leu | Phe | Glu | Lys |
| | | | | 85 | | | | | 90 | | | | | 95 | |
| Lys | Val | Tyr | Leu | Ser | Glu | Cys | Lys | Thr | Gly | Asn | Gly | Lys | Asn | Tyr | Arg |
| | | | 100 | | | | | 105 | | | | | 110 | | |
| Gly | Thr | Met | Ser | Lys | Thr | Lys | Asn | Gly | Ile | Thr | Cys | Gln | Lys | Trp | Ser |
| | | | 115 | | | | | 120 | | | | | 125 | | |
| Ser | Thr | Ser | Pro | His | Arg | Pro | Arg | Phe | Ser | Pro | Ala | Thr | His | Pro | Ser |
| | 130 | | | | | 135 | | | | | 140 | | | | |
| Glu | Gly | Leu | Glu | Glu | Asn | Tyr | Cys | Arg | Asn | Pro | Asp | Asn | Asp | Pro | Gln |
| 145 | | | | | 150 | | | | | 155 | | | | | 160 |
| Gly | Pro | Trp | Cys | Tyr | Thr | Thr | Asp | Pro | Glu | Lys | Arg | Tyr | Asp | Tyr | Cys |
| | | | | 165 | | | | | 170 | | | | | 175 | |
| Asp | Ile | Leu | Glu | Cys | Glu | Glu | Glu | Cys | Met | His | Cys | Ser | Gly | Glu | Asn |
| | | | 180 | | | | | 185 | | | | | 190 | | |
| Tyr | Asp | Gly | Lys | Ile | Ser | Lys | Thr | Met | Ser | Gly | Leu | Glu | Cys | Gln | Ala |
| | | | 195 | | | | | 200 | | | | | 205 | | |
| Trp | Asp | Ser | Gln | Ser | Pro | His | Ala | His | Gly | Tyr | Ile | Pro | Ser | Lys | Phe |
| | 210 | | | | | 215 | | | | | 220 | | | | |
| Pro | Asn | Lys | Asn | Leu | Lys | Lys | Asn | Tyr | Cys | Arg | Asn | Pro | Asp | Gly | Glu |
| 225 | | | | | 230 | | | | | 235 | | | | | 240 |
| Leu | Arg | Pro | Trp | Cys | Phe | Thr | Thr | Asp | Pro | Asn | Lys | Arg | Trp | Glu | Leu |
| | | | | 245 | | | | | 250 | | | | | 255 | |
| Cys | Asp | Ile | Pro | Arg | Cys | Thr | Thr | Pro | Pro | Ser | Ser | Gly | Pro | Thr |
| | | | 260 | | | | | 265 | | | | | 270 | | |
| Tyr | Gln | Cys | Leu | Lys | Gly | Thr | Gly | Glu | Asn | Tyr | Arg | Gly | Asn | Val | Ala |
| | | | 275 | | | | | 280 | | | | | 285 | | |
| Val | Thr | Val | Ser | Gly | His | Thr | Cys | Gln | His | Trp | Ser | Ala | Gln | Thr | Pro |
| | 290 | | | | | 295 | | | | | 300 | | | | |
| His | Thr | His | Asn | Arg | Thr | Pro | Glu | Asn | Phe | Pro | Cys | Lys | Asn | Leu | Asp |
| 305 | | | | | 310 | | | | | 315 | | | | | 320 |
| Glu | Asn | Tyr | Cys | Arg | Asn | Pro | Asp | Gly | Lys | Arg | Ala | Pro | Trp | Cys | His |
| | | | | 325 | | | | | 330 | | | | | 335 | |
| Thr | Thr | Asn | Ser | Gln | Val | Arg | Trp | Glu | Tyr | Cys | Lys | Ile | Pro | Ser | Cys |
| | | | 340 | | | | | 345 | | | | | 350 | | |
| Asp | Ser | Ser | Leu | Val | Ser | Thr | Glu | Gln | Leu | Ala | Pro | Thr | Ala | Pro | Pro |
| | | | 355 | | | | | 360 | | | | | 365 | | |
| Glu | Leu | Thr | Pro | Val | Val | Gln | Asp | Cys | Tyr | His | Gly | Asp | Gly | Gln | Ser |
| | 370 | | | | | 375 | | | | | 380 | | | | |
| Tyr | Arg | Gly | Thr | Ser | Ser | Thr | Thr | Thr | Thr | Gly | Lys | Lys | Cys | Gln | Ser |
| 385 | | | | | 390 | | | | | 395 | | | | | 400 |

```
Trp Ser Ser Met Thr Pro His Arg His Gln Lys Thr Pro Glu Asn Tyr
            405                 410                 415

Pro Asn Ala Gly Leu Thr Met Asn Tyr Cys Arg Asn Pro Asp Ala Asp
        420                 425                 430

Lys Gly Pro Trp Cys Phe Thr Thr Asp Pro Ser Val Arg Trp Glu Tyr
        435                 440                 445

Cys Asn Leu Lys Lys Cys Ser Gly Thr Glu Ala Ser Val Val Ala Pro
450                 455                 460

Pro Pro Val Val Gln Leu Pro Asn Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Asp Trp Ala Ala Gln Glu Pro His Arg
            500                 505                 510

His Ser Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
530                 535                 540

Thr Thr Asn Pro Arg Lys Leu Tyr Asp Tyr Cys Asp Val Pro Gln Cys
545                 550                 555                 560

Ala Ser Pro Ser Phe Asp Cys Gly Lys Pro Gln Val Glu Pro Lys Lys
                565                 570                 575

Cys Pro Gly Arg Val Val Gly Gly Cys Val Ala His Pro His Ser Trp
                580                 585                 590

Pro Trp Gln Val Ser Leu Arg Thr Ser Ser Asn Ile Ala Gly Lys Tyr
        595                 600                 605

Trp His Phe Cys Gly Gly Thr Leu Ile Ser Pro Glu Trp Val Leu Thr
        610                 615                 620

Ala Ala His Cys Leu Glu Lys Ser Pro Arg Pro Ser Ser Tyr Lys Val
625                 630                 635                 640

Ile Leu Gly Ala His Gln Glu Val Lys Leu Glu Pro His Val Gln Glu
                645                 650                 655

Ile Glu Val Ser Arg Leu Phe Leu Glu Pro Thr Arg Thr Asp Ile Ala
            660                 665                 670

Leu Leu Lys Leu Ser Ser Pro Ala Ile Ile Thr Asp Lys Val Ile Pro
        675                 680                 685

Ala Cys Leu Pro Ser Pro Asn Tyr Val Val Ala Asp Arg Thr Glu Cys
        690                 695                 700

Phe Ile Thr Gly Trp Gly Glu Thr Gln Gly Thr Phe Gly Ala Gly Leu
705                 710                 715                 720

Leu Lys Glu Ala Gln Leu Pro Val Ile Glu Asn Lys Val Cys Asn Arg
                725                 730                 735

Asn Glu Phe Leu Asn Gly Arg Val Lys Ser Thr Glu Leu Cys Ala Gly
            740                 745                 750

His Leu Ala Gly Gly Thr Asp Ser Cys Gln Gly Asp Ser Gly Gly Pro
        755                 760                 765

Leu Val Cys Phe Glu Lys Asp Lys Tyr Ile Leu Gln Gly Val Thr Ser
        770                 775                 780

Trp Gly Leu Gly Cys Ala Arg Pro Asn Lys Pro Gly Val Tyr Val Arg
785                 790                 795                 800

Val Ser Arg Phe Val Thr Trp Ile Glu Gly Val Met Arg Asn Asn
                805                 810                 815
```

<210> SEQ ID NO 5
<211> LENGTH: 800
<212> TYPE: PRT
<213> ORGANISM: Pan troglodytes

<400> SEQUENCE: 5

Met Leu Met Asp Tyr Glu Gly Gln Gly Glu Pro Leu Asp Asp Tyr Val
1               5                   10                  15

Asn Thr Gln Gly Ala Ser Leu Phe Ser Val Thr Lys Lys Gln Leu Gly
            20                  25                  30

Ala Gly Ser Ile Glu Glu Cys Ala Ala Lys Cys Glu Glu Asp Lys Glu
        35                  40                  45

Phe Thr Cys Arg Ala Phe Gln Tyr His Ser Lys Glu Gln Gln Cys Val
50                  55                  60

Ile Met Ala Glu Asn Arg Lys Ser Ser Ile Ile Arg Met Arg Asp
65                  70                  75                  80

Val Val Leu Phe Glu Lys Lys Val Tyr Leu Ser Glu Cys Lys Thr Gly
                85                  90                  95

Asn Gly Lys Asn Tyr Arg Gly Thr Met Ser Lys Thr Lys Asn Gly Ile
            100                 105                 110

Thr Cys Gln Lys Trp Ser Ser Thr Ser Pro His Arg Pro Arg Phe Ser
        115                 120                 125

Pro Ala Thr His Pro Ser Glu Gly Leu Glu Glu Asn Tyr Cys Arg Asn
130                 135                 140

Pro Asp Asn Asp Pro Gln Gly Pro Trp Cys Tyr Thr Thr Asp Pro Glu
145                 150                 155                 160

Lys Arg Tyr Asp Tyr Cys Asp Ile Leu Glu Cys Glu Glu Cys Met
                165                 170                 175

His Cys Ser Gly Glu Asn Tyr Asp Gly Lys Ile Ser Lys Thr Met Ser
            180                 185                 190

Gly Leu Glu Cys Gln Ala Trp Asp Ser Gln Ser Pro His Ala His Gly
        195                 200                 205

Tyr Ile Pro Ser Lys Phe Pro Asn Lys Asn Leu Lys Lys Asn Tyr Cys
210                 215                 220

Arg Asn Pro Asp Gly Glu Leu Arg Pro Trp Cys Phe Thr Thr Asp Pro
225                 230                 235                 240

Asn Lys Arg Trp Glu Leu Cys Asp Ile Pro Arg Cys Thr Thr Pro Pro
                245                 250                 255

Pro Ser Ser Gly Pro Thr Tyr Gln Cys Leu Lys Gly Thr Gly Glu Asn
            260                 265                 270

Tyr Arg Gly Asn Val Ala Val Thr Val Ser Gly His Thr Cys Gln His
        275                 280                 285

Trp Ser Ala Gln Thr Pro His Thr His Asn Arg Thr Pro Glu Asn Phe
290                 295                 300

Pro Cys Lys Asn Leu Asp Glu Asn Tyr Cys Arg Asn Pro Asp Gly Lys
305                 310                 315                 320

Arg Ala Pro Trp Cys His Thr Thr Asn Ser Gln Val Arg Trp Glu Tyr
                325                 330                 335

Cys Lys Ile Pro Ser Cys Asp Ser Ser Leu Val Ser Thr Glu Gln Leu
            340                 345                 350

Ala Pro Thr Ala Pro Pro Glu Leu Thr Pro Val Val Gln Asp Cys Tyr
        355                 360                 365

His Gly Asp Gly Gln Ser Tyr Arg Gly Thr Ser Ser Thr Thr Thr Thr
370                 375                 380

```
Gly Lys Lys Cys Gln Ser Trp Ser Ser Met Thr Pro His Arg His Gln
385                 390                 395                 400

Lys Thr Pro Glu Asn Tyr Pro Asn Ala Gly Leu Thr Met Asn Tyr Cys
                405                 410                 415

Arg Asn Pro Asp Ala Asp Lys Gly Pro Trp Cys Phe Thr Thr Asp Pro
            420                 425                 430

Ser Val Arg Trp Glu Tyr Cys Asn Leu Lys Lys Cys Ser Gly Thr Glu
        435                 440                 445

Ala Ser Val Val Ala Pro Pro Val Val Gln Leu Pro Asn Val Glu
    450                 455                 460

Thr Pro Ser Glu Glu Asp Cys Met Phe Gly Asn Gly Lys Gly Tyr Arg
465                 470                 475                 480

Gly Lys Arg Ala Thr Thr Val Thr Gly Thr Pro Cys Gln Asp Trp Ala
                485                 490                 495

Ala Gln Glu Pro His Arg His Ser Ile Phe Thr Pro Glu Thr Asn Pro
            500                 505                 510

Arg Ala Gly Leu Glu Lys Asn Tyr Cys Arg Asn Pro Asp Gly Asp Val
        515                 520                 525

Gly Gly Pro Trp Cys Tyr Thr Thr Asn Pro Arg Lys Leu Tyr Asp Tyr
530                 535                 540

Cys Asp Val Pro Gln Cys Ala Ser Pro Ser Phe Asp Cys Gly Lys Pro
545                 550                 555                 560

Gln Val Glu Pro Lys Lys Cys Pro Gly Arg Val Val Gly Gly Cys Val
                565                 570                 575

Ala His Pro His Ser Trp Pro Trp Gln Val Ser Leu Arg Thr Arg Leu
            580                 585                 590

Gly Met His Phe Cys Gly Gly Thr Leu Ile Ser Pro Glu Trp Val Leu
        595                 600                 605

Thr Ala Ala His Cys Leu Glu Lys Ser Pro Arg Pro Ser Ser Tyr Lys
    610                 615                 620

Val Ile Leu Gly Ala His Gln Glu Val Lys Leu Glu Pro His Val Gln
625                 630                 635                 640

Glu Ile Glu Val Ser Arg Leu Phe Leu Glu Pro Thr Arg Thr Asp Ile
                645                 650                 655

Ala Leu Leu Lys Leu Ser Ser Pro Ala Ile Ile Thr Asp Lys Val Ile
            660                 665                 670

Pro Ala Cys Leu Pro Ser Pro Asn Tyr Val Val Ala Asp Arg Thr Glu
        675                 680                 685

Cys Phe Ile Thr Gly Trp Gly Glu Thr Gln Gly Thr Phe Gly Ala Gly
690                 695                 700

Leu Leu Lys Glu Ala Gln Leu Pro Val Ile Glu Asn Lys Val Cys Asn
705                 710                 715                 720

Arg Asn Glu Phe Leu Asn Gly Arg Val Lys Ser Thr Glu Leu Cys Ala
                725                 730                 735

Gly His Leu Ala Gly Gly Thr Asp Ser Cys Gln Gly Asp Ser Gly Gly
            740                 745                 750

Pro Leu Val Cys Phe Glu Lys Asp Lys Tyr Ile Leu Gln Gly Val Thr
        755                 760                 765

Ser Trp Gly Leu Gly Cys Ala Arg Pro Asn Lys Pro Gly Val Tyr Val
770                 775                 780

Arg Val Ser Arg Phe Val Thr Trp Ile Glu Gly Val Met Arg Asn Asn
785                 790                 795                 800
```

<210> SEQ ID NO 6
<211> LENGTH: 810
<212> TYPE: PRT
<213> ORGANISM: Macaca mulatta

<400> SEQUENCE: 6

```
Met Glu His Lys Glu Val Val Leu Leu Leu Phe Leu Lys Ser
1               5                   10                  15

Gly Gln Gly Glu Pro Leu Asp Asp Tyr Val Asn Thr Lys Gly Ala Ser
            20                  25                  30

Leu Phe Ser Ile Thr Lys Lys Gln Leu Gly Ala Gly Ser Ile Glu Glu
        35                  40                  45

Cys Ala Ala Lys Cys Glu Glu Glu Glu Phe Thr Cys Arg Ser Phe
    50                  55                  60

Gln Tyr His Ser Lys Glu Gln Gln Cys Val Ile Met Ala Glu Asn Arg
65                  70                  75                  80

Lys Ser Ser Ile Val Phe Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Arg Thr Gly Ile Thr Cys Gln Lys Trp Ser
        115                 120                 125

Ser Thr Ser Pro His Arg Pro Thr Phe Ser Pro Ala Thr His Pro Ser
130                 135                 140

Glu Gly Leu Glu Glu Asn Tyr Cys Arg Asn Pro Asp Asn Asp Gly Gln
145                 150                 155                 160

Gly Pro Trp Cys Tyr Thr Thr Asp Pro Glu Glu Arg Phe Asp Tyr Cys
                165                 170                 175

Asp Ile Pro Glu Cys Glu Asp Glu Cys Met His Cys Ser Gly Glu Asn
            180                 185                 190

Tyr Asp Gly Lys Ile Ser Lys Thr Met Ser Gly Leu Glu Cys Gln Ala
        195                 200                 205

Trp Asp Ser Gln Ser Pro His Ala His Gly Tyr Ile Pro Ser Lys Phe
    210                 215                 220

Pro Asn Lys Asn Leu Lys Lys Asn Tyr Cys Arg Asn Pro Asp Gly Glu
225                 230                 235                 240

Pro Arg Pro Trp Cys Phe Thr Thr Asp Pro Asn Lys Arg Trp Glu Leu
                245                 250                 255

Cys Asp Ile Pro Arg Cys Thr Thr Pro Pro Pro Ser Ser Gly Pro Thr
            260                 265                 270

Tyr Gln Cys Leu Lys Gly Thr Gly Glu Asn Tyr Arg Gly Asp Val Ala
        275                 280                 285

Val Thr Val Ser Gly His Thr Cys His Gly Trp Ser Ala Gln Thr Pro
    290                 295                 300

His Thr His Asn Arg Thr Pro Glu Asn Phe Pro Cys Lys Asn Leu Asp
305                 310                 315                 320

Glu Asn Tyr Cys Arg Asn Pro Asp Gly Glu Lys Ala Pro Trp Cys Tyr
                325                 330                 335

Thr Thr Asn Ser Gln Val Arg Trp Glu Tyr Cys Lys Ile Pro Ser Cys
            340                 345                 350

Glu Ser Ser Pro Val Ser Thr Glu Pro Leu Asp Pro Thr Ala Pro Pro
        355                 360                 365

Glu Leu Thr Pro Val Val Gln Glu Cys Tyr His Gly Asp Gly Gln Ser
    370                 375                 380
```

```
Tyr Arg Gly Thr Ser Ser Thr Thr Thr Gly Lys Lys Cys Gln Ser
385                 390                 395                 400

Trp Ser Ser Met Thr Pro His Trp His Glu Lys Thr Pro Glu Asn Phe
            405                 410                 415

Pro Asn Ala Gly Leu Thr Met Asn Tyr Cys Arg Asn Pro Asp Ala Asp
        420                 425                 430

Lys Gly Pro Trp Cys Phe Thr Thr Asp Pro Ser Val Arg Trp Glu Tyr
    435                 440                 445

Cys Asn Leu Lys Lys Cys Ser Gly Thr Glu Gly Ser Val Ala Ala Pro
450                 455                 460

Pro Pro Val Ala Gln Leu Pro Asp Ala Glu Thr Pro Ser Glu Glu Asp
465                 470                 475                 480

Cys Met Phe Gly Asn Gly Lys Gly Tyr Arg Gly Lys Lys Ala Thr Thr
            485                 490                 495

Val Thr Gly Thr Pro Cys Gln Glu Trp Ala Ala Gln Glu Pro His Ser
            500                 505                 510

His Arg Ile Phe Thr Pro Glu Thr Asn Pro Arg Ala Gly Leu Glu Lys
        515                 520                 525

Asn Tyr Cys Arg Asn Pro Asp Gly Asp Val Gly Gly Pro Trp Cys Tyr
530                 535                 540

Thr Thr Asn Pro Arg Lys Leu Phe Asp Tyr Cys Asp Val Pro Gln Cys
545                 550                 555                 560

Ala Ala Ser Ser Phe Asp Cys Gly Lys Pro Gln Val Glu Pro Lys Lys
                565                 570                 575

Cys Pro Gly Arg Val Val Gly Gly Cys Val Ala Tyr Pro His Ser Trp
            580                 585                 590

Pro Trp Gln Ile Ser Leu Arg Thr Arg Leu Gly Met His Phe Cys Gly
        595                 600                 605

Gly Thr Leu Ile Ser Pro Glu Trp Val Leu Thr Ala Ala His Cys Leu
    610                 615                 620

Glu Lys Ser Ser Arg Pro Ser Phe Tyr Lys Val Ile Leu Gly Ala His
625                 630                 635                 640

Arg Glu Val His Leu Glu Pro His Val Gln Glu Ile Glu Val Ser Lys
                645                 650                 655

Met Phe Ser Glu Pro Ala Arg Ala Asp Ile Ala Leu Leu Lys Leu Ser
            660                 665                 670

Ser Pro Ala Ile Ile Thr Asp Lys Val Ile Pro Ala Cys Leu Pro Ser
        675                 680                 685

Pro Asn Tyr Val Val Ala Asp Arg Thr Glu Cys Phe Ile Thr Gly Trp
    690                 695                 700

Gly Glu Thr Gln Gly Thr Tyr Gly Ala Gly Leu Leu Lys Glu Ala Arg
705                 710                 715                 720

Leu Pro Val Ile Glu Asn Lys Val Cys Asn Arg Tyr Glu Phe Leu Asn
                725                 730                 735

Gly Thr Val Lys Thr Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780

Ala Arg Pro Asn Lys Pro Gly Val Tyr Val Arg Val Ser Arg Phe Val
785                 790                 795                 800
```

-continued

```
Thr Trp Ile Glu Gly Val Met Arg Asn Asn
            805                 810

<210> SEQ ID NO 7
<211> LENGTH: 810
<212> TYPE: PRT
<213> ORGANISM: Pongo abelii

<400> SEQUENCE: 7

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Arg Ala Gly Ser Ile Glu Glu
            35                  40                  45

Cys Ala Ala Lys Cys Glu Glu Lys Glu Phe Thr Cys Arg Ala Phe
50                  55                  60

Gln Tyr His Ser Lys Glu Gln Gln Cys Val Ile Met Ala Glu Asn Arg
65                  70                  75                  80

Lys Ser Ser Ile Ile Ile Arg Met Arg Asp Val Val Leu Phe Glu Lys
                85                  90                  95

Lys Val Tyr Leu Ser Glu Cys Lys Thr Gly Asn Gly Lys Asn Tyr Arg
            100                 105                 110

Gly Thr Met Ser Lys Thr Lys Asn Gly Ile Thr Cys Gln Lys Trp Ser
            115                 120                 125

Ser Thr Ser Pro His Arg Pro Arg Phe Ser Pro Ala Thr His Pro Ser
            130                 135                 140

Glu Gly Leu Glu Glu Asn Tyr Cys Arg Asn Pro Asp Asn Asp Ala Gln
145                 150                 155                 160

Gly Pro Trp Cys Tyr Thr Thr Asp Pro Glu His Arg Tyr Asp Tyr Cys
            165                 170                 175

Asp Ile Pro Glu Cys Glu Glu Ala Cys Met His Cys Ser Gly Glu Asn
            180                 185                 190

Tyr Asp Gly Lys Ile Ser Lys Thr Met Ser Gly Leu Glu Cys Gln Ala
            195                 200                 205

Trp Asp Ser Gln Ser Pro His Ala His Gly Tyr Ile Pro Ser Lys Phe
210                 215                 220

Pro Asn Lys Asn Leu Lys Lys Asn Tyr Cys Arg Asn Pro Asp Gly Glu
225                 230                 235                 240

Pro Arg Pro Trp Cys Phe Thr Thr Asp Pro Asn Lys Arg Trp Glu Leu
            245                 250                 255

Cys Asp Ile Pro Arg Cys Thr Thr Pro Pro Pro Ser Ser Gly Pro Thr
            260                 265                 270

Tyr Gln Cys Leu Lys Gly Thr Gly Glu Asn Tyr Arg Gly Asn Val Ala
            275                 280                 285

Val Thr Val Ser Gly His Thr Cys Gln Arg Trp Ser Ala Gln Thr Pro
            290                 295                 300

Gln Thr His Asn Arg Thr Pro Glu Asn Phe Pro Cys Lys Asn Leu Asp
305                 310                 315                 320

Glu Asn Tyr Cys Arg Asn Pro Asp Gly Glu Lys Ala Pro Trp Cys Tyr
            325                 330                 335

Thr Thr Asn Ser Gln Val Arg Trp Glu Tyr Cys Lys Ile Pro Ser Cys
            340                 345                 350

Gly Ser Ser Pro Val Ser Thr Glu Gln Leu Asp Pro Thr Ala Pro Pro
            355                 360                 365
```

```
Glu Leu Thr Pro Val Val Gln Asp Cys Tyr His Gly Asp Gly Gln Ser
    370                 375                 380

Tyr Arg Gly Thr Ser Ser Thr Thr Thr Thr Gly Lys Lys Cys Gln Ser
385                 390                 395                 400

Trp Ser Ser Met Thr Pro His Trp His Gln Lys Thr Pro Glu Asn Tyr
                405                 410                 415

Pro Asp Ala Gly Leu Thr Met Asn Tyr Cys Arg Asn Pro Asp Ala Asp
                420                 425                 430

Lys Gly Pro Trp Cys Phe Thr Thr Asp Pro Ser Val Arg Trp Glu Tyr
            435                 440                 445

Cys Asn Leu Lys Lys Cys Ser Gly Thr Glu Gly Ser Val Val Ala Pro
    450                 455                 460

Pro Pro Val Val Gln Leu Pro Asn Val Glu Thr Pro Ser Glu Glu Asp
465                 470                 475                 480

Cys Met Phe Gly Asn Gly Lys Gly Tyr Arg Gly Lys Arg Ala Thr Thr
                485                 490                 495

Val Thr Gly Thr Pro Cys Gln Glu Trp Ala Ala Gln Glu Pro His Arg
                500                 505                 510

His Ser Ile Phe Thr Pro Gln Thr Asn Pro Arg Ala Gly Leu Glu Lys
    515                 520                 525

Asn Tyr Cys Arg Asn Pro Asp Gly Asp Glu Gly Gly Pro Trp Cys Tyr
    530                 535                 540

Thr Thr Asn Pro Arg Lys His Tyr Asp Tyr Cys Asp Val Pro Gln Cys
545                 550                 555                 560

Ala Ser Ser Ser Phe Asp Cys Gly Lys Pro Gln Val Glu Pro Lys Lys
                565                 570                 575

Cys Pro Gly Arg Val Val Gly Gly Cys Val Ala Asn Ala His Ser Trp
            580                 585                 590

Pro Trp Gln Val Ser Leu Arg Thr Arg Phe Gly Thr His Phe Cys Gly
            595                 600                 605

Gly Thr Leu Ile Ser Pro Glu Trp Val Leu Thr Ala Ala His Cys Leu
        610                 615                 620

Glu Lys Ser Pro Arg Pro Ser Ser Tyr Lys Val Ile Leu Gly Ala His
625                 630                 635                 640

Gln Glu Val Asn Leu Glu Pro His Val Gln Glu Ile Glu Val Ser Arg
                645                 650                 655

Leu Phe Leu Glu Pro Thr Arg Ala Asp Ile Ala Leu Leu Lys Leu Ser
                660                 665                 670

Ser Pro Ala Val Ile Thr Asp Lys Val Ile Pro Ala Cys Leu Pro Ser
            675                 680                 685

Pro Asn Tyr Val Val Ala Gly Arg Thr Glu Cys Phe Ile Thr Gly Trp
690                 695                 700

Gly Glu Thr Gln Gly Thr Phe Gly Ala Gly Leu Leu Lys Glu Ala Gln
705                 710                 715                 720

Leu Pro Val Ile Glu Asn Lys Val Cys Asn Arg Tyr Glu Phe Leu Asn
                725                 730                 735

Gly Arg Val Lys Ser Thr Glu Leu Cys Ala Gly His Leu Ala Gly Gly
            740                 745                 750

Thr Asp Ser Cys Gln Gly Asp Ser Gly Gly Pro Leu Val Cys Phe Glu
        755                 760                 765

Lys Asp Lys Tyr Ile Leu Gln Gly Val Thr Ser Trp Gly Leu Gly Cys
    770                 775                 780
```

```
Ala Arg Pro Asn Lys Pro Gly Val Tyr Val Arg Ser Arg Phe Val
785                 790                 795                 800

Thr Trp Ile Glu Gly Val Met Arg Asn Asn
                805                 810

<210> SEQ ID NO 8
<211> LENGTH: 809
<212> TYPE: PRT
<213> ORGANISM: Sus scrofa

<400> SEQUENCE: 8

Met Asp His Lys Glu Val Val Leu Leu Leu Leu Phe Leu Lys Ser
1               5                   10                  15

Gly Leu Gly Asp Ser Leu Asp Asp Tyr Val Asn Thr Gln Gly Ala Phe
            20                  25                  30

Leu Phe Ser Leu Ser Arg Lys Gln Val Ala Ala Arg Ser Val Glu Glu
            35                  40                  45

Cys Ala Ala Lys Cys Glu Ala Glu Thr Asn Phe Ile Cys Arg Ala Phe
50                  55                  60

Gln Tyr His Ser Lys Asp Gln Gln Cys Val Val Met Ala Glu Asn Ser
65                  70                  75                  80

Lys Thr Ser Pro Ile Ala Arg Met Arg Asp Val Val Leu Phe Glu Lys
                85                  90                  95

Arg Ile Tyr Leu Ser Glu Cys Lys Thr Gly Asn Gly Lys Asn Tyr Arg
            100                 105                 110

Gly Thr Thr Ser Lys Thr Lys Ser Gly Val Ile Cys Gln Lys Trp Ser
            115                 120                 125

Val Ser Ser Pro His Ile Pro Lys Tyr Ser Pro Glu Lys Phe Pro Leu
130                 135                 140

Ala Gly Leu Glu Glu Asn Tyr Cys Arg Asn Pro Asp Asn Asp Glu Lys
145                 150                 155                 160

Gly Pro Trp Cys Tyr Thr Thr Asp Pro Glu Thr Arg Phe Asp Tyr Cys
                165                 170                 175

Asp Ile Pro Glu Cys Glu Asp Glu Cys Met His Cys Ser Gly Glu His
            180                 185                 190

Tyr Glu Gly Lys Ile Ser Lys Thr Met Ser Gly Ile Glu Cys Gln Ser
            195                 200                 205

Trp Gly Ser Gln Ser Pro His Ala His Gly Tyr Leu Pro Ser Lys Phe
210                 215                 220

Pro Asn Lys Asn Leu Lys Met Asn Tyr Cys Arg Asn Pro Asp Gly Glu
225                 230                 235                 240

Pro Arg Pro Trp Cys Phe Thr Thr Asp Pro Asn Lys Arg Trp Glu Phe
                245                 250                 255

Cys Asp Ile Pro Arg Cys Thr Thr Pro Pro Thr Ser Gly Pro Thr
            260                 265                 270

Tyr Gln Cys Leu Lys Gly Arg Gly Glu Asn Tyr Arg Gly Thr Val Ser
            275                 280                 285

Val Thr Ala Ser Gly His Thr Cys Gln Arg Trp Ser Ala Gln Ser Pro
290                 295                 300

His Lys His Asn Arg Thr Pro Glu Asn Phe Pro Cys Lys Asn Leu Glu
305                 310                 315                 320

Glu Asn Tyr Cys Arg Asn Pro Asp Gly Glu Thr Ala Pro Trp Cys Tyr
                325                 330                 335

Thr Thr Asp Ser Glu Val Arg Trp Asp Tyr Cys Lys Ile Pro Ser Cys
            340                 345                 350
```

```
Gly Ser Ser Thr Thr Ser Thr Glu Tyr Leu Asp Ala Pro Val Pro Pro
            355                 360                 365

Glu Gln Thr Pro Val Ala Gln Asp Cys Tyr Arg Gly Asn Gly Glu Ser
    370                 375                 380

Tyr Arg Gly Thr Ser Thr Thr Ile Thr Gly Arg Lys Cys Gln Ser
385                 390                 395                 400

Trp Val Ser Met Thr Pro His Arg His Glu Lys Thr Pro Gly Asn Phe
                405                 410                 415

Pro Asn Ala Gly Leu Thr Met Asn Tyr Cys Arg Asn Pro Asp Ala Asp
            420                 425                 430

Lys Ser Pro Trp Cys Tyr Thr Thr Asp Pro Arg Val Arg Trp Glu Tyr
    435                 440                 445

Cys Asn Leu Lys Lys Cys Ser Glu Thr Glu Gln Gln Val Thr Asn Phe
    450                 455                 460

Pro Ala Ile Ala Gln Val Pro Ser Val Glu Asp Leu Ser Glu Asp Cys
465                 470                 475                 480

Met Phe Gly Asn Gly Lys Arg Tyr Arg Gly Lys Arg Ala Thr Thr Val
                485                 490                 495

Ala Gly Val Pro Cys Gln Glu Trp Ala Ala Gln Glu Pro His Arg His
            500                 505                 510

Ser Ile Phe Thr Pro Glu Thr Asn Pro Arg Ala Gly Leu Glu Lys Asn
    515                 520                 525

Tyr Cys Arg Asn Pro Asp Gly Asp Asn Gly Pro Trp Cys Tyr Thr
    530                 535                 540

Thr Asn Pro Gln Lys Leu Phe Asp Tyr Cys Asp Val Pro Gln Cys Val
545                 550                 555                 560

Thr Ser Ser Phe Asp Cys Gly Lys Pro Lys Val Glu Pro Lys Lys Cys
                565                 570                 575

Pro Ala Arg Val Val Gly Gly Cys Val Ser Ile Pro His Ser Trp Pro
            580                 585                 590

Trp Gln Ile Ser Leu Arg His Arg Tyr Gly Gly His Phe Cys Gly Gly
    595                 600                 605

Thr Leu Ile Ser Pro Glu Trp Val Leu Thr Ala Lys His Cys Leu Glu
    610                 615                 620

Lys Ser Ser Ser Pro Ser Ser Tyr Lys Val Ile Leu Gly Ala His Glu
625                 630                 635                 640

Glu Tyr His Leu Gly Glu Gly Val Gln Glu Ile Asp Val Ser Lys Leu
                645                 650                 655

Phe Lys Glu Pro Ser Glu Ala Asp Ile Ala Leu Leu Lys Leu Ser Ser
            660                 665                 670

Pro Ala Ile Ile Thr Asp Lys Val Ile Pro Ala Cys Leu Pro Thr Pro
    675                 680                 685

Asn Tyr Val Val Ala Asp Arg Thr Ala Cys Tyr Ile Thr Gly Trp Gly
    690                 695                 700

Glu Thr Lys Gly Thr Tyr Gly Ala Gly Leu Leu Lys Glu Ala Arg Leu
705                 710                 715                 720

Pro Val Ile Glu Asn Lys Val Cys Asn Arg Tyr Glu Tyr Leu Gly Gly
                725                 730                 735

Lys Val Ser Pro Asn Glu Leu Cys Ala Gly His Leu Ala Gly Gly Ile
            740                 745                 750

Asp Ser Cys Gln Gly Asp Ser Gly Gly Pro Leu Val Cys Phe Glu Lys
    755                 760                 765
```

-continued

```
Asp Lys Tyr Ile Leu Gln Gly Val Thr Ser Trp Gly Leu Gly Cys Ala
770                 775                 780

Leu Pro Asn Lys Pro Gly Val Tyr Val Arg Val Ser Arg Phe Val Thr
785                 790                 795                 800

Trp Ile Glu Glu Ile Met Arg Arg Asn
                805

<210> SEQ ID NO 9
<211> LENGTH: 812
<212> TYPE: PRT
<213> ORGANISM: Bos Taurus

<400> SEQUENCE: 9

Met Leu Pro Ala Ser Pro Lys Met Glu His Lys Ala Val Val Phe Leu
1               5                   10                  15

Ile Leu Leu Phe Leu Lys Ser Gly Leu Gly Asp Leu Leu Asp Asp Tyr
                20                  25                  30

Val Asn Thr Gln Gly Ala Ser Leu Leu Ser Leu Ser Arg Lys Asn Leu
            35                  40                  45

Ala Gly Arg Ser Val Glu Asp Cys Ala Ala Lys Cys Glu Glu Glu Thr
50                  55                  60

Asp Phe Val Cys Arg Ala Phe Gln Tyr His Ser Lys Glu Gln Gln Cys
65                  70                  75                  80

Val Val Met Ala Glu Asn Ser Lys Asn Thr Pro Val Phe Arg Met Arg
                85                  90                  95

Asp Val Ile Leu Tyr Glu Lys Arg Ile Tyr Leu Leu Gly Cys Lys Thr
            100                 105                 110

Gly Asn Gly Gln Thr Tyr Arg Gly Thr Thr Ala Glu Thr Lys Ser Gly
        115                 120                 125

Val Thr Cys Gln Lys Trp Ser Ala Thr Ser Pro His Val Pro Lys Phe
130                 135                 140

Ser Pro Glu Lys Phe Pro Leu Ala Gly Leu Glu Glu Asn Tyr Cys Arg
145                 150                 155                 160

Asn Pro Asp Asn Asp Glu Asn Gly Pro Trp Cys Tyr Thr Thr Asp Pro
                165                 170                 175

Asp Lys Arg Tyr Asp Tyr Cys Asp Ile Pro Glu Cys Glu Asp Lys Cys
            180                 185                 190

Met His Cys Ser Gly Glu Asn Tyr Glu Gly Lys Ile Ala Lys Thr Met
        195                 200                 205

Ser Gly Arg Asp Cys Gln Ala Trp Asp Ser Gln Ser Pro His Ala His
210                 215                 220

Gly Tyr Ile Pro Ser Lys Phe Pro Ser Lys Asn Leu Lys Met Asn Tyr
225                 230                 235                 240

Cys Arg Asn Pro Asp Gly Glu Pro Arg Pro Trp Cys Phe Thr Thr Asp
                245                 250                 255

Pro Gln Lys Arg Trp Glu Phe Cys Asp Ile Pro Arg Cys Thr Thr Pro
            260                 265                 270

Pro Pro Ser Ser Gly Pro Lys Tyr Gln Cys Leu Lys Gly Thr Gly Lys
        275                 280                 285

Asn Tyr Gly Gly Thr Val Ala Val Thr Glu Ser Gly His Thr Cys Gln
290                 295                 300

Arg Trp Ser Glu Gln Thr Pro His Lys His Asn Arg Thr Pro Glu Asn
305                 310                 315                 320

Phe Pro Cys Lys Asn Leu Glu Glu Asn Tyr Cys Arg Asn Pro Asn Gly
                325                 330                 335
```

-continued

```
Glu Lys Ala Pro Trp Cys Tyr Thr Thr Asn Ser Lys Val Arg Trp Glu
            340                 345                 350

Tyr Cys Thr Ile Pro Ser Cys Glu Ser Ser Pro Leu Ser Thr Glu Arg
            355                 360                 365

Met Asp Val Pro Val Pro Pro Glu Gln Thr Pro Val Pro Gln Asp Cys
370                 375                 380

Tyr His Gly Asn Gly Gln Ser Tyr Arg Gly Thr Ser Ser Thr Thr Ile
385                 390                 395                 400

Thr Gly Arg Lys Cys Gln Ser Trp Ser Ser Met Thr Pro His Arg His
                405                 410                 415

Leu Lys Thr Pro Glu Asn Tyr Pro Asn Ala Gly Leu Thr Met Asn Tyr
            420                 425                 430

Cys Arg Asn Pro Asp Ala Asp Lys Ser Pro Trp Cys Tyr Thr Thr Asp
            435                 440                 445

Pro Arg Val Arg Trp Glu Phe Cys Asn Leu Lys Lys Cys Ser Glu Thr
        450                 455                 460

Pro Glu Gln Val Pro Ala Ala Pro Gln Ala Pro Gly Val Glu Asn Pro
465                 470                 475                 480

Pro Glu Ala Asp Cys Met Ile Gly Met Gly Lys Ser Tyr Arg Gly Lys
                485                 490                 495

Lys Ala Thr Thr Val Ala Gly Val Pro Cys Gln Glu Trp Ala Ala Gln
            500                 505                 510

Glu Pro His His His Ser Ile Phe Thr Pro Glu Thr Asn Pro Gln Ser
            515                 520                 525

Gly Leu Glu Arg Asn Tyr Cys Arg Asn Pro Asp Gly Asp Val Asn Gly
            530                 535                 540

Pro Trp Cys Tyr Thr Met Asn Pro Arg Lys Leu Phe Asp Tyr Cys Asp
545                 550                 555                 560

Val Pro Gln Cys Glu Ser Ser Phe Asp Cys Gly Lys Pro Lys Val Glu
                565                 570                 575

Pro Lys Lys Cys Ser Gly Arg Ile Val Gly Gly Cys Val Ser Lys Pro
            580                 585                 590

His Ser Trp Pro Trp Gln Val Ser Leu Arg Arg Ser Ser Arg His Phe
            595                 600                 605

Cys Gly Gly Thr Leu Ile Ser Pro Lys Trp Val Leu Thr Ala Ala His
            610                 615                 620

Cys Leu Asp Asn Ile Leu Ala Leu Ser Phe Tyr Lys Val Ile Leu Gly
625                 630                 635                 640

Ala His Asn Glu Lys Val Arg Glu Gln Ser Val Gln Glu Ile Pro Val
                645                 650                 655

Ser Arg Leu Phe Arg Glu Pro Ser Gln Ala Asp Ile Ala Leu Leu Lys
            660                 665                 670

Leu Ser Arg Pro Ala Ile Ile Thr Lys Glu Val Ile Pro Ala Cys Leu
            675                 680                 685

Pro Pro Pro Asn Tyr Met Val Ala Ala Arg Thr Glu Cys Tyr Ile Thr
            690                 695                 700

Gly Trp Gly Glu Thr Gln Gly Thr Phe Gly Glu Gly Leu Leu Lys Glu
705                 710                 715                 720

Ala His Leu Pro Val Ile Glu Asn Lys Val Cys Asn Arg Asn Glu Tyr
                725                 730                 735

Leu Asp Gly Arg Val Lys Pro Thr Glu Leu Cys Ala Gly His Leu Ile
            740                 745                 750
```

Gly Gly Thr Asp Ser Cys Gln Gly Asp Ser Gly Pro Leu Val Cys
        755                 760                 765

Phe Glu Lys Asp Lys Tyr Ile Leu Gln Gly Val Thr Ser Trp Gly Leu
        770                 775                 780

Gly Cys Ala Arg Pro Asn Lys Pro Gly Val Tyr Val Arg Val Ser Pro
785                 790                 795                 800

Tyr Val Pro Trp Ile Glu Glu Thr Met Arg Arg Asn
                805                 810

<210> SEQ ID NO 10
<211> LENGTH: 811
<212> TYPE: PRT
<213> ORGANISM: Equus caballus

<400> SEQUENCE: 10

Met Glu His Gln Glu Val Val Phe Leu Leu Leu Phe Leu Lys Ser
1               5                   10                  15

Gly His Gly Asp Ile Leu Asp Asp Tyr Val Thr Thr Gln Gly Ala Ser
            20                  25                  30

Leu Phe Thr Phe Thr Arg Lys Pro Leu Ser Ala Ser Ile Glu Glu
            35                  40                  45

Cys Glu Ala Lys Cys Thr Glu Glu Thr Ala Phe Ile Cys Arg Ala Phe
    50                  55                  60

Gln Tyr His Ser Lys Glu Pro Arg Cys Val Leu Leu Ala Glu Asn Arg
65                  70                  75                  80

Lys Ser Ser Pro Val Met Arg Met Arg Asp Val Ile Leu Phe Glu Lys
                85                  90                  95

Arg Ile Tyr Leu Ser Glu Cys Lys Thr Gly Thr Gly Arg Ser Tyr Arg
            100                 105                 110

Gly Thr Thr Ser Lys Thr Lys Asn Gly Val Ser Cys Gln Lys Trp Ser
            115                 120                 125

Asp Thr Ser Pro His Ile Pro Lys Tyr Ser Pro Asp Lys Asn Pro Ser
    130                 135                 140

Glu Gly Leu Glu Glu Asn Tyr Cys Arg Asn Pro Asp Asn Asp Glu Lys
145                 150                 155                 160

Gly Pro Trp Cys Tyr Thr Thr Asp Pro Gly Thr Arg Phe Asp Tyr Cys
                165                 170                 175

Asp Ile Pro Glu Cys Glu Asp Glu Cys Met His Cys Ser Gly Glu Asn
            180                 185                 190

Tyr Glu Gly Lys Ile Ser Lys Thr Ile Ser Gly Leu Glu Cys Gln Pro
            195                 200                 205

Trp Ala Ser Gln Ser Pro His Ala His Gly Tyr Ile Pro Ser Lys Phe
    210                 215                 220

Pro Asn Lys Asn Leu Arg Met Asn Tyr Cys Arg Asn Pro Asp Gly Glu
225                 230                 235                 240

Pro Arg Pro Trp Cys Phe Thr Met Asp Pro Asp Lys Arg Trp Glu Phe
                245                 250                 255

Cys Asp Ile Pro Arg Cys Ser Thr Pro Pro Ser Ser Gly Pro Thr
            260                 265                 270

Tyr Gln Cys Leu Lys Gly Arg Gly Glu Asn Tyr Arg Gly Arg Val Ser
            275                 280                 285

Val Thr Gln Ser Gly Leu Thr Cys Gln Arg Trp Ser Glu Gln Thr Pro
    290                 295                 300

His Lys His Asn Arg Thr Pro Asp Asn Phe Pro Cys Lys Asn Leu Asp
305                 310                 315                 320

```
Glu Asn Tyr Cys Arg Asn Pro Asp Gly Glu Thr Ala Pro Trp Cys Tyr
                325                 330                 335
Thr Thr Ser Ser Glu Thr Arg Trp Glu Tyr Cys Asn Ile Pro Ser Cys
            340                 345                 350
Thr Ser Ser Ser Val Pro Thr Glu Ile Thr Asp Ala Ser Glu Pro Pro
            355                 360                 365
Glu Gln Thr Pro Val Val Gln Asp Cys Tyr Gln Asp Lys Gly Glu Ser
        370                 375                 380
Tyr Arg Gly Thr Ser Ser Ile Thr Val Thr Gly Lys Lys Cys Gln Ser
385                 390                 395                 400
Trp Ser Ser Met Thr Pro His Trp His Gln Lys Thr Pro Glu Lys Tyr
                405                 410                 415
Pro Asn Ala Asp Leu Thr Met Asn Tyr Cys Arg Asn Pro Asp Gly Asp
            420                 425                 430
Lys Gly Pro Trp Cys Tyr Thr Thr Asp Pro Ser Val Arg Trp Glu Phe
            435                 440                 445
Cys Asn Leu Arg Arg Cys Ser Glu Thr Gln Gln Ser Phe Ser Asn Ser
        450                 455                 460
Ser Pro Thr Asp Thr Gln Val Pro Ser Val Gln Glu Pro Ser Glu Pro
465                 470                 475                 480
Asp Cys Met Leu Gly Ile Gly Lys Gly Tyr Gln Gly Lys Lys Ala Thr
                485                 490                 495
Thr Val Thr Gly Thr Arg Cys Gln Ala Trp Ala Ala Gln Glu Pro His
                500                 505                 510
Arg His Ser Ile Phe Thr Pro Glu Ala Asn Pro Trp Ala Asn Leu Glu
            515                 520                 525
Lys Asn Tyr Cys Arg Asn Pro Asp Gly Asp Val Asn Gly Pro Trp Cys
        530                 535                 540
Tyr Thr Met Asn Pro Gln Lys Leu Phe Asp Tyr Cys Asp Val Pro Gln
545                 550                 555                 560
Cys Glu Ser Ser Pro Phe Asp Cys Gly Lys Pro Lys Val Glu Pro Lys
                565                 570                 575
Lys Cys Ser Gly Arg Ile Val Gly Gly Cys Val Ala Ile Ala His Ser
                580                 585                 590
Trp Pro Trp Gln Ile Ser Leu Arg Thr Arg Phe Gly Arg His Phe Cys
            595                 600                 605
Gly Gly Thr Leu Ile Ser Pro Glu Trp Val Leu Thr Ala Ala His Cys
        610                 615                 620
Leu Glu Arg Ser Ser Arg Pro Ser Thr Tyr Lys Val Val Leu Gly Thr
625                 630                 635                 640
His His Glu Leu Arg Leu Ala Ala Gly Ala Gln Gln Ile Asp Val Ser
                645                 650                 655
Lys Leu Phe Leu Glu Pro Ser Arg Ala Asp Ile Ala Leu Leu Lys Leu
            660                 665                 670
Ser Ser Pro Ala Ile Ile Thr Gln Asn Val Ile Pro Ala Cys Leu Pro
        675                 680                 685
Pro Ala Asp Tyr Val Val Ala Asn Trp Ala Glu Cys Phe Val Thr Gly
        690                 695                 700
Trp Gly Glu Thr Gln Asp Ser Ser Asn Ala Gly Val Leu Lys Glu Ala
705                 710                 715                 720
Gln Leu Pro Val Ile Glu Asn Lys Val Cys Asn Arg Tyr Glu Tyr Leu
                725                 730                 735
```

```
Asn Gly Arg Val Lys Ser Thr Glu Leu Cys Ala Gly His Leu Val Gly
                740                 745                 750

Gly Val Asp Ser Cys Gln Gly Asp Ser Gly Pro Leu Val Cys Phe
            755                 760                 765

Glu Lys Asp Lys Tyr Ile Leu Gln Gly Val Thr Ser Trp Gly Leu Gly
770                 775                 780

Cys Ala Arg Pro Asn Lys Pro Gly Val Tyr Val Arg Val Ser Ser Phe
785                 790                 795                 800

Ile Asn Trp Ile Glu Arg Ile Met Gln Ser Asn
                805                 810

<210> SEQ ID NO 11
<211> LENGTH: 812
<212> TYPE: PRT
<213> ORGANISM: Mus musculus

<400> SEQUENCE: 11

Met Asp His Lys Glu Val Ile Leu Leu Phe Leu Leu Leu Lys Pro
1               5                   10                  15

Gly Gln Gly Asp Ser Leu Asp Gly Tyr Ile Ser Thr Gln Gly Ala Ser
                20                  25                  30

Leu Phe Ser Leu Thr Lys Lys Gln Leu Ala Ala Gly Gly Val Ala Asp
            35                  40                  45

Cys Leu Ala Lys Cys Glu Gly Glu Thr Asp Phe Val Cys Arg Ser Phe
50                  55                  60

Gln Tyr His Ser Lys Glu Gln Gln Cys Val Ile Met Ala Glu Asn Ser
65                  70                  75                  80

Lys Thr Ser Ser Ile Ile Arg Met Arg Asp Val Ile Leu Phe Glu Lys
                85                  90                  95

Arg Val Tyr Leu Ser Glu Cys Lys Thr Gly Ile Gly Asn Ser Tyr Arg
                100                 105                 110

Gly Thr Met Ser Arg Thr Lys Ser Gly Val Ala Cys Gln Lys Trp Gly
            115                 120                 125

Ala Thr Phe Pro His Val Pro Asn Tyr Ser Pro Ser Thr His Pro Asn
130                 135                 140

Glu Gly Leu Glu Glu Asn Tyr Cys Arg Asn Pro Asp Asn Asp Glu Gln
145                 150                 155                 160

Gly Pro Trp Cys Tyr Thr Thr Asp Pro Asp Lys Arg Tyr Asp Tyr Cys
                165                 170                 175

Asn Ile Pro Glu Cys Glu Glu Cys Met Tyr Cys Ser Gly Glu Lys
            180                 185                 190

Tyr Glu Gly Lys Ile Ser Lys Thr Met Ser Gly Leu Asp Cys Gln Ala
            195                 200                 205

Trp Asp Ser Gln Ser Pro His Ala His Gly Tyr Ile Pro Ala Lys Phe
210                 215                 220

Pro Ser Lys Asn Leu Lys Met Asn Tyr Cys Arg Asn Pro Asp Gly Glu
225                 230                 235                 240

Pro Arg Pro Trp Cys Phe Thr Thr Asp Pro Thr Lys Arg Trp Glu Tyr
                245                 250                 255

Cys Asp Ile Pro Arg Cys Thr Thr Pro Pro Pro Ser Pro Thr
                260                 265                 270

Tyr Gln Cys Leu Lys Gly Arg Gly Glu Asn Tyr Arg Gly Thr Val Ser
            275                 280                 285

Val Thr Val Ser Gly Lys Thr Cys Gln Arg Trp Ser Glu Gln Thr Pro
290                 295                 300
```

-continued

His Arg His Asn Arg Thr Pro Glu Asn Phe Pro Cys Lys Asn Leu Glu
305                 310                 315                 320

Glu Asn Tyr Cys Arg Asn Pro Asp Gly Glu Thr Ala Pro Trp Cys Tyr
            325                 330                 335

Thr Thr Asp Ser Gln Leu Arg Trp Glu Tyr Cys Glu Ile Pro Ser Cys
        340                 345                 350

Glu Ser Ser Ala Ser Pro Asp Gln Ser Asp Ser Ser Val Pro Pro Glu
    355                 360                 365

Glu Gln Thr Pro Val Val Gln Glu Cys Tyr Gln Ser Asp Gly Gln Ser
370                 375                 380

Tyr Arg Gly Thr Ser Ser Thr Thr Ile Thr Gly Lys Lys Cys Gln Ser
385                 390                 395                 400

Trp Ala Ala Met Phe Pro His Arg His Ser Lys Thr Pro Glu Asn Phe
            405                 410                 415

Pro Asp Ala Gly Leu Glu Met Asn Tyr Cys Arg Asn Pro Asp Gly Asp
        420                 425                 430

Lys Gly Pro Trp Cys Tyr Thr Thr Asp Pro Ser Val Arg Trp Glu Tyr
    435                 440                 445

Cys Asn Leu Lys Arg Cys Ser Glu Thr Gly Gly Ser Val Val Glu Leu
450                 455                 460

Pro Thr Val Ser Gln Glu Pro Ser Gly Pro Ser Asp Ser Glu Thr Asp
465                 470                 475                 480

Cys Met Tyr Gly Asn Gly Lys Asp Tyr Arg Gly Lys Thr Ala Val Thr
            485                 490                 495

Ala Ala Gly Thr Pro Cys Gln Gly Trp Ala Ala Gln Glu Pro His Arg
        500                 505                 510

His Ser Ile Phe Thr Pro Gln Thr Asn Pro Arg Ala Gly Leu Glu Lys
    515                 520                 525

Asn Tyr Cys Arg Asn Pro Asp Gly Asp Val Asn Gly Pro Trp Cys Tyr
530                 535                 540

Thr Thr Asn Pro Arg Lys Leu Tyr Asp Tyr Cys Asp Ile Pro Leu Cys
545                 550                 555                 560

Ala Ser Ala Ser Ser Phe Glu Cys Gly Lys Pro Gln Val Glu Pro Lys
            565                 570                 575

Lys Cys Pro Gly Arg Val Val Gly Gly Cys Val Ala Asn Pro His Ser
        580                 585                 590

Trp Pro Trp Gln Ile Ser Leu Arg Thr Arg Phe Thr Gly Gln His Phe
    595                 600                 605

Cys Gly Gly Thr Leu Ile Ala Pro Glu Trp Val Leu Thr Ala Ala His
610                 615                 620

Cys Leu Glu Lys Ser Ser Arg Pro Glu Phe Tyr Lys Val Ile Leu Gly
625                 630                 635                 640

Ala His Glu Glu Tyr Ile Arg Gly Ser Asp Val Gln Glu Ile Ser Val
            645                 650                 655

Ala Lys Leu Ile Leu Glu Pro Asn Asn Arg Asp Ile Ala Leu Leu Lys
        660                 665                 670

Leu Ser Arg Pro Ala Thr Ile Thr Asp Lys Val Ile Pro Ala Cys Leu
    675                 680                 685

Pro Ser Pro Asn Tyr Met Val Ala Asp Arg Thr Ile Cys Tyr Ile Thr
690                 695                 700

Gly Trp Gly Glu Thr Gln Gly Thr Phe Gly Ala Gly Arg Leu Lys Glu
705                 710                 715                 720

```
Ala Gln Leu Pro Val Ile Glu Asn Lys Val Cys Asn Arg Val Glu Tyr
                725                 730                 735

Leu Asn Asn Arg Val Lys Ser Thr Glu Leu Cys Ala Gly Gln Leu Ala
            740                 745                 750

Gly Gly Val Asp Ser Cys Gln Gly Asp Ser Gly Gly Pro Leu Val Cys
            755                 760                 765

Phe Glu Lys Asp Lys Tyr Ile Leu Gln Gly Val Thr Ser Trp Gly Leu
        770                 775                 780

Gly Cys Ala Arg Pro Asn Lys Pro Gly Val Tyr Val Arg Val Ser Arg
785                 790                 795                 800

Phe Val Asp Trp Ile Glu Arg Glu Met Arg Asn Asn
                805                 810

<210> SEQ ID NO 12
<211> LENGTH: 812
<212> TYPE: PRT
<213> ORGANISM: Rattus norvegicus

<400> SEQUENCE: 12

Met Asp His Lys Glu Ile Ile Leu Leu Phe Leu Leu Phe Leu Lys Pro
1               5                   10                  15

Gly Gln Gly Asp Ser Leu Asp Gly Tyr Val Ser Thr Gln Gly Ala Ser
                20                  25                  30

Leu His Ser Leu Thr Lys Lys Gln Leu Ala Ala Gly Ser Ile Ala Asp
            35                  40                  45

Cys Leu Ala Lys Cys Glu Gly Glu Thr Asp Phe Ile Cys Arg Ser Phe
50                  55                  60

Gln Tyr His Ser Lys Glu Gln Cys Val Ile Met Ala Glu Asn Ser
65                  70                  75                  80

Lys Thr Ser Ser Ile Ile Arg Met Arg Asp Val Ile Leu Phe Glu Lys
                85                  90                  95

Arg Val Tyr Leu Ser Glu Cys Lys Thr Gly Ile Gly Lys Gly Tyr Arg
            100                 105                 110

Gly Thr Met Ser Lys Thr Lys Thr Gly Val Thr Cys Gln Lys Trp Ser
        115                 120                 125

Asp Thr Ser Pro His Val Pro Lys Tyr Ser Pro Ser Thr His Pro Ser
    130                 135                 140

Glu Gly Leu Glu Glu Asn Tyr Cys Arg Asn Pro Asp Asn Asp Glu Gln
145                 150                 155                 160

Gly Pro Trp Cys Tyr Thr Thr Asp Pro Asp Gln Arg Tyr Glu Tyr Cys
                165                 170                 175

Asn Ile Pro Glu Cys Glu Glu Glu Cys Met Tyr Cys Ser Gly Glu Lys
            180                 185                 190

Tyr Glu Gly Lys Ile Ser Lys Thr Met Ser Gly Leu Asp Cys Gln Ser
        195                 200                 205

Trp Asp Ser Gln Ser Pro His Ala His Gly Tyr Ile Pro Ala Lys Phe
    210                 215                 220

Pro Ser Lys Asn Leu Lys Met Asn Tyr Cys Arg Asn Pro Asp Gly Glu
225                 230                 235                 240

Pro Arg Pro Trp Cys Phe Thr Thr Asp Pro Asn Lys Arg Trp Glu Tyr
                245                 250                 255

Cys Asp Ile Pro Arg Cys Thr Thr Pro Pro Pro Pro Gly Pro Thr
            260                 265                 270

Tyr Gln Cys Leu Lys Gly Arg Gly Glu Asn Tyr Arg Gly Thr Val Ser
        275                 280                 285
```

```
Val Thr Ala Ser Gly Lys Thr Cys Gln Arg Trp Ser Glu Gln Thr Pro
            290                 295                 300
His Arg His Asn Arg Thr Pro Glu Asn Phe Pro Cys Lys Asn Leu Glu
305                 310                 315                 320
Glu Asn Tyr Cys Arg Asn Pro Asp Gly Glu Thr Ala Pro Trp Cys Tyr
                325                 330                 335
Thr Thr Asp Ser Gln Leu Arg Trp Glu Tyr Cys Glu Ile Pro Ser Cys
            340                 345                 350
Gly Ser Ser Val Ser Pro Asp Gln Ser Asp Ser Ser Val Leu Pro Glu
        355                 360                 365
Gln Thr Pro Val Val Gln Glu Cys Tyr Gln Gly Asn Gly Lys Ser Tyr
370                 375                 380
Arg Gly Thr Ser Ser Thr Thr Asn Thr Gly Lys Lys Cys Gln Ser Trp
385                 390                 395                 400
Val Ser Met Thr Pro His Ser His Ser Lys Thr Pro Ala Asn Phe Pro
                405                 410                 415
Asp Ala Gly Leu Glu Met Asn Tyr Cys Arg Asn Pro Asp Asn Asp Gln
            420                 425                 430
Arg Gly Pro Trp Cys Phe Thr Thr Asp Pro Ser Val Arg Trp Glu Tyr
435                 440                 445
Cys Asn Leu Lys Arg Cys Ser Glu Thr Gly Gly Val Ala Glu Ser
450                 455                 460
Ala Ile Val Pro Gln Val Pro Ser Ala Pro Gly Thr Ser Glu Thr Asp
465                 470                 475                 480
Cys Met Tyr Gly Asn Gly Lys Glu Tyr Arg Gly Lys Thr Ala Val Thr
                485                 490                 495
Ala Ala Gly Thr Pro Cys Gln Gly Trp Ala Ala Gln Glu Pro His Ser
            500                 505                 510
His Arg Ile Phe Thr Pro Gln Thr Asn Pro Arg Ala Gly Leu Glu Lys
        515                 520                 525
Asn Tyr Cys Arg Asn Pro Asp Gly Asp Val Asn Gly Pro Trp Cys Tyr
530                 535                 540
Thr Met Asn Pro Arg Lys Leu Tyr Asp Tyr Cys Asn Ile Pro Leu Cys
545                 550                 555                 560
Ala Ser Leu Ser Ser Phe Glu Cys Gly Lys Pro Gln Val Glu Pro Lys
                565                 570                 575
Lys Cys Pro Gly Arg Val Val Gly Gly Cys Val Ala Asn Pro His Ser
            580                 585                 590
Trp Pro Trp Gln Ile Ser Leu Arg Thr Arg Phe Ser Gly Gln His Phe
        595                 600                 605
Cys Gly Gly Thr Leu Ile Ser Pro Glu Trp Val Leu Thr Ala Ala His
610                 615                 620
Cys Leu Glu Lys Ser Ser Arg Pro Glu Phe Tyr Lys Val Ile Leu Gly
625                 630                 635                 640
Ala His Glu Glu Arg Ile Leu Gly Ser Asp Val Gln Gln Ile Ala Val
                645                 650                 655
Thr Lys Leu Val Leu Glu Pro Asn Asp Ala Asp Ile Ala Leu Leu Lys
            660                 665                 670
Leu Ser Arg Pro Ala Thr Ile Thr Asp Asn Val Ile Pro Ala Cys Leu
        675                 680                 685
Pro Ser Pro Asn Tyr Val Val Ala Asp Arg Thr Leu Cys Tyr Ile Thr
690                 695                 700
```

Gly Trp Gly Glu Thr Lys Gly Thr Pro Gly Ala Gly Arg Leu Lys Glu
705                 710                 715                 720

Ala Gln Leu Pro Val Ile Glu Asn Lys Val Cys Asn Arg Ala Glu Tyr
            725                 730                 735

Leu Asn Asn Arg Val Lys Ser Thr Glu Leu Cys Ala Gly His Leu Ala
            740                 745                 750

Gly Gly Ile Asp Ser Cys Gln Gly Asp Ser Gly Gly Pro Leu Val Cys
            755                 760                 765

Phe Glu Lys Asp Lys Tyr Ile Leu Gln Gly Val Thr Ser Trp Gly Leu
        770                 775                 780

Gly Cys Ala Arg Pro Asn Lys Pro Gly Val Tyr Val Arg Val Ser Arg
785                 790                 795                 800

Tyr Val Asn Trp Ile Glu Arg Glu Met Arg Asn Asp
                805                 810

<210> SEQ ID NO 13
<211> LENGTH: 811
<212> TYPE: PRT
<213> ORGANISM: Erinaceus europaeus

<400> SEQUENCE: 13

Met Gln Arg Lys Glu Leu Val Leu Leu Phe Leu Leu Phe Leu Gln Pro
1               5                   10                  15

Gly His Gly Ile Pro Leu Asp Asp Tyr Val Thr Thr Gln Gly Ala Ser
            20                  25                  30

Leu Ser Ser Ser Thr Lys Lys Gln Leu Ser Val Gly Ser Thr Glu Glu
        35                  40                  45

Cys Ala Val Lys Cys Glu Lys Glu Thr Ser Phe Ile Cys Arg Ser Phe
50                  55                  60

Gln Tyr His Ser Lys Glu Gln Gln Cys Val Ile Met Ala Glu Asn Ser
65                  70                  75                  80

Lys Ser Thr Pro Val Leu Arg Met Arg Asp Val Ile Leu Phe Glu Lys
                85                  90                  95

Lys Met Tyr Leu Ser Glu Cys Lys Val Gly Asn Gly Lys Tyr Tyr Arg
            100                 105                 110

Gly Thr Val Ser Lys Thr Lys Thr Gly Leu Thr Cys Gln Lys Trp Ser
        115                 120                 125

Ala Glu Thr Pro His Lys Pro Arg Phe Ser Pro Asp Glu Asn Pro Ser
    130                 135                 140

Glu Gly Leu Asp Gln Asn Tyr Cys Arg Asn Pro Asp Asn Asp Pro Lys
145                 150                 155                 160

Gly Pro Trp Cys Tyr Thr Met Asp Pro Glu Val Arg Tyr Glu Tyr Cys
                165                 170                 175

Glu Ile Ile Gln Cys Glu Asp Glu Cys Met His Cys Ser Gly Gln Asn
            180                 185                 190

Tyr Val Gly Lys Ile Ser Arg Thr Met Ser Gly Leu Glu Cys Gln Pro
        195                 200                 205

Trp Asp Ser Gln Ile Pro His Pro His Gly Phe Ile Pro Ser Lys Phe
    210                 215                 220

Pro Ser Lys Asn Leu Lys Met Asn Tyr Cys Arg Asn Pro Asp Gly Glu
225                 230                 235                 240

Pro Arg Pro Trp Cys Phe Thr Met Asp Arg Asn Lys Arg Trp Glu Tyr
                245                 250                 255

Cys Asp Ile Pro Arg Cys Thr Thr Pro Pro Pro Ser Gly Pro Thr
            260                 265                 270

```
Tyr Gln Cys Leu Met Gly Asn Gly Glu His Tyr Gln Gly Asn Val Ala
            275                 280                 285
Val Thr Val Ser Gly Leu Thr Cys Gln Arg Trp Gly Glu Gln Ser Pro
    290                 295                 300
His Arg His Asp Arg Thr Pro Glu Asn Tyr Pro Cys Lys Asn Leu Asp
305                 310                 315                 320
Glu Asn Tyr Cys Arg Asn Pro Asp Gly Glu Pro Ala Pro Trp Cys Phe
                325                 330                 335
Thr Thr Asn Ser Ser Val Arg Trp Glu Phe Cys Lys Ile Pro Asp Cys
            340                 345                 350
Val Ser Ser Ala Ser Glu Thr Glu His Ser Asp Ala Pro Val Ile Val
            355                 360                 365
Pro Pro Glu Gln Thr Pro Val Val Gln Glu Cys Tyr Gln Gly Asn Gly
370                 375                 380
Gln Ser Tyr Arg Gly Thr Ser Ser Thr Thr Ile Thr Gly Lys Lys Cys
385                 390                 395                 400
Gln Pro Trp Thr Ser Met Arg Pro His Arg His Ser Lys Thr Pro Glu
                405                 410                 415
Asn Tyr Pro Asp Ala Asp Leu Thr Met Asn Tyr Cys Arg Asn Pro Asp
                420                 425                 430
Gly Asp Lys Gly Pro Trp Cys Tyr Thr Thr Asp Pro Ser Val Arg Trp
            435                 440                 445
Glu Phe Cys Asn Leu Lys Lys Cys Ser Gly Thr Glu Met Ser Ala Thr
            450                 455                 460
Asn Ser Ser Pro Val Gln Val Ser Ser Ala Ser Glu Ser Ser Glu Gln
465                 470                 475                 480
Asp Cys Ile Ile Asp Asn Gly Lys Gly Tyr Arg Gly Thr Lys Ala Thr
                485                 490                 495
Thr Gly Ala Gly Thr Pro Cys Gln Ala Trp Ala Ala Gln Glu Pro His
            500                 505                 510
Arg His Ser Ile Phe Thr Pro Glu Thr Asn Pro Arg Ala Asp Leu Gln
            515                 520                 525
Glu Asn Tyr Cys Arg Asn Pro Asp Gly Asp Ala Asn Gly Pro Trp Cys
            530                 535                 540
Tyr Thr Thr Asn Pro Arg Lys Leu Phe Asp Tyr Cys Asp Ile Pro His
545                 550                 555                 560
Cys Val Ser Pro Ser Ser Ala Asp Cys Gly Lys Pro Lys Val Glu Pro
                565                 570                 575
Lys Lys Cys Pro Gly Arg Val Val Gly Gly Cys Val Ala Asn Pro His
                580                 585                 590
Ser Trp Pro Trp Gln Val Ser Leu Arg Arg Phe Gly Gln His Phe Cys
            595                 600                 605
Gly Gly Thr Leu Ile Ser Pro Glu Trp Val Val Thr Ala Ala His Cys
            610                 615                 620
Leu Glu Lys Phe Ser Asn Pro Ala Ile Tyr Lys Val Val Leu Gly Ala
625                 630                 635                 640
His Gln Glu Thr Arg Leu Glu Arg Asp Val Gln Ile Lys Gly Val Thr
                645                 650                 655
Lys Met Phe Leu Glu Pro Tyr Arg Ala Asp Ile Ala Leu Leu Lys Leu
                660                 665                 670
Ser Ser Pro Ala Ile Ile Thr Asp Lys Ile Ile Pro Ala Cys Leu Pro
            675                 680                 685
```

Asn Ser Asn Tyr Met Val Ala Asp Arg Ser Leu Cys Tyr Ile Thr Gly
    690                 695                 700

Trp Gly Glu Thr Lys Gly Thr Tyr Gly Ala Gly Leu Leu Lys Glu Ala
705                 710                 715                 720

Gln Leu Pro Val Ile Glu Asn Lys Val Cys Asn Arg Gln Glu Leu Leu
                725                 730                 735

Asn Gly Arg Val Arg Ser Thr Glu Leu Cys Ala Gly His Leu Ala Gly
            740                 745                 750

Gly Val Asp Ser Cys Gln Gly Asp Ser Gly Gly Pro Leu Val Cys Phe
        755                 760                 765

Glu Lys Asp Arg Tyr Ile Leu Gln Gly Val Thr Ser Trp Gly Leu Gly
770                 775                 780

Cys Ala Arg Pro Asn Lys Pro Gly Val Tyr Val Arg Val Ser Arg Tyr
785                 790                 795                 800

Val Ser Trp Leu Gln Asp Val Met Arg Asn Asn
                805                 810

<210> SEQ ID NO 14
<211> LENGTH: 780
<212> TYPE: PRT
<213> ORGANISM: Oryctolagus cuniculus

<400> SEQUENCE: 14

Met Glu Gln Arg Ala Val Val Leu Leu Leu Leu Leu Leu Lys Pro
1               5                   10                  15

Gly Gln Ala Glu Pro Leu Asp Asp Tyr Val Asn Thr Gln Gly Ala Ser
            20                  25                  30

Leu Phe Ser Phe Thr Lys Lys Gln Leu Gly Ala Ala Ser Ile Ala Glu
        35                  40                  45

Cys Ala Ala Arg Cys Glu Ala Glu Thr Glu Phe Thr Cys Arg Ser Phe
    50                  55                  60

Gln Tyr His Ser Lys Glu Gln Gln Cys Val Val Met Ala Glu Asn Ser
65                  70                  75                  80

Lys Ser Ser Ala Ile Ile Arg Arg Arg Asp Val Val Leu Phe Glu Lys
                85                  90                  95

Arg Met Tyr Leu Ser Glu Cys Lys Ile Gly Asn Gly Arg Ser Tyr Arg
                100                 105                 110

Gly Thr Lys Ser Lys Thr Lys Thr Gly Phe Thr Cys Gln Lys Trp Ser
            115                 120                 125

Ser Ser Tyr Pro His Lys Pro Asn Phe Thr Pro Lys Lys Tyr Pro Ala
        130                 135                 140

Glu Gly Leu Glu Glu Asn Tyr Cys Arg Asn Pro Asp Asn Asp Glu Gln
145                 150                 155                 160

Gly Pro Trp Cys Tyr Thr Thr Asn Pro Asp Glu Arg Phe Asp Tyr Cys
                165                 170                 175

Asp Ile Pro Glu Cys Glu Asp Glu Cys Met His Cys Ser Gly Glu Asn
                180                 185                 190

Tyr Glu Gly Lys Ile Ser Lys Thr Met Ser Gly Ile Glu Cys Gln Ala
            195                 200                 205

Trp Asp Ser Gln Ser Pro His Ala His Gly Tyr Ile Pro Ser Lys Phe
        210                 215                 220

Pro Asn Lys Asn Leu Lys Lys Asn Tyr Cys Arg Asn Pro Asp Gly Glu
225                 230                 235                 240

Pro Arg Pro Trp Cys Phe Thr Met Asp Pro Lys Lys Arg Trp Glu Leu
                245                 250                 255

-continued

Cys Asp Ile Pro Arg Cys Thr Pro Pro Pro Ser Gly Pro Thr
         260              265          270

His Gln Cys Leu Lys Gly Arg Gly Glu Ser Tyr Arg Gly Lys Val Ala
            275              280          285

Arg Thr Lys Ser Gly Leu Thr Cys Gln Arg Trp Ser Glu Gln Thr Pro
290              295              300

His Leu His Asn Arg Thr Pro Glu Asn Phe Pro Cys Lys Asp Leu Asp
305              310              315              320

Glu Asn Tyr Cys Arg Asn Pro Asp Gly Glu Ser Ala Pro Trp Cys Tyr
                325              330              335

Thr Thr Asp Ser Lys Val Arg Trp Glu His Cys Asp Ile Pro Ser Cys
            340              345              350

Ala Ser Ser Pro Thr Ser Val Glu Pro Leu Asp Ala Pro Ala Pro Pro
            355              360              365

Glu Glu Thr Pro Val Val Gln Glu Cys Tyr Gln Gly Asn Gly Gln Ser
        370              375              380

Tyr Arg Gly Thr Ser Ser Thr Thr Ile Thr Gly Arg Lys Cys Gln Ser
385              390              395              400

Trp Leu Ser Met Thr Pro His Arg His Gln Arg Thr Pro Gln Asn Tyr
                405              410              415

Pro Asn Ala Asp Leu Thr Met Asn Tyr Cys Arg Asn Pro Asp Asp Asp
            420              425              430

Ile Arg Pro Trp Cys Tyr Thr Thr Asp Pro Ser Val Arg Trp Glu Tyr
        435              440              445

Cys Asn Leu Arg Arg Cys Ser Glu Pro Ala Ala Ser Pro Ala Ala Thr
            450              455              460

Val Pro Thr Ala Gln Leu Pro Arg Pro Glu Ala Thr Phe Glu Pro Asp
465              470              475              480

Cys Met Phe Gly Asn Gly Lys Gly Tyr Arg Gly Lys Lys Ala Thr Thr
                485              490              495

Ala Asp Gly Thr Pro Cys Gln Gly Trp Ala Ala Gln Glu Pro His Arg
            500              505              510

His Asn Ile Phe Thr Pro Glu Thr Asn Pro Arg Ala Gly Leu Glu Arg
            515              520              525

Asn Tyr Cys Arg Asn Pro Asp Gly Asp Thr Asn Gly Pro Trp Cys Tyr
        530              535              540

Thr Met Asn Pro Arg Lys Leu Tyr Asp Tyr Cys Asp Val Pro Gln Cys
545              550              555              560

Ala Ser Ser Ser Tyr Asp Cys Gly Lys Pro Lys Val Glu Pro Lys
                565              570              575

Lys Cys Pro Gly Arg Val Val Gly Gly Cys Val Ala Asn Pro His Ser
            580              585              590

Trp Pro Trp Gln Ile Ser Leu Arg Thr Arg Thr Gly Gln His Phe Cys
            595              600              605

Gly Gly Thr Leu Ile Ala Pro Glu Trp Val Leu Thr Ala Ala His Cys
            610              615              620

Leu Glu Lys Tyr Pro Arg Pro Ser Ala Tyr Arg Val Ile Leu Gly Ala
625              630              635              640

His Lys Glu Val Asn Leu Glu Leu Asp Val Gln Asp Ile Asp Val Ala
                645              650              655

Lys Leu Phe Leu Glu Pro Ser Arg Ala Asp Ile Ala Leu Met Lys Leu
            660              665              670

```
Ser Ser Leu Glu Trp Ala Trp Thr Tyr Gly Ala Gly Leu Lys Glu
        675                 680                 685

Ala Gln Leu Pro Val Ile Glu Asn Lys Val Cys Asn Arg Phe Glu Tyr
    690                 695                 700

Leu Asn Gly Arg Val Arg Ser Thr Glu Leu Cys Ala Gly His Leu Ala
705                 710                 715                 720

Gly Gly Thr Asp Ser Cys Gln Gly Asp Ser Gly Gly Pro Leu Val Cys
                725                 730                 735

Phe Glu Lys Asp Lys Tyr Ile Leu Gln Gly Val Thr Ser Trp Gly Leu
            740                 745                 750

Gly Cys Ala Arg Pro Asn Lys Pro Gly Val Tyr Val Arg Val Ser Arg
    755                 760                 765

Phe Val Asp Trp Ile Glu Arg Thr Met Arg Asn Asn
    770                 775                 780

<210> SEQ ID NO 15
<211> LENGTH: 827
<212> TYPE: PRT
<213> ORGANISM: Pan troglodytes

<400> SEQUENCE: 15

Met Glu His Lys Glu Val Val Leu Leu Leu Leu Phe Leu Lys Ser
1               5                   10                  15

Gly Gln Gly Glu Pro Leu Asp Asp Tyr Val Asn Thr Gln Gly Ala Ser
            20                  25                  30

Leu Phe Ser Val Thr Lys Lys Gln Leu Gly Ala Gly Ser Ile Glu Glu
        35                  40                  45

Cys Ala Ala Lys Cys Glu Glu Asp Lys Glu Phe Thr Cys Arg Tyr Phe
    50                  55                  60

His Cys Arg Cys Thr Tyr Pro Glu Ile Cys Asn Ser Asp Gly Lys Ala
65                  70                  75                  80

Phe Gln Tyr His Ser Lys Glu Gln Gln Cys Val Ile Met Ala Glu Asn
            85                  90                  95

Arg Lys Ser Ser Ile Ile Ile Arg Met Arg Asp Val Val Leu Phe Glu
            100                 105                 110

Lys Lys Val Tyr Leu Ser Glu Cys Lys Thr Gly Asn Gly Lys Asn Tyr
        115                 120                 125

Arg Gly Thr Met Ser Lys Thr Lys Asn Gly Ile Thr Cys Gln Lys Trp
    130                 135                 140

Ser Ser Thr Ser Pro His Arg Pro Arg Phe Ser Pro Ala Thr His Pro
145                 150                 155                 160

Ser Glu Gly Leu Glu Glu Asn Tyr Cys Arg Asn Pro Asp Asn Asp Pro
            165                 170                 175

Gln Gly Pro Trp Cys Tyr Thr Thr Asp Pro Glu Lys Arg Tyr Asp Tyr
        180                 185                 190

Cys Asp Ile Leu Glu Cys Glu Glu Cys Met His Cys Ser Gly Glu
    195                 200                 205

Asn Tyr Asp Gly Lys Ile Ser Lys Thr Met Ser Gly Leu Glu Cys Gln
    210                 215                 220

Ala Trp Asp Ser Gln Ser Pro His Ala His Gly Tyr Ile Pro Ser Lys
225                 230                 235                 240

Phe Pro Asn Lys Asn Leu Lys Lys Asn Tyr Cys Arg Asn Pro Asp Gly
            245                 250                 255

Glu Leu Arg Pro Trp Cys Phe Thr Thr Asp Pro Asn Lys Arg Trp Glu
            260                 265                 270
```

-continued

```
Leu Cys Asp Ile Pro Arg Cys Thr Thr Pro Pro Ser Ser Gly Pro
        275                 280                 285

Thr Tyr Gln Cys Leu Lys Gly Thr Gly Glu Asn Tyr Arg Gly Asn Val
    290                 295                 300

Ala Val Thr Val Ser Gly His Thr Cys Gln His Trp Ser Ala Gln Thr
305                 310                 315                 320

Pro His Thr His Asn Arg Thr Pro Glu Asn Phe Pro Cys Lys Asn Leu
                325                 330                 335

Asp Glu Asn Tyr Cys Arg Asn Pro Asp Gly Lys Arg Ala Pro Trp Cys
            340                 345                 350

His Thr Thr Asn Ser Gln Val Arg Trp Glu Tyr Cys Lys Ile Pro Ser
        355                 360                 365

Cys Asp Ser Ser Leu Val Ser Thr Glu Gln Leu Ala Pro Thr Ala Pro
    370                 375                 380

Pro Glu Leu Thr Pro Val Val Gln Asp Cys Tyr His Gly Asp Gly Gln
385                 390                 395                 400

Ser Tyr Arg Gly Thr Ser Ser Thr Thr Thr Thr Gly Lys Lys Cys Gln
                405                 410                 415

Ser Trp Ser Ser Met Thr Pro His Arg His Gln Lys Thr Pro Glu Asn
            420                 425                 430

Tyr Pro Asn Ala Gly Leu Thr Met Asn Tyr Cys Arg Asn Pro Asp Ala
        435                 440                 445

Asp Lys Gly Pro Trp Cys Phe Thr Thr Asp Pro Ser Val Arg Trp Glu
    450                 455                 460

Tyr Cys Asn Leu Lys Lys Cys Ser Gly Thr Glu Ala Ser Val Val Ala
465                 470                 475                 480

Pro Pro Pro Val Val Gln Leu Pro Asn Val Glu Thr Pro Ser Glu Glu
                485                 490                 495

Asp Cys Met Phe Gly Asn Gly Lys Gly Tyr Arg Gly Lys Arg Ala Thr
            500                 505                 510

Thr Val Thr Gly Thr Pro Cys Gln Asp Trp Ala Ala Gln Glu Pro His
        515                 520                 525

Arg His Ser Ile Phe Thr Pro Glu Thr Asn Pro Arg Ala Gly Leu Glu
    530                 535                 540

Lys Asn Tyr Cys Arg Asn Pro Asp Gly Asp Val Gly Gly Pro Trp Cys
545                 550                 555                 560

Tyr Thr Thr Asn Pro Arg Lys Leu Tyr Asp Tyr Cys Asp Val Pro Gln
                565                 570                 575

Cys Ala Ser Pro Ser Phe Asp Cys Gly Lys Pro Gln Val Glu Pro Lys
            580                 585                 590

Lys Cys Pro Gly Arg Val Val Gly Gly Cys Val Ala His Pro His Ser
        595                 600                 605

Trp Pro Trp Gln Val Ser Leu Arg Thr Arg Leu Gly Met His Phe Cys
    610                 615                 620

Gly Gly Thr Leu Ile Ser Pro Glu Trp Val Leu Thr Ala Ala His Cys
625                 630                 635                 640

Leu Glu Lys Ser Pro Arg Pro Ser Ser Tyr Lys Val Ile Leu Gly Ala
                645                 650                 655

His Gln Glu Val Lys Leu Glu Pro His Val Gln Glu Ile Glu Val Ser
            660                 665                 670

Arg Leu Phe Leu Glu Pro Thr Arg Thr Asp Ile Ala Leu Leu Lys Leu
        675                 680                 685
```

```
Ser Ser Pro Ala Ile Ile Thr Asp Lys Val Ile Pro Ala Cys Leu Pro
    690                 695                 700
Ser Pro Asn Tyr Val Val Ala Asp Arg Thr Glu Cys Phe Ile Thr Gly
705                 710                 715                 720
Trp Gly Glu Thr Gln Gly Thr Phe Gly Ala Gly Leu Leu Lys Glu Ala
                    725                 730                 735
Gln Leu Pro Val Ile Glu Asn Lys Val Cys Asn Arg Asn Glu Phe Leu
            740                 745                 750
Asn Gly Arg Val Lys Ser Thr Glu Leu Cys Ala Gly His Leu Ala Gly
        755                 760                 765
Gly Thr Asp Ser Cys Gln Gly Asp Ser Gly Pro Leu Val Cys Phe
770                 775                 780
Glu Lys Asp Lys Tyr Ile Leu Gln Gly Val Thr Ser Trp Gly Leu Gly
785                 790                 795                 800
Cys Ala Arg Pro Asn Lys Pro Gly Val Tyr Val Arg Val Ser Arg Phe
                805                 810                 815
Val Thr Trp Ile Glu Gly Val Met Arg Asn Asn
                820                 825

<210> SEQ ID NO 16
<211> LENGTH: 769
<212> TYPE: PRT
<213> ORGANISM: Ailuropoda melanoleuca

<400> SEQUENCE: 16

Phe Val Arg Arg Ser Phe Glu Tyr His Ser Lys Glu Gln Gln Cys Ala
1               5                   10                  15
Ile Met Ala Glu Asn Ser Lys Ser Ser Ala Val Phe Arg Met Arg Asp
            20                  25                  30
Val Ile Leu Phe Gln Lys Arg Ile Tyr Leu Ser Glu Cys Lys Thr Gly
        35                  40                  45
Asn Gly Lys Thr Tyr Arg Gly Thr Met Ser Lys Thr Lys Asn Gly Val
    50                  55                  60
Ala Cys Gln Lys Trp Ser Asp Thr Phe Pro His Lys Pro Asn Tyr Thr
65                  70                  75                  80
Pro Glu Lys His Pro Leu Glu Gly Leu Glu Glu Asn Tyr Cys Arg Asn
                85                  90                  95
Pro Asp Asn Asp Glu Lys Gly Pro Trp Cys Tyr Thr Thr Asp Pro Asn
            100                 105                 110
Gln Arg Phe Asp Tyr Cys Ser Ile Pro Gln Cys Glu Asp Glu Cys Met
        115                 120                 125
His Cys Ser Gly Glu Asn Tyr Glu Gly Lys Val Ser Lys Thr Lys Ser
    130                 135                 140
Gly Leu Glu Cys Gln Ala Trp Asn Ser Gln Thr Pro His Ala His Gly
145                 150                 155                 160
Tyr Ile Pro Ser Lys Phe Pro Asn Lys Asn Leu Lys Met Asn Tyr Cys
                165                 170                 175
Arg Asn Pro Asp Gly Glu Pro Arg Pro Trp Cys Phe Thr Met Asp Pro
            180                 185                 190
Asn Lys Arg Trp Glu Phe Cys Asp Ile Pro Arg Cys Thr Thr Pro Pro
        195                 200                 205
Pro Pro Ser Gly Pro Thr Tyr Gln Cys Leu Lys Gly Lys Gly Glu Asn
    210                 215                 220
Tyr Arg Gly Lys Val Ser Val Thr Ala Ser Gly His Thr Cys Gln Arg
225                 230                 235                 240
```

```
Trp Ser Glu Gln Thr Pro His Lys His Asn Arg Thr Pro Glu Asn Phe
                245                 250                 255

Pro Cys Lys Asn Leu Asp Glu Asn Tyr Cys Arg Asn Pro Asp Gly Glu
            260                 265                 270

Ser Ala Pro Trp Cys Tyr Thr Thr Asp Ser Glu Val Arg Trp Glu His
        275                 280                 285

Cys Ser Ile Pro Ser Cys Glu Ser Ser Pro Leu Thr Leu Asp Ser Leu
    290                 295                 300

Asp Thr Pro Ala Ser Ile Pro Pro Glu Gln Thr Pro Val Val Gln Glu
305                 310                 315                 320

Cys Tyr Gln Gly Asn Gly Gln Thr Tyr Arg Gly Thr Ser Ser Thr Thr
                325                 330                 335

Ile Thr Gly Lys Lys Cys Gln Pro Trp Ser Ser Met Ser Pro His Arg
            340                 345                 350

His Glu Lys Thr Pro Glu Arg Phe Pro Asn Ala Gly Leu Thr Met Asn
        355                 360                 365

Tyr Cys Arg Asn Pro Asp Gly Asp Lys Ser Pro Trp Cys Tyr Thr Thr
    370                 375                 380

Asp Pro Ser Val Arg Trp Glu Phe Cys Asn Leu Lys Lys Cys Leu Asp
385                 390                 395                 400

Thr Glu Glu Ser Gly Thr Ser Ser Pro Thr Val Pro Gln Val Pro Ser
                405                 410                 415

Gly Glu Glu Pro Ser Glu Thr Asp Cys Met Phe Gly Asn Gly Lys Gly
            420                 425                 430

Tyr Arg Gly Lys Lys Ala Thr Thr Val Leu Gly Ile Pro Cys Gln Glu
        435                 440                 445

Trp Thr Ala Gln Glu Pro His Lys His Ser Ile Phe Thr Pro Glu Thr
    450                 455                 460

Asn Pro Arg Ala Glu His Leu Leu Cys Pro Thr Cys Leu Val Pro Ser
465                 470                 475                 480

Val Pro Thr Val Phe Phe Phe Phe Phe Phe Phe Leu Phe Leu Asp
                485                 490                 495

Val Asn Gly Pro Trp Cys Tyr Thr Thr Asn Pro Arg Lys Leu Phe Asp
            500                 505                 510

Tyr Cys Asp Ile Pro Gln Cys Ala Ser Gly Ser Phe Asp Cys Gly Lys
    515                 520                 525

Pro Gln Val Glu Pro Lys Lys Cys Pro Gly Arg Val Val Gly Gly Cys
530                 535                 540

Val Ala Asn Pro His Ser Trp Pro Trp Gln Ile Ser Leu Arg Thr Arg
545                 550                 555                 560

Phe Gly Gln His Phe Cys Gly Gly Thr Leu Ile Ser Pro Glu Trp Val
                565                 570                 575

Leu Thr Ala Ala His Cys Leu Glu Arg Ser Pro Arg Pro Ala Ala Tyr
            580                 585                 590

Lys Val Ile Leu Gly Ala His Arg Glu Phe Asn Leu Glu Ser Asp Val
        595                 600                 605

Gln Glu Ile Glu Val Ser Lys Leu Phe Leu Glu Pro Thr His Ala Asp
    610                 615                 620

Ile Ala Leu Ile Lys Leu Gln Ser Pro Ala Val Leu Thr Ser Lys Val
625                 630                 635                 640

Ile Pro Ala Cys Leu Pro Ser Pro Asn Tyr Val Val Ala Asp Arg Thr
                645                 650                 655
```

-continued

```
Leu Cys Tyr Ile Thr Gly Trp Gly Glu Thr Gln Gly Thr Phe Gly Val
            660                 665                 670

Gly Leu Leu Lys Glu Ala Gln Leu Pro Val Ile Glu Asn Lys Val Cys
        675                 680                 685

Asn Arg Tyr Glu Tyr Leu Asn Gly Lys Val Lys Ser Thr Glu Leu Cys
    690                 695                 700

Ala Gly Asn Leu Ala Gly Gly Thr Asp Ser Cys Gln Gly Asp Ser Gly
705                 710                 715                 720

Gly Pro Leu Val Cys Phe Glu Lys Asp Lys Tyr Ile Leu Gln Gly Val
                725                 730                 735

Thr Ser Trp Gly Leu Gly Cys Ala Arg Pro Asn Lys Pro Gly Val Tyr
            740                 745                 750

Val Arg Val Ser Arg Phe Val Thr Trp Ile Glu Glu Ile Met Arg Asn
        755                 760                 765

Asn
```

<210> SEQ ID NO 17
<211> LENGTH: 334
<212> TYPE: PRT
<213> ORGANISM: Papio hamadryas

<400> SEQUENCE: 17

```
Ile Arg Leu Asp Cys Met Phe Gly Asn Gly Lys Arg Tyr Arg Gly Lys
1               5                   10                  15

Lys Ala Thr Thr Val Thr Gly Thr Pro Cys Gln Glu Trp Ala Ala Lys
            20                  25                  30

Glu Pro His Ser His Leu Ile Phe Thr Pro Glu Thr Tyr Pro Arg Ala
        35                  40                  45

Gly Leu Glu Lys Asn Tyr Cys Arg Asn Pro Asp Gly Asp Val Gly Gly
    50                  55                  60

Pro Trp Cys Tyr Thr Thr Asn Pro Arg Lys Leu Tyr Asp Tyr Cys Asp
65                  70                  75                  80

Val Pro Gln Cys Ala Ser Ser Phe Asp Cys Gly Lys Pro Gln Val
                85                  90                  95

Glu Pro Lys Lys Cys Pro Gly Arg Val Val Gly Gly Cys Val Ala His
            100                 105                 110

Ala His Ser Trp Pro Trp Gln Val Ser Leu Arg Thr Arg Phe Gly Met
        115                 120                 125

His Phe Cys Gly Gly Thr Leu Ile Ser Pro Glu Trp Val Leu Thr Ala
    130                 135                 140

Ala His Cys Leu Glu Lys Ser Pro Arg Pro Ser Phe Tyr Lys Val Ile
145                 150                 155                 160

Leu Gly Ala His Gln Glu Val Arg Leu Glu Pro His Val Gln Glu Ile
                165                 170                 175

Glu Val Ser Lys Met Phe Ser Glu Pro Ala Gly Ala Asp Ile Ala Leu
            180                 185                 190

Leu Lys Leu Ser Ser Pro Ala Ile Ile Thr Asp Lys Val Ile Pro Ala
        195                 200                 205

Cys Leu Pro Ser Pro Asn Tyr Val Val Ala Asp Arg Thr Glu Cys Phe
    210                 215                 220

Ile Thr Gly Trp Gly Glu Thr Gln Gly Thr Tyr Gly Ala Gly Leu Leu
225                 230                 235                 240

Lys Glu Ala Arg Leu Pro Val Ile Glu Asn Lys Val Cys Asn Arg Tyr
                245                 250                 255
```

```
Glu Phe Leu Asn Gly Arg Val Lys Ser Thr Glu Leu Cys Ala Gly His
                260                 265                 270

Leu Ala Gly Gly Thr Asp Ser Cys Gln Gly Asp Ser Gly Pro Leu
        275                 280                 285

Val Cys Phe Glu Lys Asp Lys Tyr Ile Leu Gln Gly Val Thr Ser Trp
    290                 295                 300

Gly Leu Gly Cys Ala Arg Pro Asn Lys Pro Gly Val Tyr Val Arg Val
305                 310                 315                 320

Ser Arg Phe Val Thr Trp Ile Glu Gly Val Met Arg Asn Asn
                325                 330

<210> SEQ ID NO 18
<211> LENGTH: 343
<212> TYPE: PRT
<213> ORGANISM: Ovis aries

<400> SEQUENCE: 18

Ala Pro Gln Ala Pro Ser Val Glu Asn Pro Glu Ala Asp Cys Met
1               5                   10                  15

Leu Gly Ile Gly Lys Gly Tyr Arg Gly Lys Lys Ala Thr Thr Val Ala
                20                  25                  30

Gly Val Pro Cys Gln Glu Trp Ala Ala Gln Glu Pro His Arg His Gly
            35                  40                  45

Ile Phe Thr Pro Glu Thr Asn Pro Arg Ala Gly Leu Glu Lys Asn Tyr
        50                  55                  60

Cys Arg Asn Pro Asp Gly Asp Val Asn Gly Pro Trp Cys Tyr Thr Thr
65                  70                  75                  80

Asn Pro Arg Lys Leu Phe Asp Tyr Cys Asp Ile Pro Gln Cys Glu Ser
                85                  90                  95

Ser Phe Asp Cys Gly Lys Pro Lys Val Glu Pro Lys Lys Cys Pro Ala
                100                 105                 110

Arg Val Val Gly Gly Cys Val Ala Thr Pro His Ser Trp Pro Trp Gln
            115                 120                 125

Val Ser Leu Arg Arg Arg Ser Arg Glu His Phe Cys Gly Gly Thr Leu
    130                 135                 140

Ile Ser Pro Glu Trp Val Leu Thr Ala Ala His Cys Leu Asp Ser Ile
145                 150                 155                 160

Leu Gly Pro Ser Phe Tyr Thr Val Ile Leu Gly Ala His Tyr Glu Met
                165                 170                 175

Ala Arg Glu Ala Ser Val Gln Glu Ile Pro Val Ser Arg Leu Phe Leu
            180                 185                 190

Glu Pro Ser Arg Ala Asp Ile Ala Leu Leu Lys Leu Ser Ser Pro Ala
        195                 200                 205

Val Ile Thr Asp Glu Val Ile Pro Ala Cys Leu Pro Ser Pro Asn Tyr
    210                 215                 220

Val Val Ala Asp Lys Thr Val Cys Tyr Ile Thr Gly Trp Gly Glu Thr
225                 230                 235                 240

Gln Gly Thr Phe Gly Val Gly Arg Leu Lys Glu Ala Arg Leu Pro Val
                245                 250                 255

Ile Glu Asn Lys Val Cys Asn Arg Tyr Glu Tyr Leu Asn Gly Arg Val
            260                 265                 270

Lys Ser Thr Glu Leu Cys Ala Gly Asp Leu Ala Gly Gly Thr Asp Ser
        275                 280                 285

Cys Gln Gly Asp Ser Gly Gly Pro Leu Val Cys Phe Glu Lys Asp Lys
    290                 295                 300
```

Tyr Ile Leu Gln Gly Val Thr Ser Trp Gly Leu Gly Cys Ala Arg Pro
305                 310                 315                 320

Asn Lys Pro Gly Val Tyr Val Arg Val Ser Thr Tyr Val Pro Trp Ile
                325                 330                 335

Glu Glu Thr Met Arg Arg Tyr
            340

<210> SEQ ID NO 19
<211> LENGTH: 249
<212> TYPE: PRT
<213> ORGANISM: Homo sapiens

<400> SEQUENCE: 19

Ala Pro Ser Phe Asp Cys Gly Lys Pro Gln Val Glu Pro Lys Lys Cys
1               5                   10                  15

Pro Gly Arg Val Val Gly Gly Cys Val Ala His Pro His Ser Trp Pro
                20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
    50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245

<210> SEQ ID NO 20
<211> LENGTH: 750
<212> TYPE: DNA
<213> ORGANISM: artificial
<220> FEATURE:
<223> OTHER INFORMATION: optimized DNA sequence encoding micoplasmin of
      SEQ ID NO:19

<400> SEQUENCE: 20
gcaccttcat tcgactgtgg taagc

```
gtcggtggct gtgtggctca tcctcattct tggccttggc aagtgtctct tagaactaga    120
tttggtatgc acttctgtgg tggcaccttg atctcacctg aatgggtctt aaccgcagct    180
cattgtctgg agaagtcacc acgtccatct tcatacaagg tcatccttgg cgcacatcag    240
gaagtcaatc ttgagcctca tgttcaggag atcgaagtct ctcgtttgtt cttggaacca    300
actcgtaaag acattgctct tctgaagctg tcatctcctg ccgtgattac cgacaaggta    360
attcctgcct gcttgcctag tcctaattac gtcgttgccg accgtaccga atgcttcatt    420
actggttggg gtgagactca aggtacgttc ggtgctggtc tgttgaaaga agcacaatta    480
cctgtgattg agaacaaggt ttgtaacaga tacgagttcc tgaatggtcg tgttcagtcc    540
actgagttgt gtgcaggtca ccttgcaggt ggtactgata gttgtcaagg tgattctggt    600
ggaccactgg tgtgcttcga aaggataag tacatcttac aaggtgttac gtcttgggt    660 cttggatgtg ctcgtcctaa caagccaggt gtctacgtca gagtctccag attcgtaact    720
tggatcgaag gtgtcatgcg taacaactaa                                    750

<210> SEQ ID NO 21
<211> LENGTH: 38
<212> TYPE: DNA
<213> ORGANISM: artificial
<220> FEATURE:
<223> OTHER INFORMATION: synthetic oligonucleotide

<400> SEQUENCE: 21
gaagtgtcca ggtcgtattg tcggtggctg tgtggctc                             38

<210> SEQ ID NO 22
<211> LENGTH: 38
<212> TYPE: DNA
<213> ORGANISM: artificial
<220> FEATURE:
<223> OTHER INFORMATION: synthetic oligonucleotide

<400> SEQUENCE: 22
gagccacaca gccaccgaca atacgacctg gacacttc                             38

<210> SEQ ID NO 23
<211> LENGTH: 750
<212> TYPE: DNA
<213> ORGANISM: artificial
<220> FEATURE:
<223> OTHER INFORMATION: synthetic nucleotide sequence encoding Val1Ile
      microplasmin variant

<400> SEQUENCE: 23
gcaccttcat tcgactgtgg taagcctcag gtcgaaccta agaagtgtcc aggtcgtatt     60
gtcggtggct gtgtggctca tcctcattct tggccttggc aagtgtctct tagaactaga    120
tttggtatgc acttctgtgg tggcaccttg atctcacctg aatgggtctt aaccgcagct    180
cattgtctgg agaagtcacc acgtccatct tcatacaagg tcatccttgg cgcacatcag    240
gaagtcaatc ttgagcctca tgttcaggag atcgaagtct ctcgtttgtt cttggaacca    300
actcgtaaag acattgctct tctgaagctg tcatctcctg ccgtgattac cgacaaggta    360
attcctgcct gcttgcctag tcctaattac gtcgttgccg accgtaccga atgcttcatt    420
actggttggg gtgagactca aggtacgttc ggtgctggtc tgttgaaaga agcacaatta    480
cctgtgattg agaacaaggt ttgtaacaga tacgagttcc tgaatggtcg tgttcagtcc    540
actgagttgt gtgcaggtca ccttgcaggt ggtactgata gttgtcaagg tgattctggt    600
```

```
ggaccactgg tgtgcttcga gaaggataag tacatcttac aaggtgttac gtcttggggt    660
cttggatgtg ctcgtcctaa caagccaggt gtctacgtca gagtctccag attcgtaact    720
tggatcgaag gtgtcatgcg taacaactaa                                     750

<210> SEQ ID NO 24
<211> LENGTH: 249
<212> TYPE: PRT
<213> ORGANISM: artificial
<220> FEATURE:
<223> OTHER INFORMATION: amino acid sequence encoding Val1Ile
      microplasmin variant

<400> SEQUENCE: 24

Ala Pro Ser Phe Asp Cys Gly Lys Pro Gln Val Glu Pro Lys Lys Cys
1               5                   10                  15

Pro Gly Arg Ile Val Gly Gly Cys Val Ala His Pro His Ser Trp Pro
                20                  25                  30

Trp Gln Val Ser Leu Arg Thr Arg Phe Gly Met His Phe Cys Gly Gly
            35                  40                  45

Thr Leu Ile Ser Pro Glu Trp Val Leu Thr Ala Ala His Cys Leu Glu
        50                  55                  60

Lys Ser Pro Arg Pro Ser Ser Tyr Lys Val Ile Leu Gly Ala His Gln
65                  70                  75                  80

Glu Val Asn Leu Glu Pro His Val Gln Glu Ile Glu Val Ser Arg Leu
                85                  90                  95

Phe Leu Glu Pro Thr Arg Lys Asp Ile Ala Leu Leu Lys Leu Ser Ser
            100                 105                 110

Pro Ala Val Ile Thr Asp Lys Val Ile Pro Ala Cys Leu Pro Ser Pro
        115                 120                 125

Asn Tyr Val Val Ala Asp Arg Thr Glu Cys Phe Ile Thr Gly Trp Gly
    130                 135                 140

Glu Thr Gln Gly Thr Phe Gly Ala Gly Leu Leu Lys Glu Ala Gln Leu
145                 150                 155                 160

Pro Val Ile Glu Asn Lys Val Cys Asn Arg Tyr Glu Phe Leu Asn Gly
                165                 170                 175

Arg Val Gln Ser Thr Glu Leu Cys Ala Gly His Leu Ala Gly Gly Thr
            180                 185                 190

Asp Ser Cys Gln Gly Asp Ser Gly Gly Pro Leu Val Cys Phe Glu Lys
        195                 200                 205

Asp Lys Tyr Ile Leu Gln Gly Val Thr Ser Trp Gly Leu Gly Cys Ala
    210                 215                 220

Arg Pro Asn Lys Pro Gly Val Tyr Val Arg Val Ser Arg Phe Val Thr
225                 230                 235                 240

Trp Ile Glu Gly Val Met Arg Asn Asn
                245
```